US007991625B2

(12) United States Patent
Rosenfeld et al.

(10) Patent No.: US 7,991,625 B2
(45) Date of Patent: *Aug. 2, 2011

(54) SYSTEM FOR PROVIDING EXPERT CARE TO A BASIC CARE MEDICAL FACILITY FROM A REMOTE LOCATION

(75) Inventors: Brian A. Rosenfeld, Baltimore, MD (US); Michael Breslow, Lutherville, MD (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 994 days.

This patent is subject to a terminal disclaimer.

(21) Appl. No.: 11/444,082

(22) Filed: May 31, 2006

(65) Prior Publication Data

US 2006/0271409 A1 Nov. 30, 2006

Related U.S. Application Data

(63) Continuation-in-part of application No. 10/654,668, filed on Sep. 4, 2003, now Pat. No. 7,475,019, and a continuation-in-part of application No. 10/946,548, filed on Sep. 21, 2004, now Pat. No. 7,256,708, which is a continuation-in-part of application No. 09/443,072, filed on Nov. 18, 1999, now Pat. No. 6,804,656.

(60) Provisional application No. 60/141,520, filed on Jun. 23, 1999.

(51) Int. Cl.
G06Q 10/00 (2006.01)
A61B 5/00 (2006.01)

(52) U.S. Cl. .................... 705/2; 705/3; 600/300

(58) Field of Classification Search .................. 705/2–3; 600/300

See application file for complete search history.

(56) References Cited

U.S. PATENT DOCUMENTS 3,646,606 A 2/1972 Buxton et al.
(Continued)

FOREIGN PATENT DOCUMENTS

WO WO 98/29790 7/1998
(Continued)

OTHER PUBLICATIONS

Angus, D.C., et al. "Caring for the critically ill patient. Current and projected workforce requirements for care of the critically ill and patients with pulmonary disease: can we meet the requirements of an aging population?" (abstract) JAMA. Dec. 6, 2000; 284(21): 2762-70.

(Continued)

*Primary Examiner* — Robert W Morgan
*Assistant Examiner* — Rachel L Porter
(74) *Attorney, Agent, or Firm* — The Marbury Law Group, PLLC

(57) ABSTRACT

A system for providing expert care to a basic care medical facility (BCMF) from a remote location. The system facilitates real-time, continuous assessment of patients receiving care in a BCMF that is not generally equipped to provide expert medical care on a twenty-four basis. Patient monitoring equipment acquires monitored data elements from a patient monitoring station and transmits the monitoring data over a network to a remote command center. The remote command center also receives other patient data to the extent available from the BCMF. Alternatively, the patient monitored data is sent to a remote command center along with patient data at a pre-established time or when requested by remote command center. The delivery of stored monitoring data and patient data may be expedited if an urgent consultation is warranted. A rules engine continuously applies a patient-specific rule or rule set to the data elements selected from the assessment data from each BCMF monitored patient to determine whether intervention is warranted. Patient specific rules may be created that are consistent with the capabilities of the BCMF.

74 Claims, 9 Drawing Sheets

U.S. PATENT DOCUMENTS

| | | |
|---|---|---|
| 4,365,199 A | 12/1982 | McNair |
| 4,489,387 A | 12/1984 | Lamb et al. |
| 4,731,725 A | 3/1988 | Suto et al. |
| 4,838,275 A | 6/1989 | Lee |
| 4,852,570 A | 8/1989 | Levine |
| 4,878,175 A | 10/1989 | Norden-Paul et al. |
| 5,255,187 A | 10/1993 | Sorensen |
| 5,321,800 A | 6/1994 | Lesser |
| 5,348,008 A | 9/1994 | Bornn et al. |
| 5,544,649 A | 8/1996 | David et al. |
| 5,544,661 A | 8/1996 | Davis et al. |
| 5,574,828 A | 11/1996 | Hayward et al. |
| 5,576,952 A | 11/1996 | Stutman et al. |
| 5,619,991 A | 4/1997 | Sloane |
| 5,678,562 A | 10/1997 | Sellers |
| 5,701,894 A | 12/1997 | Cherry et al. |
| 5,715,449 A | 2/1998 | Peters, Jr. et al. |
| 5,724,580 A | 3/1998 | Levin et al. |
| 5,729,204 A | 3/1998 | Fackler et al. |
| 5,772,585 A | 6/1998 | Lavin et al. |
| 5,812,983 A | 9/1998 | Kumagai |
| 5,822,544 A | 10/1998 | Chaco et al. |
| 5,823,948 A | 10/1998 | Ross, Jr. et al. |
| 5,832,450 A | 11/1998 | Myers et al. |
| 5,839,438 A | 11/1998 | Graettinger et al. |
| 5,842,978 A | 12/1998 | Levy |
| 5,867,821 A | 2/1999 | Ballantyne et al. |
| 5,868,669 A | 2/1999 | Iliff |
| 5,899,855 A | 5/1999 | Brown |
| 5,942,986 A | 8/1999 | Shabot et al. |
| 5,987,519 A | 11/1999 | Peifer et al. |
| 6,024,699 A | 2/2000 | Surwit et al. |
| 6,093,146 A | 7/2000 | Filangeri |
| 6,102,856 A | 8/2000 | Groff et al. |
| 6,154,668 A | 11/2000 | Pedersen et al. |
| 6,168,563 B1 | 1/2001 | Brown |
| 6,215,403 B1 | 4/2001 | Chan et al. |
| 6,225,901 B1 | 5/2001 | Kail, IV |
| 6,230,142 B1 | 5/2001 | Begnino et al. |
| 6,234,964 B1 | 5/2001 | Iliff |
| 6,238,338 B1 | 5/2001 | DeLuca et al. |
| 6,245,013 B1 | 6/2001 | Minoz et al. |
| 6,254,536 B1 | 7/2001 | DeVito |
| 6,278,999 B1 | 8/2001 | Knapp |
| 6,292,698 B1 | 9/2001 | Duffin et al. |
| 6,304,788 B1 | 10/2001 | Eady et al. |
| 6,315,719 B1 | 11/2001 | Rode et al. |
| 6,364,834 B1 | 4/2002 | Reuss et al. |
| 6,385,589 B1 | 5/2002 | Trusheim et al. |
| 6,398,728 B1 | 6/2002 | Bardy |
| 6,442,433 B1 | 8/2002 | Linberg |
| 6,533,724 B2 | 3/2003 | McNair |
| 6,741,264 B1 | 5/2004 | Lesser |
| 6,835,176 B2 | 12/2004 | McNair |
| 6,893,396 B2 | 5/2005 | Schulze et al. |
| 2002/0002473 A1 | 1/2002 | Schrier et al. |
| 2002/0177758 A1 | 11/2002 | Schoenberg et al. |
| 2002/0177759 A1 | 11/2002 | Schoenberg et al. |
| 2002/0187483 A1 | 12/2002 | Hoffman et al. |
| 2002/0193667 A1 | 12/2002 | McNair |
| 2003/0036687 A1 | 2/2003 | Schoenberg et al. |
| 2004/0030578 A1 | 2/2004 | Cross et al. |
| 2004/0063031 A1 | 4/2004 | Gallucci et al. |
| 2004/0078366 A1 | 4/2004 | Crooks et al. |
| 2004/0193451 A1 | 9/2004 | McNair |
| 2004/0197813 A1 | 10/2004 | Hoffman et al. |
| 2004/0199333 A1 | 10/2004 | Hoffman et al. |
| 2004/0225201 A1 | 11/2004 | McNair |
| 2004/0236604 A1 | 11/2004 | McNair |
| 2005/0027563 A1 | 2/2005 | Fackler et al. |
| 2005/0049891 A1 | 3/2005 | Wilson |
| 2005/0060191 A1 | 3/2005 | Parkins et al. |
| 2005/0075794 A1 | 4/2005 | Hoffman et al. |
| 2005/0075904 A1 | 4/2005 | Wagner et al. |
| 2005/0076060 A1 | 4/2005 | Finn et al. |
| 2005/0125098 A1 | 6/2005 | Wang et al. |
| 2005/0125256 A1 | 6/2005 | Schoenberg et al. |
| 2005/0206518 A1 | 9/2005 | Welch et al. |
| 2005/0228241 A1 | 10/2005 | McNair |
| 2005/0251418 A1 | 11/2005 | Fox, Jr. et al. |
| 2005/0267351 A1 | 12/2005 | Humphrey et al. |
| 2005/0283062 A1 | 12/2005 | Hoffman et al. |
| 2006/0031018 A1 | 2/2006 | Bush et al. |
| 2006/0036542 A1 | 2/2006 | McNair |

FOREIGN PATENT DOCUMENTS

| | | |
|---|---|---|
| WO | WO 99/13766 | 3/1999 |
| WO | 00/79466 A2 | 12/2000 |

OTHER PUBLICATIONS

Celi, Leo Anthony, et al. "The eICU: It's Not Just Telemedicine." Crit. Care Med. 2001, vol. 29, No. 8 (Suppl.).

Hanson, C.W. 3rd, et al. "Effects of an organized critical care service on outcomes and resource utilization: a cohort study." (abstract) Crit. Care Med. Feb. 1999; 27(2):270-4.

Manthous, C.A., et al. "Effects of a medical intensivist on patient care in a community teaching hospital." (abstract) Mayo Clin. Proc. May 1997; 72(5):391-9.

Pronovost, P.J., et al. "Organizational characteristics of intensive care units related to outcomes of abdominal aortic surgery." (abstract) JAMA. Apr. 14, 1999; 281(14):1310-7.

Pronovost, Peter J., et al. "Physician Staffing Patterns and Clinical Outcomes in Critically Ill Patients: A Systematic Review." JAMA. Nov. 6, 2002; 288(17):2151-62.

"Remote Control." Modern Healthcare, Feb. 25, 2002 (4 pages).

Breslow, Michael J., et al. "Technology Strategies to Improve ICU Practice." Seminars in Anesthesia 24: 59-70, 2005.

Breslow, Michael J. "Remote ICU Care Programs: Current Status." J. Crit. Care: 22, 66-76, 2007.

Claim Construction Of United States Patent No. 6,804,656 ("the '656 patent") and United States Patent No. 7,256,708 ("the '708 patent"), Cerner Corporation vs. Visicu, Inc.; Case No. 04-1033-CV-W-GAF; United States District Court For The Western District of Missouri, Western Division, Jul. 23, 2008.

Memorandum and Order, *VISICU, Inc* vs. *IMDSOFT. Ltd. et al.*, Civil Action No. 07-4562; United States District Court For The Eastern District Of Pennsylvania, May 7, 2009.

Mark_LoBue_Depostion_03_06_09.pdf.
LoBue_Exhibit_No_02.pdf.
LoBue_Exhibit_No_03.pdf.
LoBue_Exhibit_No_04.pdf.
LoBue_Exhibit_No_05.pdf.
LoBue_Exhibit_No_06.pdf.
LoBue_Exhibit_No_07.pdf.
LoBue_Exhibit_No_08.pdf.
LoBue_Exhibit_No_09.pdf.
LoBue_Exhibit_No_010.pdf.
LoBue_Exhibit_No_011.pdf.
LoBue_Exhibit_No_012.pdf.
Gerald_Mossinghoff_Deposition.pdf.
Mossinghoff_Ex_1.pdf.
Mossinghoff_Ex_2.pdf.
Mossinghoff_Ex_4.pdf.
Mossinghoff_Ex_5.pdf.
Jon_Roberts_Depostions.pdf.
10083_Roberts_Jon_031809_Exhibit_03.pdf.
10083_Roberts_Jon_031809_Exhibit_06.pdf.
10083_Roberts_Jon_031809_Exhibit_07.pdf.
10083_Roberts_Jon_031809_Exhibit_08.pdf.
10083_Roberts_Jon_031809_Exhibit_09.pdf.
10083_Roberts_Jon_031809_Exhibit_10.pdf.
10083_Roberts_Jon_031809_Exhibit_11.pdf.
10083_Roberts_Jon_031809_Exhibit_12.pdf.
10083_Roberts_Jon_031809_Exhibit_13.pdf.
10083_Roberts_Jon_031809_Exhibit_14.pdf.
10083_Roberts_Jon_031809_Exhibit_15.pdf.
10083_Roberts_Jon_031809_Exhibit_16.pdf.
10083_Roberts_Jon_031809_Exhibit_17.pdf.
10083_Roberts_Jon_031809_Exhibit_18.pdf.
Charles_Safran_Deposition.pdf.
Michael_Shabot_Deposition.pdf.

Michael_Shabot_Exhibit_1.pdf.
Michael_Shabot_Exhibit_2.pdf.
Michael_Shabot_Exhibit_3.pdf.
Michael_Shabot_Exhibit_4.pdf.
Michael_Shabot_Exhibit_5.pdf.
Michael_Shabot_Exhibit_6.pdf.
Cerner Markman Hearing Transcript.
iMDSoft Markman Hearing Transcript Day 1.
iMDSoft Markman Hearing Transcript Day 2.
Original Premarket 510(k) Notification of IC-USA—vol. 1.
Original Premarket 510(k) Notification of IC-USA—vol. 2.
Original Premarket 510(k) Notification of IC-USA—vol. 3.
Original Premarket 510(k) Notification of IC-USA—vol. 4.
Summary of Safety and Effectiveness.
Premarket 510(k) Notification of Vital Com.
Premarket 510(k) Notification of Hewlett-Packard.
Special 510(k) Notification of Visicu.
Communication Re Vital Com 510K.
Editors: M. Michael Shabot and Reed M. Gardner, Computers and Medicine: Decision Support Systems in Critical Care, 1994, Springer-Verlag New York, Inc. New York.
Gilad J. Kuperman, M.D. and Reed M. Gardner, Ph.D., The Help System: A Snapshot in Time, 1988, Dept. of Biophysics, LDS Hospital, Salt Lake City, Utah.
Project Leaders: Benoit Dawant, Ph.D. And John A. Morris, Jr. M.D., Vanderbilt University Simon Project Website, 2004, Vanderbilt University, Nashville, Tennessee.
Greg Borzo, Web Technology: Coming Soon to a Hospital Near You, American Medical News, Nov. 18, 1996, American Medical Association www.amednews.com.
Abstract: J.E. Gray, C. Safran, R.B. Davis, G. Pomilio-Weitzner, J.E. Stewart, L. Zaccagnini and D. Pursley, Baby Care Link: Using the Internet and Telemedicine to Improve Care for High-risk Infants, Dec. 2000, Pediatrics, vol. 106, No. 6, pp. 1318-1324.
Abstract: Ray Duncan and Jeffrey J. Pomerance, Computer Assistance in Delivery of Patient Care in a Neonatal Intensive Care Unit, The Use of Computers in Perinatal Medicine, Chapter 19, pp. 337-351, 1982, Praeger Publishers, New York, NY.
Abstract: Ray Duncan, MD, Computer Assisted Care in the Neonatal Intensive Care Unit, Proceedings of the 17th Annual Symposium on Computer Applications in Medical Care, Nov. 1993, p. 929, American Medical Informatics Association.
Abstract: Metnitz PG, Laback P. Popow C, Laback 0, Lenz K, Hiesmayr M, Computer assisted data analysis in intensive care: the ICDEV project—development of a scientific database system for intensive care (Intensive Care Data Evaluation Project), International Journal of Clinical Monitoring and Computing, 1995, vol. 12, No. 3, pp. 147-159.
Abstract: Paul H. Peristein, MD, Neil K. Edwards, MS, Harry D. Atherton, MS, James M. Sutherland, MD, Computer Assisted Newborn Intensive Care, Pediatrics, Apr. 1976, vol. 57, No. 4, pp. 494-501.
Abstract: Edward H. Shortliffe, MD, PHD, Computer Programs to Support Clinical Decision Making, JAMA, Jul. 3, 1987, vol. 258, No. 1, pp. 61-66.
Abstract: Merz U, Peschgens T, Budde R, Kretzschmann F, Homchen H V, Computer-assisted monitoring in the neonatal intensive care unit [German], Klin Padiatr, Nov./Dec. 1995, vol. 207, No. 6, pp. 331-333.
Abstract: Charles Safran, MD, Francois Herrman, MD, David Rind, MD, Hollis B. Kowaloff, BA, Howard L. Bleich, MD, and Warner V. Slack, MD, Computer-Based Support for Clinical Decision Making, M.D. Computing, 1990, vol. 7, No. 5, pp. 319-322.
Abstract: Reed M. Gardner, PHD, Computerized Management of Intensive Care Patients, M.D. Computing, 1986, vol. 3, No. 1, pp. 36-51.
Abstract: F. John Lewis; Steven Deller; Michael Quinn; Benjamin Lee; Raymond Will; and John Raines, Continuous Patient Monitoring with a Small Digital Computer, Computers and Biomedical Research;1972, vol. 5; pp. 411-428.
Abstract: N. Fumai, C. Collet, M. Petroni, K. Roger, A. Lam, E. Saab, A.'S. Malowany, F. A. Carnevale, R. D. Gottesman, Database Design of an Intensive Care Unit Patient Data Management System, Proceedings of the Fourth Annual IEEE Symposium on Computer-Based Medical Systems, May 12, 1991, pp. 78-85, IEEE Computer Society Press, Los Alamitos, CA.
Abstract: George Hripcsak; Paul D. Clayton; Robert A. Jenders; James J. Cimino; and Stephen B. Johnson, Design of a Clinical Event Monitor, Computers and Biomedical Research, Jun. 1996, vol. 29, No. 3, pp. 194-221.
Abstract: David M. Rind, MD; Roger Davis, SCD; and Charles Safran, MD, Designing Studies of Computer-Based Alerts and Reminders, MD Computing, 1995, vol. 12, No. 2, pp. 122-126.
Abstract: Dwayne R. Westenkow, PHD, Automating Patient Care with Closed-Loop Control, M.D. Computing, 1986, vol. 3, No. 2, pp. 14-20.
Abstract: Snowden S, Brownlee KG, Dear P R, An expert system to assist neonatal intensive care, I Med Eng Technol Mar.-Apr. 1997;21(2):67-73, vol. 21, No. 2, pp. 67-73.
Abstract: A. Aifredo Morales, ENGR., MS, James Gray, MD, MS, Charles Safran, MD, An Application Server Approach for Integration of Clinical Systems, Proceedings of the AMIA 1999 Annual Symposium, 1999, AMIA.
Abstract: Kang Wang, PHD; Isaac Kohane, MD, PHD; Karen L. Bradshaw, BS; James Facider, MD, A Real Time Patient Monitoring System on the World Wide Web, Proceedings of the 1996 AMIA Annual Fall Symposium, Nov. 1996, pp. 729-732, Hanley and Belfus, Inc.
Abstract: Michael Factor, David H. Gelernter, Craig E. Kolb, Perry L. Miller and Dean F. Sittig, Real-Time Data Fusion in the Intensive Care Unit, IEEE Computer, Nov. 1991, pp. 45-53.
Editor: Judy G. Ozbolt, Ph.D., A Conference of the American Medical Informatics Association, Symposium on Computer Applications in Medical Care, Nov. 5-9, 1994, Hanley & Belfus, Inc. Medical Publishers, Philadelphia, PA.
W. Hsueh-Fen Young, Reed M. Gardner, Thomas D. East and Kristi Turner, Computerized Ventilator Data Selection: Artifact Rejection and Data Reduction, Int'l Journal of Clinical Monitoring and Computing 1997, 14: 165-176, Kluwer Academic Publishers, Netherlands.
Randolph A. Miller, M.D. and Reed M. Gardner, Ph.D., Summary Recommendations for Responsible Monitoring and Regulation of Clinical Software Systems, Annals of Internal Medicine, Nov. 1997, vol. 127, No. 9.
Reed M. Gardner, T. Allan Pryor and Homer R. Warner, The HELP Hospital Information System: Update 1998, Intl Journal of Medical Informatics 1999, vol. 54, pp. 169-182, Elsevier Science Ireland Ltd., Ireland.
Martin Spikoff, Systems Aid Rural Health Delivery, QIPhysician. com, Sep. 2003.
Abstract: Jerome P. Kassirer, MD, The Next Transformation in the Delivery of Health Care (Editorial), NEJM, Jan. 5, 1995, vol. 332, No. 1, pp. 52-54.
Abstract: Lorene S. Avila; M. Michael Shabot, Keys to the successful implementation of an ICU patient data management system, International Journal of Clinical Monitoring and Computing, 1988, vol. 5, pp. 15-25.
Abstract: Reed M. Gardner, MD; M. Michael Shabot, MD, Computerized ICU Data Management: Pitfalls and Promises, International Journal of Clinical Monitoring and Computing, 1990, vol. 7, pp. 99-105.
Karl W. Thomas, M.D., Charles S. Dayton, B.S., R.Ph., and Michael W. Peterson, M.D., Evolution of Internet-Based Clinical Decision Support Systems, Journal of Medical Internet Research 1999, vol. 1, University of Iowa, Iowa City, Iowa.
Abstract: C. J. McDonald, Protocol-Based Computer Reminders, The Quality of Care and The Non-Perfectability of Man, The New England Journal of Medicine, Dec. 9, 1976, vol. 295, No. 24, 1351-1355.
Abstract: T.D. East, A.H. Morris, C.J. Wallace, T.P. Clemmer, J.F. Orme, Jr., L.K. Weaver, S. Henderson and D.F. Sittig, A Strategy for Development of Computerized Critical Care Decision Support Systems, Intl Journal of Clinical Monitoring and Computing, 1991-92, vol. 8, No. 4, 263-269.

Dr. Ramana Reddy and Dr. V. "Juggy" Jagannathan, Secure Collaboration Technology for Rural Clinical Telemedicine, National Library of Medicine, Oct. 8, 1996 Press Release, West Virginia University, West Virginia.

West Virginia University Research Corporation, Secure Collaboration Technology for Rural Clinical Telemedicine: Final Report, National Library of Medicine.

Martin J. Tobin, M.D., Principles and Practice of Intensive Care Monitoring, 1998, McGraw-Hill Inc.

Peter J. Haug, Reed M. Gardner, and R. Scott Evans, "Hospital-Based Decision Support" in *Clinical Decision Support Systems: Theory and Practice*, ETA S. Berner [ed.], 1999, Springer-Verlag New York, Inc., New York, NY, pp. 77-103.

Clement J. McDonald, M.D. and William M. Tierney, M.D., Computer-Stored Medical Records: Their Future Role in Medical Practice, JAMA, Jun. 17, 1988, pp. 3433-3440, vol. 259, No. 23.

Gilad J. Kuperman, Reed M. Gardner, and T. Allan Pryor, HELP: A Dynamic Hospital Information System, 1991, Springer-Verlag New York, Inc., New York, NY.

M. Michael Shabot, M.D., Mark Lobue, B.S., and Jeannie Chen, Pharm.D., Wireless Clinical Alerts for Physiologic, Laboratory and Medication Data, Department of Enterprise Information Services, Surgery and Pharmacy Cedars-Sinai Health System, Los Angeles, CA.

Chaoxin Sima, Ravi Raman, Ramana Reddy, William Hunt and Sumitra Reddy, Vital Signs Services for Secure Telemedicine Applications, Concurrent Engineering Research Center, West Virginia University, Morgantown, WV.

Dickey Seidlitz Johnson, Jane Ranzenberger, Ruth D. Herbert, Reed M. Gardner, and Terry P. Clemmer, A Computerized Alert Program for Acutely Ill Patients, Journal of Nursing Administration, Jun. 1980, pp. 26-35.

Reed M. Gardner, Ph.D., Blair J. West, M.S., T. Allan Pryor, Ph.D., Keith G Larsen, R.Ph., Homer R Warner, M.D., Terry P Clemmer, M.D., James F. Orme, Jr. M.D., Computer-Based ICU Data Acquisition as an Aid to Clinical Decision-Making, Critical Care Medicine, 1982, pp. 823-830, vol. 10, No. 12, The Williams & Wilkins Co.

Reed M. Gardner and Terry, P. Clemmer, Computerized Protocols Applied to Acute Patient Care, 1977, Mediad Inc., Tarrytown, NY.

Karen E. Bradshaw, Reed M. Gardner, and T. Allan Pryor, Development of a Computerized Laboratory Alerting System, Computers and Biomedical Research 22, 575-587, 1989, Academic Press, Inc.

Terry P. Clemmer and Reed M. Gardner, Medical Informatics in the Intensive Care Unit: State of the Art 1991, International Journal of Clinical Monitoring and Computing 8: 237-250, 1992, Kluwer Academic Publishers, Netherlands.

Reed M. Gardner, Ph.D., David V. Ostler, and O. Hank Duffy, M.D., Computers in the Emergency Room, Internal Medicine for the Specialist, vol. 8, No. 3, Mar. 1987.

Dean F. Sittig, Nathan L. Pace, Reed M. Gardner, Eduardo Beck, and Alan H. Morris, Implementation of a Computerized Patient Advice System Using the HELP Clinical Information System, Computers and Biomedical Research 22, 474-487, 1989, Academic Press Inc.

P. D. Clayton, R. Scott Evans, T. Pryor, R. M. Gardner, P. J. Haug, O. B. Wigertz, and H. R. Warner, Bringing HELP to the Clinical Laboratory—Use of an Expert System to Provide Automatic Interpretation of Laboratory Data, Ann Clin Biochem 1987; 24: Supplement.

D. F. Sittig, Ph.D., R. M. Gardner, Ph.D., N. L. Pace, M.D., M. Bombino, M. D., and A. H. Morris, M.D., Compas: A Computerized Patient Advice System to Direct Ventilatory Care, Medical Informatics 88: Computers in Clinical Medicine, Sep. 13-15, 1988, British Medical Informatics Society, London.

Karen E. Bradshaw, Ph.D., Dean F. Sittig, Ph.D., Reed M. Gardner, Ph.D., T. Alllan Pryor, Ph.D., and Marge Budd, M.S., Improving Efficiency and Quality in a Computerized ICU, 1988 SCAMC, Inc.

Dean F. Sittig, Ph.D., C. Gregory Elliott, M.D., C. Jane Wallace, R.N., B.S.N., Polly Bailey, R.N., Reed M. Gardner, Ph.D., Computerized Screening for Identification of Adult Respiration Distress Syndrome (ARDS) Patients, 1988 SCAMC, Inc.

R. Scott Evans, Ph.D., Reed M. Gardner, Ph.D., John P. Burke, M.D., Stanley L. Pestotnik, R.P.H., Robert A. Larsen, M.D., David C. Classen, M.D., and Paul D. Clayton, Ph.D., A Computerized Approach to Monitor Prophylactic Antibiotics, 1987, SCAMC, Inc.

Susan Henderson, B.A., Thomas D. East, Ph.D., Alan H. Morris, M.D., Reed M. Gardner, Ph.D., Performance evaluation of computerized clinical protocols for management of arterial hypoxemia in ARDS patients, LDS Hospital, and University of Utah, Salt Lake City, UT.

Thomas D. East, Ph.D., Susan Henderson, B.A., Alan H. Morris, M.D., Reed M. Gardner, Ph.D., Implementation Issues and Challenges for Computerized Clinical Protocols for Management of Mechanical Ventilation in ARDS Patients, LDS Hospital, Salt Lake City, UT.

C. Gregory Elliott, M.D., Deon Simmons, R.R.T., C. Duwayne Schmidt, M.D., Kip Enger, B.S., C.R.T.T., Loren Greenway, B.S., R.R.T., and Reed M. Gardner, Ph.D., Computer-Assisted Medical Direction of Respiratory Care, Respiratory Management, vol. 19, No. 2.

H. Keller and CH. Trendelenburg, Data Presentation Interpretation, Clinical Biochemistry Principles, Methods, Applications, WalterdeGruyter & Co., 1989.

Reed M. Gardner, Ph.D., Karen W. Hollingsworth, R.N., M.S, C.C. R.N., ECG and Pressure Monitoring: How to Obtain Optimal Results, 295-305.

Reed M. Gardner, Ph.D., Dean F. Sittig, M.S., Marge C. Budd, R.N., M.S., Computers in the Intensive Care Unit: Match or Mismatch?, 248-259.

Emmanuel Furst, Ph.D., Cardiovascular Technology, The Journal of Cardiovascular Nursing, Nov. 1989, 68-78.

Dean F. Sittig, Reed M. Gardner, Nathan L. Pace, Alan H. Morris, and Eduardo Beck, Computerized Management of Patient Care in a Complex, Controlled Clinical Trial in the Intensive Care Unit, Computer Methods and Programs in Biomedicine 30, 1989, 77-84.

Karen E. Bradshaw, Ph.D., Dean F. Sittig, Ph.D., Reed M. Gardner, Ph.D., T. Allan Pryor, Ph.D., and Marge Budd, R.N., M.S., Computer-Based Data Entry for Nurses in the ICU, Clinical Computing, Nov. 1988.

Robert A. Larsen, M.D., R. Scott Evans, Ph.D., John P. Burke, M.D., Stanley L. Pestonik, R.Ph., Reed M. Gardner, Ph.D., David C. Classen, M.D., Improved Perioperative Antibiotic Use and Reduced Surgical Wound Infections Through Use of Computer Decision Analysis, Computer Applications for Surgical Prophylaxis/Larsen et al.

R. M. Gardner, Computers in the ICU and Surgery-Keeping Real-Time Patient Records for Decision-Making.

Thomas D. East, Ph.D., Alan H. Morris, M.D., Terry Clemmer, M.D., James F. Orme, M.D., C. Jane Wallace, B.S.N., Susan Henderson, B.A., Dean F. Sittig, Ph.D., Reed M. Gardner, Ph.D., Development of Computerized Critical Care Protocols—A Strategy That Really Works!, 1990 LDS Hospital, Salt Lake City, UT.

R. Scott Evans, Ph.D., John P. Burke, M.D., Stanley L. Pestonik, R.Ph., David C. Classen, M.D., Ronald L. Menlove, Ph.D., and Reed M. Gardner, Ph.D., Prediction of Hospital Inflections and Selection of Antibiotics Using an Automated Hospital Database, 1990, SCAMC, Inc. 663-667.

Susan E. Henderson, B.A., Robert O. Crapo, M.D., Thomas D. East, Ph.D., Alan H. Morris, M.D., C. Jane Wallace, R.N., Reed M. Gardner, Ph.D., Computerized Clinical Protocols in an Intensive Care Unit: How Well are They Followed?, 1990, SCAMC, Inc., LDS Hospital, Salt Lake City, UT.

Reed M. Gardner, PHD, Russell K. Hulse, RPH, MBA, Keith G. Larsen, RPH, Assessing The Effectiveness Of A Computerized Pharmacy System, 1990, SCAMC, Inc., 668-672.

Reed M. Gardner, "Patient-Monitoring Systems", *Medical Informatics: Computer Applications in Health Care*, E.H. Shortliffe and L.E. Perrealt (eds.), G. Wiederhold and L.M. Fagan (assoc. eds.) (Reading, MA: Addison-Wesley, 1990.

Reed M. Gardner, Olaf K. Golubjatnikov, R. Myron Laub, Julie T. Jacobson, and R. Scott Evans, Computer-Critiqued Blood Ordering Using the HELP System, Computers and Biomedical Research 23, 514-528, 1990, Academic Press, Inc.

Karen E. Tate, Ph.D., Reed M. Gard'Ner, Ph.D., and Lindell K. Weaver, M.D., A Computerized Laboratory Alerting System, Clinical Computing, 1990, vol. 7, No. 5, 296-301.

Dean F. Sittig, Reed M. Gardner, Alan H. Morris, and C. Jane Wallace, Clinical Evaluation of Computer-Based Respiratory Care Algorithms, International Journal of Clinical Monitoring and Computing 7, 1990, 177-185, Kluwer Academic Publishers, Netherlands.

R. Scott Evans, Stanley L. Pestotnilc, John P. Burke, Reed M. Gardner, Robert A. Larsen, and David C. Classen, Reducing Tile Duration Of Prophylactic Antibiotic Use Through Computer Monitoring Of Surgical Patients, DICP, The Annals of Pharmacotherapy, Apr. 1990, vol. 24, 351-354, Harvey Whitney Books Company, Cincinnati, OH.

Reed M. Gardner, and M. Michael Shabot, Computerized ICU Data Management: Pitfalls and Promises, International Journal of Clinical Monitoring and Computing 7: 99-105, 1990, Kluwer Academic Publishers, Netherlands.

Stanley L. Pestotnik, R.PH., R. Scott Evans, PH.D., John P. Burke, M.D., Reed M. Gardner, PH.D., David C. Classen, M.D., Therapeutic Antibiotic Monitoring: Surveillance Using a Computerized Expert System, The American Journal of Medicine, Jan. 1990, vol. 88, 43-48.

Gil Kuperman, MD, Brent James, MD, MSTAT, Julie Jacobsen, MT (ASCP), Reed M. Gardner, PHD, Continuous Quality Improvement Applied To Medical Care: Experiences At LDS Hospital, Medical Decision Making, Oct.-Dec. 1991, 60-65, vol. 11, No. 4.

Susan Henderson, Robert O. Crapo, C. Jane Wallace, Thomas D. East, Alan H. Morris, & Reed M. Gardner, Performance Of Computerized Protocols For The Management Of Arterial Oxygenation In An Intensive Care Unit, International Journal of Clinical Monitoring and Computing 8, 1992, 271-180, Kluwer Academic Publishers, Netherlands.

Reed M. Gardner, Ph.D., William L. Hawley, Thomas D. East, Ph.D., Thomas A. Oniki, B.S., Hsueh-Fen W. Young, B.S., Real Time Data Acquisition: Experience With the Medical Information Bus (MIB), LDS Hospital, University of Utah, Salt Lake City, UT.

Eric F. Lepage, MD, Reed M. Gardner, PHD, R. Myron Laub, MD, Julie T. Jacobson, MT(ASCP), Assessing The Effectiveness Of A Computerized Blood Order Consultation' System, LDS Hospital, 1992, 33-37, AMIA, Inc.

R. Scott Evans, PH.D., Stanley L. Pestotnik, R.PH., David C. Classen, M.D., Sheron B. Bass, B.S.N. Ronald L. Menlove, PH.D., Reed M. Gardner, PH.D., and John P. Burke, M.D., Development Of A Computerized Adverse Drug Event Monitor, LDS Hospital and University of Utah, Salt Lake City, UT.

E. Lepage, R. Traineau, PH. Marchetti, M. Benbunan, R. M. Gardner, Development Of A Computerized Knowledge Based System Integrated To A Medical Workstation: Application To Blood Transfusion, MEDINFO, 1992, 585-590, Elsevier Science Publishers B.V.

Reed M. Gardner, Ph.D. and R. Scott Evans, Ph.D., Computer-Assisted Quality Assurance, Group Practice Journal, May/Jun. 1992, 41(3), 8-11.

Thomas D. East, Ph.D., W. Hsueh-Fen Young, M.S., and Reed M. Gardner, Ph.D., Digital Electronic Communication between ICU Ventilators and Computers and Printers, Respiratory Care, Sep. 1992, vol. 37 No. 9, 1113-1123.

Reed M. Gardner, Computers in Critical Care, Wellcome Trends in Hospital Pharmacy, Jul. 1992.

T. Allan Pryor, Reed M. Gardner and W. Clinton Day, Computer System for Research and Clinical Application to Medicine, AFIPS—Conference Proceedings, vol. 33, 1968, 809-816.

Homer R. Warner, M.D., Reed M. Gardner and Alan F. Toronto, M.D., Computer-Based Monitoring of Cardiovascular Functions in Postoperative Patients, Supplement II to Circulation, Apr. 1968, vols. 37 & 38, 68-74.

Russell M. Nelson, Homer R. Warner, Reed E. Gardner and J. D. Mortensen, Computer Based Monitoring of Patients Following Cardiac Surgery, Computers in Cardiology, Jul.-Aug. 1969, vol. 5, No. 4, 926-930.

Reed M. Gardner, Computerized Patient Monitoring at LDS Hospital—An Evaluation, Proceedings of the San Diego Biomedical Symposium, 1971, vol. 10, 151-159.

Reed M. Gardner, Monitoring of Physiological Data in a Clinical Environment, Annual Review of Biophysics and Bioengineering, 1972, vol. 1, 211-224.

Reed M. Gardner, Computerized Intensive Care Monitoring at LDS Hospital—Progress and Development, 97-105.

Reed M. Gardner, Donald R. Bennet, and Richard B Vorce, Eight-Channel Data Set for Clinical EEG Transmission Over Dial-Up Telephone Network, IEEE Transactions on Biomedical Engineering, May 1974, vol. BME-21, No. 3, 246-249.

Reed M. Gardner, George H. Cannon, Alan H. Morris, Kenneth R. Olsen, W. Gary Price, Computerized Blood Gas Interpretation and Reporting System, Computer Magazine, Jan. 1975, 39-45.

Russell K. Hulse, Stephen J. Clark, J. Craig Jackson, Homer R. Warner and Reed M. Gardner, Computerized Medication Monitoring System, American Journal of Hospital Pharmacy 33, Oct. 1976, 1061-1064.

Reed M. Gardner, Ph.D., Computers in the ICU, Medical Electronics, Jun. 1984, 129-135.

Robert D. Andrews, M.S., M.T., Reed M. Gardner, Ph.D., Sandy M. Metcalf, R.R.T., and Deon Simmons, R.R.T., Computer Charting: An Evaluation of a Respiratory Care Computer System, Respiratory Care, Aug. 1985, vol. 30, No. 8, 695-707.

Reed M. Gardner, Ph.D., Computerized Data Management and Decision Making in Critical Care, Symposium on Critical Care, Aug. 1985, vol. 65, No. 4, 1041-1051.

Reed M. Gardner, David P. Scoville, Blair J. West, Beth Bateman, Robert M. Cundick, Jr., Terry P. Clemmer, Integrated Computer Systems for Monitoring of the Critically Ill, 1977, 301-307.

T. Allan Pryor, Reed M. Gardner, Paul D. Clayton, Homer R. Warner, A Distributed Processing System for Patient Management, Computers in Cardiology, Sep. 1978, 325-328.

Reed M. Gardner, Ph.D., Terry P. Clemmer, M.D., Keith G. Larsen, R.Ph., and Dickey S. Johnson, R.N., Computerized Alert System Use in Clinical Medicine, IEEE Session 6, 1979, 136-140.

T. Allan Pryor, Homer R. Warner, Reed M. Gardner, HELP—A Total Hospital Information System.

T. P. Clemmer, R. M. Gardner, J. F. Orme, Jr., Computer Support in Critical Care Medicine, 1980.

Scott R. Cannon, and Reed M. Gardner, Experience with a Computerized Interactive Protocol System Using HELP, Computers and Biomedical Research 13, 1980, 399-409, Academic Press, Inc.

T. Allan Pryor, Paul D. Clayton, Reed M. Gardner, Randy Waki, and Homer R. Warner, HELP—A Hospital-Wide System for Computer-Based Support of Decision-Making, Jan 1981.

T. A. Pryor, R. M. Gardner, P. D. Clayton and H. R. Warner, The HELP System, Proceedings of the Sixth Annual Symposium on Computer Applications in Medical Care, Oct.-Nov. 1982, 19-27, IEEE.

Reed M. Gardner, Information Management—Hemodynamic Monitoring, Seminars in Anesthesia, Dec. 1983, vol. 2, No. 4, 287-299.

T. A. Pryor, R. M. Gardner, P. D. Clayton, H. R. Warner, The HELP System, Journal of Medical Systems, 1983, vol. 7, No. 2, 87-102.

Reed M. Gardner, Blair J. West, T. Allan Pryor, Distributed Data Base and Network for ICU Monitoring, IEEE Computers in Cardiology, Sep. 18-24, 1984, 305-307.

Reed M. Gardner, T. Allan Pryor, Paul D. Clayton, and R. Scott Evans, Integrated Computer Network for Acute Patient Care, Symposium on Computer Applications in Medical Care, Nov. 4-7, 1984.

Reed M. Gardner, Tomorrow's Electronic Hospital is Here Today, IEEE Spectrum, Jun. 1984, 101-103.

Karen E. Bradshaw, Reed M. Gardner, Terry P. Clemmer, Jams F. Orme, Frank Thomas, and Blair J. West, Physician Decision Making—Evaluation of Data Used in a Computerized ICU, International Journal of Clinical Monitoring and Computing 1, 1984, 81-91.

Terry P. Clemmer, M.D., and Reed M. Gardner, Ph.D., Data Gathering, Analysis, and Display in Critical Care Medicine, Respiratory Care, Jul. 1985, vol. 30, No. 7, 586-601.

Reed M. Gardner, Ph.D., and William L. Hawley, Standardizing Communications and Networks in the ICU, Patient Monitoring and Data Management, 1985, 59-63.

R. Scott Evans, Reed M. Gardner, Allan R. Bush, John P. Burke, Jay A. Jacobson, Robert A. Larsen, Fred A. Meier, and Homer R. Warner, Development of a Computerized Infectious Disease Monitor (CIDM), Computers and Biomedical Research 18, 1985, 103-113.

Reed M. Gardner, Ph.D., Susan M. Monis, Paul Oehler, Monitoring Direct Blood Pressure: Algorithm Enhancements, 607-610.

R. Scott Evans, PHD, Robert A. Larsen, MD, John P. Burke, MD, Reed M. Gardner, PHD, Frederick A. Meier, MD, Jay A. Jacobson, MD, Marlyn T. Conti, BSN, Julie T. Jacobson, MT, Russell K. Hulse, RPH, Computer Surveillance of Hospital-Acquired Infections and Antibiotic Use, Journal of the American Medical Association, Aug. 22-29, 1986, vol. 256, No. 8, 1007-1011.

Reed M. Gardner, Computerized Management of Intensive Care Patients, Images, Signals, and Devices, 1986, vol. 3, No. 1.

R. Whiting, L. Hayes, The Practice of Telemedicine—The TARDIS Perspective, Informatics in Healthcare—Australia, Jul./Aug. 1997, vol. 6, No. 3, 103-106.

Monique Frize, Robin Walker, Clinical Decision-Support Systems for Intensive Care Units Using Case-Based Reasoning.

Ho Sung Lee, Seung Hun Park, and Eung Je Woo, Remote Patient Monitoring Service Through World-Wide Web, Proceedings—19th International Conference—IEEE/EMBS, Oct. 30-Nov. 2, 1997, 928-931.

Betty L. Grundy, M.D., Pauline Crawford, R.N., Paul K. Jones, Ph.D., May Lou Kiley, Ph.D., Arnold Reisman, Ph.D., Yoh-Han Pao, Ph.D., Edward L. Wilkerson, M.D., J. S. Gravenstein, M.D., Telemedicine in Critical Care: An Experiment in Health Care Delivery, Oct. 1977, 6:10.

Betty Lou Grundy, M.D., Paul K. Jones, Ph.D., and Ann Lovitt, M.D., Telemedicine in Critical Care: Problems in Design, Implementation, and Assessment, Critical Care Medicine, Jul. 1982, vol. 10, No. 7, 471-475.

Geraldine Fitzpatrick, TARDIS Evaluation: Report on Final Usage Evaluation of the TARDIS Telehealth System, Jul. 24, 1998, Issue No. 1.0.

Abstract Marie Delima, R.N., M. Michael Shabot, M.D., FACS, FCCM, FACMI, Karen Morris, R.N, Janet Mould, R.N., Eden Torre-Javier, R.N., Mark Lobue, B.A. and Jeannie Chen, Pharm.D., Successful Implementation of a Multiple-ICU Clinical Information System in a Tertiary Care Medical Center.

Xin Li, Daniel J. Valentino, George J. So, Robert Lufkin, Ricky K. Taira, A World Wide Web Telemedicine System, SPIE vol. 2711, 427-439.

Stephen M. Ayres, M.D., F.C.C.M., Ake Grenvik, M.D., Ph.D., F.C. C.M., Peter R. Holbrook, M.D., F.C.C.M., William C. Shoemaker, M.D., F.C.C.M., Textbook of Critical Care, 3rd Edition, 1995, Harcourt Brace & Company.

Karen B. Tate, PH.D., Reed M. Gardner, PH.D., Kurt Scherting, Nurses, Pagers, and Patient-Specific Criteria; Three Keys to Improved Critical Value Reporting, 1995, 164-168, AMIA, Inc.

Karen E. Tate, Ph.D., Reed M. Gardner, Ph.D., Computers, Quality, and the Clinical Laboratory: A Look at Critical Value Reporting, 17th Annual Symposium on Computer Applications in Medical Care, Oct. 30-Nov. 3, 1993, 193-197.

Peter J. Haug, Reed M. Gardner, Karen E. Tate, R. Scott Evans, Thomas D. East, Gilad Kuperman, T. Allan Pryor, Stanley M. Huff, and Homer R. Warner, Decision Support in Medicine: Examples from the HELP System, Computers and Biomedical Research 27, 1994, 396-418.

Thomas D. East, Ph.D., C. Jane Wallace, R.N., M.S., Alan H. Morris, M.D., Reed M. Gardner, Ph.D., and Dwayne R. Westenskow, Ph.D., Computers in Critical Care, New Technologies in Critical Care, Jun. 1995, vol. 7, No. 2, 203-216.

Reed M. Gardner, Ph.D., Bette B. Maack, R.R.A., R. Scott Evans, Ph.D., and Stanley M. Huff, M.D., Computerized Medical Care: The HELP System at LDS Hospital, Journal of AHIMA, Jun. 1992, 63(6):68-78.

Reed M. Gardner, Ph.D., Integrated Computerized Records Provide Improved Quality of Care with Little Loss of Privacy, Journal of the AMIA, Jul./Aug. 1994, vol. 1, No. 4, 320-322.

S Reddy, M Niewiadomska-Bugaj, Y V Reddy, H C Galfalvy, V Jagannathan, R Raman, K. Srinivas, R. Shank, T. Davis, S. Friedman, MD, B. Merkin, MD, M. Kilkenny,MD, Experience with ARTEMIS—An Internet-Based Telemedicine System, AMIA, 1997, 759-763.

Patrick R. Norris, M.S., Benoit M Dawant, Ph.D., Antoine Geissbuhler, M.D., Web-Based Data Integration and Annotation in the Intensive Care Unit, 1997.

H. C. Galfalvy, M.S., S. M. Reddy, Ph.D., M. Niewiadomska-Bugaj, Ph.D., S. Friedman, M.D., Evaluation of Community Care Network (CNN) System in a Rural Health Care Setting, 1995, AMIA Inc., 698-702.

K. Major, M. Shabot, S. Cunneen, Wireless Critical Alerts and Patient Outcomes in the Surgical Intensive Care Unit; The American Surgeon, 2000; p. 1057-1060.

M. Shabot, M. Lobue, Cedars-Sinai Medical Center Critical Alerting System, Feb. 2004; p. 1-16.

Shabot MM, LoBue M, Leyerle BJ, Dubin SB. Inferencing strategies for automated Alerts on critically abnormal laboratory and blood gas data, SCAMC 1989; 13:54-57.

APACHE® III Equation Update (Version III-J) 2002, pp. 1-22.
APACHE® III Equation Update (Version III-I) 2003, pp. 1-13.

O. Kostopoulau, M. Wildman, Sources of Variability in Uncertain Medical Decisions In the ICU: A Process Tracing Study, Qual. Saf. Health Care 2004, 13:272-280.

A. Seiver, Critical Care Computing: Past, Present, and Future; Critical Care Clinics, vol. 16, No. 4, Oct. 2000, pp. 1-17.

J. Fisher, S. Harbarth, A. Agthe, A. Benn, S. Ringer, D. Goldmann, and S. Fancani, Quantifying Uncertainty: Physicians' Estimates of Infection in Critically Ill Neonates and Children; Clinical Infection Diseases 2004:38, pp. 1383-1390.

N. Halpern, S. Pastores, R. Greenstein, Critical Care Medicine in the United States 1985-2000: An Analysis of Bed Numbers, Use, and Cost; Critical Care Medicine 2004, vol. 32, No. 6, pp. 1254-1259.

J.Mrus, Getting Beyond Diagnostic Accuracy: Moving Toward Approaches That Can Be Used in Practice; Clinical Infectious Diseases 2004:38, pp. 1391-1393.

B. Leyerle, M. Shabot, Integrated Computerized Databases for Medical Data Management Beyond the Bedside, International Journal of Clinical Monitoring and Clinical Computing 1990:7, pp. 83-89.

M.Shabot, M. Lobue, B. Leyerle, S. Dubin, Decision Support Alerts For Clinical Laboratory and Blood Gas Data, Int. J. Clinical Monitoring and Computing 1990:7, pp. 27-31.

M. Shabot, M. Lobue, Real-Time Wireless Decision Support Alerts on a Palmtop PDA; Proc. Ann. Symp. Compt Appl. Med Care 1995, pp. 174-179.

G. Kuperman, D. Sittig, M. Shabot, J.Teich, Clinical Decision Support for Hospital and Critical Care, pp. 174-179.

W. Bates, M. Cohen, L. Leape, J. Overhage, M. Shabot, T. Sheridan, Reducing the Frequency of Errors in Medicine, J. American Medical Informatics Assn. 2001:8 pp. 299-308.

M. Shabot, B. Leyerle, M. Lobue, Automatic Extraction of Intensity Intervention Scores From A Computerized Surgical ICU Flowsheet, Am. J. Surg 1987:154:1, pp. 72-76.

Terry Ann Capuano, et al., Remote Telemetry, Nursing Management, Vo. 26, No. 7, Jul. 1995.

Valeriy Nenov and John Klopp, Remote Access to Neurosurgical ICU Physiological Data using the World Wide web, health Care in the Information Age, 1996, pp. 242-249.

Betty L. Grundy, et al., Telemedicine in Critical Care: An Experiment in Health Care Delivery, JACEP, vol. 6, Oct. 1977, pp. 439-444.

Susan L. Mabry, et al., Integrated Medical Analysis System, Proceedings of the 1997 Winter Simlation Conferece,, 1997, pp. 1163-1168.

Simon M. Kaplan and Geraldine Fitzpatrick, Designing Support for Remote Intensive-Care Telehealth Using the Locales Framework, ACM, 1997, pp. 173-184.

Douglas A. Perednia, Telemedine Technology and Clinical Applications, JAMA, vol. 6, Feb. 8, 1995.

Silvia Miksch,Artificial Intelligence for Decision Support: Needs, Possibilities, and Limitations in ICU, 10th Postgraduate Cousre in Critical Care Medicine A.P.I.C.E. '95, Springer, 1995, pp. 1-11.

Ho Sung Lee, et al., Remote Patient Monitoring Service through World-Wide Web, Proceedings—19th International Conference-IEEE/EMBS Oct. 30-Nov.2, 1997 Chicago, IL. USA.

Doctors use 'remote control' to monitor ICU patients, CNN.com. technology>computing, Aug. 21, 2000, http://www.cnn.com/2000/TECH/computing/08/21/icu.t_t/index.html.

Finding Value in Intensive Care, From Afar, The New York Times on the Web, Jul. 27, 1999, www.Visicu.com/press/news/storyItem117.html.

Remote Monitoring of ICU Patients Lowers Mortality Rates, Complications, Johns Hopkins Newsrelease, Mar. 20, 2001, http://www.newswise.com/p/articles/view/23099/.
Brian A. Rosenfeld, M.D., FCCM, FCCP, et al., Intensive care unit telemedicine: Alternate paradigm for providing continuous intensivist care, Critical Care Medicine, vol. 28, No. 12, 2000 p. 3925-3931.
Benjamin Berg, Dale Vincent, and Donald Hudson, Remote Critical Care Consultation: Telehealth Projection of Clinical Specialty Expertise, Tripler Army Medical Center, Honolulu.
Xin Li, et al., A World Wide Web Telemedicine System, SPIE vol. 2711 p. 427-439.
Guidelines for Intensive Care Unit Design, Critical Care Medicine, Mar. 1995; 23(3):582-588.
Michael Breslow, et al., Effect of a Multiple-Site Intensive Care Unit Telemedicine Program on clinical and Economic Outcomes: An Alternative Paradigm for Intensivist Staffing, Critical Care Medicine 2004 vol. 32, No. 1.
Richard Brilli, et al., Critical care Delivery in the Intensive Care Unit: Defining Clinical Roles and the Best Practice Model, Critical Care Medicine 2001 vol. 29, No. 10.
M. Michael Shabot, et al., Decision Support Systems in Critical Care, 1994, Springer-Verlag Publishing, New York.
Rosenfeld, et al. Intensive care unit telemedicine: alternate paradigm for providing continuous intensivist care, Dec. 28, 2000, www.ncbi.nlm.nih.gov.
Definitions of Intensive Care Unit (ICU) on the Web, Apr. 2004, www.google.com and other websites.
Grundy, Betty Lou; Jones, Paul; Lovitt, Ann; "Telemedicine in critical care: Problems in design, implementation and assessment" Jul. 1982. Critical Care Medicine vol. 10, No. 7.
Heterington, Laurel Traynowicz; "High tech meets high tough: telemedicine's contribution to patient wellness"; Spring, 1998; Nursing Administration Quarterly, vol. 22, No. 3.
Summary of iMDSoft, LTD's Counterclaims—Filed Dec. 10, 2007.
Response to Summary of iMDSoft, LTD's Counterclaims—Filed Dec. 28, 2007.
Complaint And Request For Declaratory Judgment (Nov. 12, 2004).
First Amended Complaint And Request for Declaratory Judgment (Oct. 10, 2005).
Visicu, Inc.'s Answer, Affirmative Defenses, And Counterclaims With Respect To Cerner Corporation's First Amended Complaint And Request For Declaratory Judgment (Oct. 23, 2005).
Cerner Corporation's Reply To Visicu, Inc.'s Counterclaims (Nov. 28, 2005).
Visicu, Inc.'s First Amended Answer, Affirmative Defenses, And Counterclaims With Respect To Cerner Corporation's First Amended Complaint And Request For Declaratory Judgment (Dec. 27, 2007).
U.S. Patent 6,804,656 First Reexamination Certificate Issued Sep. 26, 2006 (Dec. 27, 2007).
U.S. Patent 6,804,656 Second Reexamination Certificate Issued Oct. 30, 2007 (Dec. 27, 2007).
Cerner Corporation's Second Amended Complaint And Request For Declaratory Judgment And Reply To Visicu, Inc..'s First Amended Answer, Affirmative Defenses, And Counterclaims.
Affidavit of Dr. Michael Berman.
Visicu, Inc.'s Answer, Affirmative Defenses, And Counterclaims With Respect To Cerner Corporation's Second Amended Complaint And Request For Declaratory Judgment (Jan. 21, 2008).
Cerner Corporation's Third Amended Complaint And Request For Declaratory Judgment And Reply To Visicu, Inc.'s First Amended Answer, Affirmative Defenses, And Counterclaims (May 15, 2009).
510(k) Summary of Safety and Effectiveness( May 15, 2009).
Cerner Corporation's Fourth Amended Complaint And Request For Declaratory Judgment And Reply To Visicu, Inc.'s First Amended Answer. Affirmative Defenses, And Coounterclaims (Jul. 28, 2009).
Visicu, Inc.'s Answer, Affirmative Defenses And Counterclaims With Respect To Cerner Corporation's Third Amended Complaint And Request For Declaratory Judgment (Jun. 4, 2009).
Cerner Corporation's Reply to Visicu, Inc.'s Counterclaims (Jun. 22, 2009).
Visicu, Inc.'s Answer, Affirmative Defenses And Counterclaims With Respect To Cerner Corporation's Fourth Amended Complaint And Request For Declaratory Judgment (Jul. 29, 2009).
Expert Report of Molly Joel Coye, MD.
Coye, Exhibit 1.
Coye, Exhibit 2.
Coye, Exhibit 3.
Coye, Exhibit 4.
Coye, Exhibit 5.
Expert Report of Susan Goran.
Goran Exhibit 1.
Expert Report of Gerald Mossinghoff.
Initial Expert Report of Charles Safran, MD.
Safran, Initial Exhibit A.
Safran, Initial Exhibit B.
Safran, Initial Exhibit C.
Safran, Initial Exhibit D.
Safran, Initial Exhibit E.
Safran, Initial Exhibit F.
Safran, Initial Exhibit G.
Safran, Initial Exhibit H.
Safran, Initial Exhibit I.
Safran, Initial Exhibit J.
Safran, Initial Exhibit K.
Safran, Initial Exhibit L.
Supplemental Expert Report of Charles Safran, MD.
Safran, Supplemental Exhibit A.
Second Expert Report of Steven Henkind, MD.
Henkind, Appendix A.
Henkind, Appendix B.
Henkind, Appendix C.
Paul D. Clayton, et al. "Decision Support In Healthcare." International Journal of Bio-Medical Computing 39, 1995: pp. 59-66.
Gilad J. Kuperman M.D., et al. "Detecting Alerts, Notifying Physician, & Offering Action Items: A Comprehensive Alerting System." Center for Applied Medical Information Systems Research, Brigham & Women's Hospital, Boston, MA; pp. 704-708.
Tsien, Christine L., "TrendFinder: Automated Detection of Alarmable Trends", Department of Electrical Engineering and Computer Science, Massachusetts Institute of Technology, Massachusetts; Jun. 2000.
Hosseinzadeh, Abolfazl, "A Rule-Based System for Vital Sign Monitoring in Intensive Care", Department of Electrical Engineering, McGill University, Montreal; Nov. 1993.
Aukburg, S.J. et al., "Automation of Physiological Data Presentation and Alarms in the Post Anesthesia Care Unit." In Symposium on Computer Applications in Medical Care, Nov. 5-8, 1989, Washington, DC; pp. 580-582.
Benis, A. M. et al., "Improved Detection of Adverse Cardiovascular Trends with the Use of a Two-Variable Computer Alarm" *Critical Care Medicine*, vol. 8, No. 2, Jun. 1980: 341-344.
Bierman, M. I. et al., "Pulse Oximetry in the Postoperative Care of Cardiac Surgical Patients; A Randomized Controlled Trial." *Chest*, vol. 102, No. 5, Nov. 1992: 1367-1370.
Bradshaw, K. E., "Computerized Alerting System Warns of Life-Threatening Events." In Symposium on Computer Application in Medical Care, Oct. 25-26, 1986, Washington, DC; pp. 403-409.
Chizeck, H. J., "Modeling, Simulation and Control in a Data Rich Environment." In Symposium on Computer Applications in Medical Care, Oct. 25-26, 1986, Washington, DC; pp. 65-69.
Coiera, E., "Intelligent Monitoring and Control of Dynamic Physiological Systems." *Artificial Intelligence in Medicine*, vol. 5, 1993: pp. 1-8.
Colvin, J. R. et al., "Microcomputer-Controlled Administration of Vasodilators Following Cardiac Surgery: Technical Considerations." J. *Cardiothoracic Anesthesia*, vol. 3, No. 1, Feb. 1989: pp. 10-15.
Coplin, W. M. et al., "Accuracy of Continuous Jugular Bulb Oximetry in the Intensive Care Unit." Neurosurgery, vol. 42, No. 3, Mar. 1998: 533-540.
Crew, A. D. et al., "Preliminary Clinical Trials of a Computer-Based Cardiac Arrest Alarm." Intensive Care Med, vol. 17, 1991: 359-364.
Garfinkel, D. et al., "PONI: An Intelligent Alarm System for Respiratory and Circulation Management in the Operating Rooms." In Symposium on Computer Applications in Medical Care, Nov. 6-9, 1988, Washington, DC; pp. 13-17.

Garfinkel D. et al., "Patient Monitoring in the Operating Room: Validation of Instrument Reading by Artificial Intelligence Methods." In Symposium on Computer Applications in Medical Care, Nov. 5-8, 1989, Washington, DC; pp. 575-579.

Guedes de Oliveira, P. et al., "The Role of Computer Based Techniques in Patient Monitoring: Technical Note." *Acta Neuorchir*, vol. 55, 1992 (Suppl.): 18-20.

Hahnel, J. et al., "Can a Clinician Predict the Technical Equipment a Patient will Need During Intensive Care Unit Treatment? An Approach to Standardize and Redesign the Intensive Care Unit Workstation." *J Clinical Monitoring*, vol. 8, No. 1, Jan. 1992: 1-6.

Hall, G. L. & P.B. Colditz, "Continuous Physiological Monitoring: An Integrated System for Use in Neonatal Intensive Care." *Australian Physical & Engineering Sciences in Medicine*, vol. 18, No. 3, 1995; 139-142.

Hayes-Roth, B. et al., "Guardian: An Experimental System for Intelligent ICU Monitoring." In Symposium on Computer Applications in Medical Care, Nov. 5-9, 1994, Washington, DC; p. 1004.

Irazuzta, Jose, "Monitoring in Pediatric Intensive Care." *Indian J. Pediatrics*, vol. 60, 1993: 55-65.

Jans, R et al., "A Low Cost ECG Central Station for Intensive Care." *Australian Physical & Engineering Sciences in Medicine*, vol. 13, No. 1, 1990: 31-35.

Jastremski, M. et al., "A Model for Technology Assessment as Applied to Closed Loop Infusion Systems" *Critical Care Medicine*, vol. 23, No. 10, Oct. 1995: 1745-1755.

Klass, M. A. & E. Y. Cheng, "Early Response to Pulse Oximetry Alarms with Telemetry." *J. Clinical. Monitoring*, vol. 10, No. 3, May 1994: 178-180.

Koski, E. M. J. et al., "A Knowledge-Based Alarm System for Monitoring Cardiac Operated Patients—Assessment of Clinical Performance." *International J Clinical Monitoring and Computing*, vol. 11, 1994: 79-83.

Koski, E. M. J. et al., "Development of an Expert System for Haemodynamic Monitoring: Computerized Symbolism of On-Line Monitoring Data." *International J. Clinical Monitoring and Computing*, vol. 8, 1992: 289-293.

Laffel, G. et al., "Using Control Charts to Analyze Serial Patient-Related Data." *Quality Management in Health Care*, vol. 3, No. 1, Fall 1994: 70-77.

L'Estrange, P. R. et al., "A Microcomputer System for Physiological Data Collection and Analysis." *Australian Dental Journal*, vol. 3 8, No. 5, Oct. 1993: 400-405.

M. de Beer, N. A. et al., "Clinical Evaluation of a Method for Automatic Detection and Removal of Artifacts in Auditory Evoked Potential Monitoring." *J Clinical Monitoring*, vol. 11, No. 6, Nov. 1995: 381-391.

Makivirta, A. et al., "The Median Filter as a Preprocessor for a Patient Monitor Limit Alarm System in Intensive Care." *Computer Methods and Programs in Biomedicine*, vol. 34, No. 2/3, Feb./Mar. 1991: 139-144.

Makivirta, A. & E. M. J. Koski, "Alarm-Inducing Variability in Cardiac Postoperative Data and the Effects of Prealarm Delay." Critical Care Medicine, vol. 8, No. 6, May 1994: 153-162.

Martin, J. F., "Closed-Loop Control of Arterial Pressure During Cardiac Surgery." *J. Clinical Monitoring*, vol. 8, No. 3, Jul. 1992: 252-253.

Meyer, C., "Visions of Tomorrow's ICU." *American J. Nursing*, Apr. 1993: 27-31.

Nenov, V. I. et al., "Computer Applications in the Intensive Care Unit." *Neurosurgery Clinics of North America*, vol. 5, No. 4, Oct. 1994: 811-827.

Nobel, J. J., "Physiologic Monitoring Systems, Acute Care." *Pediatric Emergency Care*, vol. 8, No. 4, Aug. 1992: 235-237.

Orr, J. A. & Westenskow, D. R, "A Breathing Circuit Alarm System Based on Neural Networks." *J. Clinical Monitoring*, vol. 10, No. 2, Mar. 1994: 101-109.

Pappert, D. et al., "Preliminary Evaluation of a New Continuous Intra-Arterial Blood Gas Monitoring Device." *Acta Anaesthesiologica Scandinavica*, Suppl. 107, Vol. 39, 1995: 67-70.

Rampil, I. J., "Intelligent Detection of Artifact." *The Automated Anesthesia Record and Alarm Systems*, Chapter 17, 1987: 175-190.

Runciman, W. B. et al., "The Pulse Oximeter: Applications and Limitations—An Analysis of 2000 Incident Reports." *Anaesthesia and Intensive Care*, vol. 2 1, No. 5, Oct. 1993: 543-550.

Sailors, R. M., "A Model-Based Simulator for Testing Rule-Based Decision Support Systems for Mechanical Ventilation of ARDS Patients." In Symposium on Computer Applications in Medical Care, Nov. 5-9, 1994, Washington, DC; p. 1007.

Sanklecha, M., "The Pulse Oximeter." *Indian J. Pediatrics*, vol. 60, No. 3, 1993: 469-470.

Schnapp, L. M. & N. J. Cohen, "Pulse Oximetry; Uses and Abuses." *Chest*, vol. 98, No. 5, Nov. 1990: 1244-1250.

Simpson, R. L., "Automating the ICU: Facing the Realities." *Nursing Management*, vol. 23, No. 3, Mar. 1992: 24-26.

Sittig, D. F. & M. Factor, "Physiological Trend Detection and Artifact Rejection: A Parallel Implementation of a Multi-State Kalman Filtering Algorithm." In Symposium on Computer Applications in Medical Care, Nov. 5-8, 1989, Washington, DC; pp. 569-574.

Stoodley, K. D. C. et al., "Problems in the Development of a Computerized Ward Monitoring System for a Pediatric Intensive Care Unit." *International J Clinical Monitoring and Computing*, vol. 8, 1992: 281-287.

Sukavaara, T. et al., "A Knowledge-based Alarm System for Monitoring Cardiac Operated Patients—Technical Construction and Evaluation." *International J. Clinical Monitoring and Computing*, vol. 10, 1993: 117-126.

Szaflarski, N. L., "Emerging Technology in Critical Care: Continuous Intra-Arterial Blood Gas Monitoring." *American J. Critical Care*, vol. 5, No. 1, Jan. 1996: 55-65.

Uckun, S., "Intelligent Systems in Patient Monitoring and Therapy Management." *International J. Clinical Monitoring and Computing*, vol. 11, 1994: 241-253.

Webb, R. K., "Medical Decision Making and Decision Analysis." *Anesthesia and Intensive Care*, vol. 16, No. 1, Feb. 1988: 107-109.

Yien, H. et al., "Spectral Analysis of Systemic Arterial Pressure and Heart Rate Signals as a Prognostic Tool for the Prediction of Patient Outcome in the Intensive Care Unit." *Critical Care Medicine*, vol. 25, No. 2, 1997: 258-266.

Tsien, Christine L. and James Fackler, "Poor Prognosis for Existing Monitors in the Intensive Care Unit" *Critical Care Medicine*, vol. 25, No. 4, 1997: 614-619.

Tsien, Christine L., "Reducing False Alarms in the Intensive Care Unit: A Systematic Comparison of Four Algorithms" Proceedings *AMIA* Symposium, 1997. pp. 9-14 (unnumbered).

Tsien, Christine L. "Reducing False Alarms in the Intensive Care Unit: A Systematic Comparison of Four Algorithms" Proceedings Annual *AMIA* Fall Symposium (1997), p. 894.

Tsien, Christine L. and James C. Fackler "An Annotated Data Collection System to Support Intelligent Analysis of Intensive Care Unit Data." Proceedings of the Second International Symposium on Advances in Intelligent Data Analysis, Reasoning about Data; Aug. 4-6, 1997; X. Liu, P. R, Cohen, and M. R, Berthold, Eds.; Springer-Verlag, London, UK; pp. 111-121.

Zhao, Ruilin, "A Model-Based Expert System for Interpretation of Hemodynamic Data from ICU Patients." Department of Electrical Engineering and Computer Science, Massachusetts Institute of Technology, May 18, 1997 (pp. 1-121).

Tsien, C.L. and Fackler, J.C., "Poor prognosis for existing monitors in the intensive care unit," Critical Care Medical Journal, vol. 25, No. 4 (1997) (p. 614-619).

Tsien, C.L. "Reducing False Alarms in the Intensive Care Unit: A Systematic Comparison of Four Algorithms," Proceedings Annual AMIA Fall Symposium (1997).

Kohane, I.S. and Haimowitz, I.J., "Hypothesis-Driven Data Abstraction with Trend Templates," Proceedings Annual AMIA Symposium on Computer Applications in Medical Care (1994), (p. 444-448).

Exhibit M, Initial Export Report of Charles Safran, M.D. Declaration of Ido Schoenberg. Submitted in *Corner Corporation v. VISICU, Inc.*, Case No. Apr. 1033-CV-W-GAF, U.S. District Court for the Western District of Missouri (Western Division).

Exhibit 2 to Exhibit M, Initial Expert Report of Charles Safran, M.D. Beta Evaluation and Development of the iMDSoft (Metavision) Critical Workstation Evaluation at the Massachusetts General Hospital, Aug. 1996-Sep. 1997. Submitted in *Corner Corgoration v.*

*VISICU, Inc.*, Case No. Apr. 1033-CV-W- GAF, U.S. District Court for the WeStern District of Missouri (Western Division).
[Previously Submitted] Initial Expert Report of Charles Safran, M.D. *Cerner Corporation* v. *VISICU Inc.*, Case No. Apr. 1033-CV-W-GAF, U.S. District Court for the Western District of Missouri (Western Division). Mar. 26, 2009. 95 pages.
[Previously Submitted] Exhibit M, Initial Expert Report of Charles Safran. Declaration of Ido Schoenberg. Submitted in *Cerner Corporation* v. *VISICU, Inc.*, Case No. Apr. 1033-CV-W-GAF, U.S. District Court for the Western District of Missouri (Western Division).
[Previously Submitted] Exhibit 1 to Exhibit M, Initial Expert Report of Charles Safran. U.S. Patent 6,322,502 to Schoenberg et al. Submitted in *Cerner Corporation* v. *VISICU, Inc.*, Case No. Apr. 1033-CV-W-GAF, U.S. District Court for the Western District of Missouri (Western Division).
[Previously Submitted] Exhibit 2 to Exhibit M, Initial Expert Report of Charles Safran. Beta Evaluation and Development of the iMDSoft (Metavision) Critical Workstation Evaluation at the Massachusetts General Hospital, Aug. 1996-Sep. 1997. Submitted in *Cerner Corporation* v. *VISICU, Inc.*, Case No. Apr. 1033-CV-W-GAF, U.S. District Court for the Western District of Missouri (Western Division).
[Previously Submitted] Exhibit 3 to Exhibit M, Initial Expert Report of Charles Safran. International Patent Publication WO 98/29790 to Imd Soft Ltd. Submitted in *Cerner Corporation* v. *VISICU, Inc.*, Case No. Apr. 1033-CV-W-GAF, U.S. District Court for the Western District of Missouri (Western Division).
Exhibit 4 to Exhibit M, Initial Expert Report of Charles Safran. "MetaVision: Proposal for Critical Care Clinical Information System." iMDSoft document, Mar. 21, 1997. 32 pp.. Submitted in *Cerner Corporation* v. *VISICU, Inc.*, Case No. Apr. 1033-CV-W-GAF, U.S. District Court for the Western District of Missouri (Western Division).
Exhibit 5 to Exhibit M, Initial Expert Report of Charles Safran. "Design—Smart Alarms Module." iMDSoft, Jan. 25, 1998. Submitted in *Cerner Corporation* v. *VISICU, Inc.*, Case No. Apr. 1033-CV-W-GAF, U.S. District Court for the Western District of Missouri (Western Division).
Exhibit 6 to Exhibit M, Initial Expert Report of Charles Safran. iMDSoft Product Brochure about MetaVision. Submitted in *Cerner Corporation* v. *VISICU, Inc.*, Case No. Apr. 1033-CV-W-GAF, U.S. District Court for the Western District of Missouri (Western Division).
Exhibit 7 to Exhibit M, Initial Expert Report of Charles Safran. Fax from M. Breslow to P. Gotlib, Dec. 17, 1997, regarding work agreement between ICCM and iMDSoft. Submitted in *Cemer Corporation* v. *VISICU, Inc.*, Case No. Apr. 1033-CV-W-GAF, U.S. District Court for the Western District of Missouri (Western Division).
Exhibit 8 to Exhibit M, Initial Expert Report of Charles Safran. "iMDSoft Introduces MetaVision—a Cost-Effective ICU Patient Interactive System." PR Newswire, Feb. 18, 1997. Submitted in *Cemer Corporation* v. *VISICU, Inc.*, Case No. Apr. 1033-CV-W-GAF, U.S. District Court for the Western District of Missouri (Western Division).
Expert Report of Elisa D. Harvey, D.V.M., Ph.D. *Cerner Corporation* v. *VISICU, Inc.*, Case No. Apr. 1033-CV-W-GAF, U.S. District Court for the Western District of Missouri (Western Division). Jun. 26, 2009. 24 pages.
Exhibit A, Expert Report of Elisa D. Harvey. List of Materials Reviewed. 3 pages. Submitted in *Cerner Corporation* v. *VISICU, Inc.*, Case No. Apr. 1033-CV-W-GAF, U.S. District Court for the Western District of Missouri (Western Division).
Exhibit B, Expert Report of Elisa D. Harvey. Curriculum Vitae of Elisa Devorshak Harvey, D.V.M, Ph.D. 11 pages. Submitted in *Cerner Corporation* v. *VISICU, Inc.*, Case No. Apr. 1033-CV-W-GAF, U.S. District Court for the Western District of Missouri (Western Division).
Exhibit C, Expert Report of Elisa D. Harvey. Center for Devices and Radiological Health Office of Device Evaluation, Food and Drug Administration, U.S. Dept. of Health and Human Services. Guidance for Industry and Fda Staff, Class Ii Special Controls Guidance Document: Vascular and Neurovascular Embolization Devices. Dec. 29, 2004, 16 pages. Submitted in *Cerner Corporation* v. *VISICU Inc.*, Case No. Apr. 1033-CV-W-GAF, U.S. District Court for the Western District of Missouri (Western Division).
Exhibit D, Expert Report of Elisa D. Harvey. "Medical Devices: Premarket Approval." U.S. Food and Drug Administration website, http://www.fda.gov/MedicalDevices/DeviceRegulationandGuidance/HowtoMarketYourDevice/PremarketSubmissions/PremarketApprovalPMA /default.htm. Printed Jun. 17, 2009. Submitted in *Cerner Corporation* v. *VISICU, Inc.*, Case No. Apr. 1033-CV-W-GAF, U.S. District Court for the Western District of Missouri (Western Division).
Exhibit E, Expert Report of Elisa D. Harvey. "Medical Devices: Humanitarian Device Exemption." U.S. Food and Drug Administration website, http://www.fda.gov/MedicalDevices/DeviceRegulationandGuidanee/ Howto MarketYourDevice/PremarketSubmissions/HumanitarianDeviceExemption/default.htm. Printed Jun. 17, 2009. Submitted in *Cerner Corporation* v. *VISICU, Inc.*, Case No. Apr. 1033-CV-W-GAF, U.S. District Court for the Western District of Missouri (Western Division).
Exhibit F, Expert Report of Elisa D. Harvey. "Medical Devices: Premarket Notification (510k)." U.S. Food and Drug Administration website, http://www.fda.gov/MedicalDevices/DeviceRegulationandGuidance/HowtoMarketYourDevice/PremarketSubmissions/PremarketNotification 510k/default.htm. Printed Jun. 17, 2009. Submitted in *Cerner Corporation* v. *VISICU, Inc.*, Case No. Apr. 1033-CV-W-GAF, U.S. District Court for the Western District of Missouri (Western Division).
Exhibit G, Expert Report of Elisa D. Harvey. Chart: 510k "Substantial Equivalence" Decision-Making Process. Submitted in *Cerner Corporation* v. *VISICU, Inc.*, Case No. Apr. 1033-CV-W-GAF, U.S. District Court for the Western District of Missouri (Western Division).
Certificate of Service, Expert Report of David Kapaska, D.O. *Cerner Corporation* v. *VISICU, Inc.*, Case No. Apr. 1033-CV-W-GAF, U.S. District Court for the Western District of Missouri (Western Division). Jun. 26, 2009.
Expert Report of David Kapaska, D.O. *Cerner Corporation* v. *VISICU, Inc.*, Case No. Apr. 1033-CV-W-GAF, U.S. District Court for the Western District of Missouri (Western Division). Jun. 26, 2009. 103 pages.
Exhibit 1, Expert Report of David Kapaska. Curriculum Vitae of David Kapaska, D.O., MBA. Submitted in *Cerner Corporation* v. *VISICU, Inc.*, Case No. Apr. 1033-CV-W-GAF, U.S. District Court for the Western District of Missouri (Western Division).
Exhibit 2, Expert Report of David Kapaska. List of Materials Reviewed. Submitted in *Cerner Corporation* v. *VISICU, Inc.*, Case No. Apr. 1033-CV-W-GAFf, U.S. District Court for the Western District of Missouri (Western Division).
Exhibit 3, Expert Report of David Kapaska. Walsh, Jon C., and Lange, Paul. "Virtual Critical Care Overview: Cerner Health Conference 2007." (PowerPoint presentation) 65 pages. Submitted in *Cerner Corporation* v. *VISICU, Inc.*, Case No. 04-1033-CV-W-GAF, U.S. District Corut for the Western District of Missouri (Western Division)
Exhibit 4, Expert Report of David Kapaska. Chalfin, Donald. "The Benefit of Intensivists." CQ, Jul. 2007. Printed from website of Primary Critical Care Medical Group (PCCMG.com), May 12, 2009. Submitted in *Cerner Corporation* v. *VISICU, Inc.*, Case No. Apr. 1033-CV-W-GAF, U.S. District Court for the Western District of Missouri (Western Division).
[Previously Submitted] Exhibit 5, Expert Report of David Kapaska. Grundy, Betty L., et al. "Telemedicine in Critical Care: An Experiment in Health Care Delivery." Journal of the American College of Emergency Physicians, vol. 6, Issue 10, Oct. 1977, pp. 439-444. Submitted in *Cerner Corporation* v. *VISICU, Inc.*, Case No. Apr. 1033-CV-W-GAF, U.S. District Court for the Western District of Missouri (Western Division).
[Previously Submitted] Exhibit 6, Expert Report of David Kapaska. Rosenfeld, Brian A., M.D., et al. "Intensive Care Unit Telemedicine: Alternate Paradigm for Providing Continuous Intensivist Care." Crit. Care Med. 2000, vol. 28, No. 12, pp. 3925-3931. Submitted in *Cerner Corporation* v. *VISICU, Inc.*, Case No. Apr. 1033-CV-W-GAF, U.S. District Court for the Western District of Missouri (Western Division).

[Previously Submitted] Exhibit 7, Expert Report of David Kapaska. Grundy, Betty L., M.D., et al. "Telemedicine in Critical Care: Problems in Design, Implementation and Assessment." Crit. Care Med. 1982, vol. 10, No. 7, pp. 471-475. Submitted in *Cerner Corporation v. VISICU, Inc.*, Case No. Apr. 1033-CV-W-GAF, U.S. District Court for the Western District of Missouri (Western Division).

Exhibit 8, Expert Report of David Kapaska. Grigsby, Jim, Ph.D., and Sanders, Jim H., Ph.D. "Telemedicine: Where It Is and Where It's Going." Annals of Internal Medicine, vol. 129, No. 2, 15 Jul. 1998, pp. 123-127. v Submitted in *Cerner Corporation v. VISICU, Inc.*, Case No. Apr. 1033-CV-W-GAF, U.S. District Court for the Western District of Missouri (Western Division).

[Previously Submitted] Exhibit 9, Expert Report of David Kapaska. U.S. Patent 5,544,649, to David, et al. "Ambulatory Patient Health Monitoring Techniques Utilizing Interactive Visual Communication." Aug. 13, 1996. Submitted in *Cerner Corporation v. VISICU, Inc.*, Case No. Apr. 1033-CV-W-GAF, U.S. District Court for the Western District of Missouri (Western Division).

Exhibit 10, Expert Report of David Kapaska. Zawada, Edward T., Jr., et al. "Impact of an Intensive Care Unit Telemedicine Program on a Rural Health Care System." Postgraduate Medicine, vol. 121, Issue 3, May 2009, pp. 160-170. Submitted in *Cemer Corporation v. VISICU, Inc.*, Case No. Apr. 1033-CV-W-GAF, U.S. District Court for the Western District of Missouri (Western Division).

Exhibit 11, Expert Report of David Kapaska. Meredith, Christina, et al. "Are There Too Many Alarms in the Intensive Care Unit? an Overview of the Problems." Journal of Advanced Nursing, 1995, 21, pp. 15-20. Submitted in *Cerner Corporation v. VISICU, Inc.*, Case No. Apr. 1033-CV-W-GAF, U.S. District Court for the Western District of Missouri (Western Division).

Exhibit 12, Expert Report of David Kapaska. Chambrin, M.-C., et al. "Multicentric Study of Monitoring Alarms in the Adult Intensive Care Unit (ICU): A Descriptive Analysis." Intensive Care Med. (1999) 25: 1360-1366. Submitted in *Cerner Corporation v. VISICU, Inc.*, Case No. Apr. 1033-CV-W-GAF, U.S. District Court for the Western District of Missouri (Western Division).

[Previously Submitted] Exhibit 13, Expert Report of David Kapaska. Tsien, Christine S., MS, et al. "Poor Prognosis for Existing Monitors in the Intensive Care Unit." Crit. Care Med. vol. 25(4), Apr. 1997, pp. 614-619. Submitted in *Cerner Corporation v. VISICU, Inc.*, Case No. Apr. 1033-CV-W-GAF, U.S. District Court for the Western District of Missouri (Western Division).

Exhibit 14, Expert Report of David Kapaska. Chambrin, Marie-Christine. "Alarms in the Intensive Care Unit: How Can the No. Of False Alarms Be Reduced?" Critical Care Aug. 2001, vol. 5, No. 4, pp. 184-188. Submitted in *Cerner Corporation v. VISICU, Inc.*, Case No. Apr. 1033-CV-W-GAF, U.S. District Court for the Western District of Missouri (Western Division).

[Previously Submitted] Exhibit 15, Expert Report of David Kapaska. U.S. Patent 5,942,986, to Shabot, et al. "System and Method for Automatic Critical Event Notification." Aug. 24, 1999. Submitted in *Cerner Corporation v. VISICU Inc.*, Case No. Apr. 1033-CV-W-GAF, U.S. District Court for the Western District of Missouri (Western Division).

Exhibit 16, Expert Report of David Kapaska. Transcript of video deposition of Jon Walsh, M.D., Jan. 20, 2009. 79 pages, Submitted in *Cemer Corporation v. VISICU, Inc.*, Case No. Apr. 1033-CV-W-GAF, U.S. District Court for the Western District of Missouri (Western Division).

[Previously Submitted] Exhibit 17, Expert Report of David Kapaska. Transcript—Oral and video deposition of Michael Shabot, M.D. Feb. 11, 2009. 35 pages. Submitted in *Cerner Corporation v. VISICU, Inc.*, Case No. Apr. 1033-CV-W-GAF, U.S. District Court for the Western District of Missouri (Western Division).

Exhibit 18, Expert Report of David Kapaska. Moss, Marc, et al. "Differences in the Response Times of Pages Originating from the ICU." Chest 1999, 116, 1019-1024. Submitted in *Cerner Corporation v. VISICU Inc.*, Case No. Apr. 1033-CV-W-GAF, U.S. District Court for the Western District of Missouri (Western Division).

Exhibit 19, Expert Report of David Kapaska. Kuperman, Gilad J. et al. "How Promptly Are Inpatients Treated for Critical Laboratory Results?" Jamia 1998, 5:112-119. Submitted in *Cerner Corporation v. VISICU, Inc.*, Case No. Apr. 1033-CV-W-GAF, U.S. District Court for the Western District of Missouri (Western Division).

Exhibit 20, Expert Report of David Kapaska. Kuperman, Gilad J., et al. "Improving Response to Critical Laboratory Results With Automation: Results of a Randomized Controlled Trial." Jamia vol. 6, No. 6, pages. 512-522 (1999). Submitted in *Cerner Corporation v. VISICU, Inc.*, Case No. Apr. 1033-CV-W-GAF, U.S. District Court for the Western District of Missouri (Western Division).

Expert Report of Michael Sofocleous. *Cerner Corporation v. VISICU, Inc.*, Case No. Apr. 1033-CV-W-GAF, U.S. District Court for the Western District of Missouri (Western Division). Jun. 26, 2009. 40 pages.

Exhibit 1, Expert Report of Michael Sofocleous. Curriculum Vitae of Michael Sofocleous. Submitted in *Cerner Corporation v. VISICU, Inc.*, Case No. Apr. 1033-CV-W-GAF, U.S. District Court for the Western District of Missouri (Western Division).

Exhibit 2, Expert Report of Michael Sofocleous. List of Materials Reviewed. Submitted in *Cerner Corporation v. VISICU, Inc.*, Case No. Apr. 1033-CV-W-GAF, U.S. District Court for the Western District of Missouri (Western Division).

Expert Report of John Wade on Cumulativeness and Prior Art That Was Before the Patent Office. *Cerner Corporation v. VISICU, Inc.*, Case No. Apr. 1033-CV-W-GAF, U.S. District Court for the Western District of Missouri (Western Division). Jun. 26, 2009. 41 pp.

Exhibit L, Expert Report of John Wade. List of Materials Reviewed. *Cerner Corporation v. VISICU, Inc.*, Case No. Apr. 1033-CV-W-GAF, U.S. District Court for the Western District of Missouri (Western Division).

Exhibit M, Expert Report of John Wade. Chart comparing features described by Dr. Safran in Expert Reports with text from prior art references. 106 pages. *Cerner Corporation v. VISICU, Inc.* Case No. Apr. 1033-CV-W-GAF, U.S. District Court for the Western District of Missouri (Western Division).

Exhibit N, Expert Report of John Wade. Chart comparing VitalCom comparison chart from Visicu Premarket 510(k) Notification with Examiners' Search Report Excerpts from '656 Prosecution. 33 pages. *Cerner Corporation v. VISICU, Inc.*, Case No. Apr. 1033-CV-W-GAF, U.S. District Court for the Western District of Missouri (Western Division).

Exhibit 0, Expert Report of John Wade. References Reviewed by John Wade. *Cerner Corporation v. VISICU, Inc.*, Case No. Apr. 1033-CV-W-GAF, U.S. District Court for the Western District of Missouri (Western Division).

[Previously Submitted] Exhibit 01, Expert Report of John Wade. U.S. Patent 3,646,606 to Buxton, et al. Feb. 29, 1972. *Cerner Corporation v. VISICU, Inc.*, Case No. Apr. 1033-CV-W-GAF, U.S. District Court for the Western District of Missouri (Western Division).

[Previously Submitted] Exhibit 02, Expert Report of John Wade. U.S. Patent 4,838,275 to Lee. Jun. 13, 1989. *Cerner Corporation v. VISICU, Inc.*, Case No. Apr. 1033-CV-W-GAF, U.S. District Court for the Western District Inc., Case No. Apr. 1033-CV-W-GAF, U.S. District Court for the Western District Of Missouri (Western Division).

[Previously Submitted] Exhibit 03, Expert Report of John Wade. U.S. Patent 5,619,991 to Sloane. Apr. 15, 1997. *Cerner Corporation v. VISICU, Inc.*, Case No. Apr. 1033-CV-W-GAF, U.S. District Court for the Western District of Missouri (Western Division).

[Previously Submitted] Exhibit 04, Expert Report of John Wade. U.S. Patent 5,724,580 to Levin, et al. Mar. 3, 1998. *Cerner Corporation v. Visicu, Inc.*, Case No. Apr. 1033-CV-W-GAF, U.S. District Court for the Western District of Missouri (Western Division).

[Previously Submitted] Exhibit 05, Expert Report of John Wade. U.S. Patent 5,822,544 to Chaco, et al. Oct 13, 1998. *Cerner Corporation v. VISICU, Inc.*, Case No. Apr. 1033-CV-W-GAF, U.S. District Court for the Western District of Missouri (Western Division).

[Previously Submitted] Exhibit O6, Expert Report of John Wade. U.S. Patent 6,024,699 to Surwit, et al. Feb. 15, 2000. *Cerner Corporation v. VISICU, Inc.*, Case No. Apr. 1033-CV-W-GAF, U.S. District Court for the Western District of Missouri (Western Division).

[Previously Submitted] Exhibit O7, Expert Report of John Wade. U.S. Patent 6,230,142 to Benign, et al. May 8, 2001. *Cerner Corporation v. VISICU, Inc.*, Case No. Apr. 1033-CV-W-GAF, U.S. District Court for the Western District of Missouri (Western Division).

[Previously Submitted] Exhibit O8, Expert Report of John Wade. U.S. Patent 6,364,834 to Reuss, et al.. Apr. 2, 2002. *Cerner Corporation* v. *VISICU, Inc.*, Case No. Apr. 1033-CV-W-GAF, U.S. District Court for the Western District of Missouri (Western Division).

[Previously Submitted] Exhibit O9, Expert Report of John Wade. U.S. Patent 6,385,589 to Trusheim, et al. May 7, 2002. *Cemer Corporation* v. *VISICU, Inc.*, Case No. Apr. 1033-CV-W-GAF, U.S. District Court for the Western District of Missouri (Western Division).

[Previously Submitted] Exhibit O10, Expert Report of John Wade. Capuano, Terry Ann, et al. "Remote Telemetry: New Twists for Old Technology." Nursing Management, vol. 26, No. 7, pp. 26-32 (Jul. 1995). *Cerner Corporation* v. *VISICU, Inc.*, Case No. Apr. 1033-CV-W-GAF, U.S. District Court for the Western District of Missouri (Western Division).

Exhibit O11, Expert Report of John Wade. Capuano, Terry Aim, et al. "Remote Monitoring: Expanding a Successful System." Nursing Management, vol. 28, No. 5, pp. 40A-40D (1997). *Cerner Corporation* v. *VISICU, Inc.*, Case No. Apr. 1033-CV-W-GAF, U.S. District Court for the Western District of Missouri (Western Division).

[Previously Submitted] Exhibit O12, Expert Report of John Wade. Delima, Marie, et al. "Successful Implementation of a Multiple-ICU Clinical Information System in a Tertiary Care Medical Center." Depts. of Enterprise Information Services, Surgery, Medicine, and Pharmacy, Cedars-Sinai Health System, Los Angeles, California. *Cerner Corporation* v. *VISICU, Inc.*, Case No. Apr. 1033-CV-W-GAF, U.S. District Court for the Western District of Missouri (Western Division).

[Previously Submitted] Exhibit O13, Expert Report of John Wade. Leyerle, Beverley J., et al. "Integrated Computerized Databases for Medical Data Management Beyond the Bedside." Intl. Journal of Clinical Monitoring and Computing, 7: 83-89 (1990). *Cerner Corporation* v. *VISICU, Inc.*, Case No. Apr. 1033-CV-W-GAF, U.S. District Court for the Western District of Missouri (Western Division).

Exhibit O14, Expert Report of John Wade. Seiver, Adam. "Critical Care Computing: Past, Present, and Future." Critical Care Clinics, vol. 16, No. 4 (Oct. 2000). 17 pages. *Cerner Corporation* v. *VISICU, Inc.*, Case No. Apr. 1033-CV-W-GAF, U.S. District Court for the Western District of Missouri (Western Division).

[Previously Submitted] Exhibit O15, Expert Report of John Wade. Major, Kevin, et al. "Wireless Clinical Alerts and Patient Outcomes in the Surgical Intensive Care Unit." The American Surgeon, vol. 68, No. 12, pp. 1057-1060 (Dec. 2002). *Cerner Corporation* v. *VISICU, Inc.*, Case No. 04-1033-CV-W-GAF, U.S. District Court for the Western District of Missouri (Western Division).

[Previously Submitted] Exhibit O16, Expert Report of John Wade. Shabot, M. Michael, et al. "Real-Time Wireless Decision Support Alerts on a Palmtop PDA." Proc. AMIA (Jamia Suppl.) 1995; 19:174-77. *Cerner Corporation* v. *VISICU, Inc.*, Case No. Apr. 1033-CV-W-GAF, U.S. District Court for the Western District of Missouri (Western Division).

[Previously Submitted] Exhibit O17, Expert Report of John Wade. Shabot, M. Michael, et al. "Wireless Clinical Alerts for Physiologic, Laboratory and Medication Data." Proceedings Amia Annual Symposium (2000), pp. 789-793. *Cerner Corporation* v. *VISICU, Inc.*, Case No. Apr. 1033-CV-W-GAF, U.S. District Court for the Western District of Missouri (Western Division).

[Previously Submitted] Exhibit O18, Expert Report of John Wade. Shabot, M. Michael, et al. "Cedars-Sinai Medical Center Critical Alerting System." Cedars-Sinai Medical Center, Feb. 2004. *Cerner Corporation* v. *VISICU, Inc.*, Case No. Apr. 1033-CV-W-GAF, U.S. District Court for the Western District of Missouri (Western Division).

[Previously Submitted] Exhibit O19, Expert Report of John Wade. Nenov, Valeriy, et al. "Remote Access to Neurosurgical ICU Physiological Data Using the World Wide Web." in Health Care and the Information Age (H. Sieburg, S. Weghorst and K. Morgan, Eds.) IOS Press and Ohmsha, 1996, pp. 242-249. *Cerner Corporation* v. *VISICU, Inc.*, Case No. Apr. 1033-CV-W-GAF, U.S. District Court for the Western District of Missouri (Western Division).

Certificate of Service, Expert Report of Craig M. Lilly, M.D. *Cerner Corporation* v. *VISICU, Inc.*, Case No. Apr. 1033-CV-W-GAF, U.S. District Court for the Western District of Missour (Western Division). Jun. 26, 2009.

Expert Report of Craig M.Lilly, M.D. Submitted in *Cerner Corporation* v. *VISICU, Inc.*, Case No. 04-1033-CV-W-GAF, U.S. District Court for the Western District of Missiouri (Western Division). Jun. 26, 2009. 98 pages.

Exhibit 1, Expert Report of Craig Lilly. Curriculum Vitae of Craig M. Lilly. Submitted in *Cerner Corporation* v. *VISICU, Inc.*, Case No. Apr. 1033-CV-W-GAF, U.S. District Court for the Western District of Missouri (Western Division).

Exhibit 2, Expert Report of Craig Lilly. List of Materials Reviewed. Submitted in *Cerner Corporation* v. *VISICU, Inc.*, Case No. Apr. 1033-CV-W-GAF, U.S. District Court for the Western District of Missouri (Western Division).

Exhibit 3, Expert Report of Craig Lilly. *Future Needs in Pulmonary and Critical Care Medicine*. Report by Abt Associates Inc., Cambridge, MA, Nov. 13, 1998. 104 pages. Submitted in *Cerner Corporation* v. *VISICU, Inc.*, Case No. Apr. 1033-CV-W-GAF, U.S. District Court for the Western District of Missouri (Western Division).

[Abstract Previously Submitted] Exhibit 4, Expert Report of Craig Lilly. Angus, Derek C.; Kelley, Mark A.; Schmitz, Robert J., et al. "Current and Projected Workforce Requirements for Care of the Critically Ill and Patients With Pulmonary Disease: Can We Meet the Requirements of an Aging Population?" JAMA 284(21): 2762-2770 (2000). Submitted in *Cerner Corporation* v. *VISICU, Inc.*, Case No. Apr. 1033-CV-W-GAF, U.S. District Court for the Western District of Missouri (Western Division).

Exhibit 5, Expert Report of Craig Lilly. Kahn, Jeremy M., et al. "Barriers to Implementing the Leapfrog Group Recommendations for Intensivist Physician Staffing: A Survey of Intensive Care Unit Directors." Journal of Critical Care (2007) vol. 22, pp. 97-103. Submitted in *Cerner Corporation* v. *VISICU, Inc.*, Case No. Apr. 1033-CV-W-GAF, U.S. District Court for the Western District of Missouri (Western Division).

[Abstract Previously Submitted] Exhibit 6, Expert Report of Craig Lilly. Pronovost, Peter J.; Jenckes, Mollie W.; Dorman, Todd, et al. "Organizational Characteristics of Intensive Care Units Related to Outcomes of Abdominal Aortic Surgery." JAMA. 1999; 281(14): 1310-1317. Submitted in *Cerner Corporation* v. *VISICU, Inc.*, Case No. Apr. 1033-CV-W-GAF, U.S. District Court for the Western District of Missouri (Western Division).

Exhibit 7, Expert Report of Craig Lilly. Pingleton, Susan K. "Update on Compaccs." Editorial in Chest, vol. 110, No. 2, Aug. 1996, p. 307. Submitted in *Cerner Corporation* v. *VISICU, Inc.*, Case No. Apr. 1033-CV-W-GAF, U.S. District Court for the Western District of Missouri (Western Division).

[Previously Submitted] Exhibit 8, Expert Report of Craig Lilly. U.S. Patent 5,942,986 to Shabot, et al. Aug. 24, 1999. Submitted in *Cerner Corporation* v. *VISICU, Inc.*, Case No. Apr. 1033-CV-W-GAF, U.S. District Court for the Western District of Missouri (Western Division).

[Previously Submitted] Exhibit 9, Expert Report of Craig Lilly. Shabot, M. Michael, et al. "Wireless Clinical Alerts for Critical Medication, Laboratory and Physiologic Data." Proceedings of the 33$^{rd}$ I Hawaii International Conference on System Sciences, 2000. IEEE: 0/7695-0493-0/00. 6 pages. Submitted in *Cerner Corporation* v. *VISICU, Inc.*, Case No. Apr. 1033-CV-W-GAF, U.S. District Court for the Western District of Missouri (Western Division).

[Previously Submitted] Exhibit 10, Expert Report of Craig Lilly. Kuperman, Gilad J. et al. "How Promptly Are Inpatients Treated for Critical Laboratory Results?" JAMIA 1998, 5:112-119. Submitted in *Cerner Corporation* v. *VISICU, Inc.*, Case No. Apr. 1033-CV-W-GAF, U.S. District Court for the Western District of Missouri (Western Division).

[Previously Submitted] Exhibit 11, Expert Report of Craig Lilly. Kuperman, Gilad J., et al. "Improving Response to Critical Laboratory Results With Automation: Results of a Randomized Controlled Trial." JAMIA vol. 6, No. 6, pp. 512-522 (1999). Submitted in *Cerner Corporation* v. *VISICU, Inc.*, Case No. Apr. 1033-CV-W-GAF, U.S. District Court for the Western District of Missouri (Western Division).

[Previously Submitted] Exhibit 12, Expert Report of Craig Lilly. Chalfin, Donald. "The Benefit of Intensivists." CQ, Jul. 2007. Printed from website of Primary Critical Care Medical Group (PCCMG. com), May 12, 2009. Submitted in *Cerner Corporation* v. *VISICU, Inc.*, Case No. Apr. 1033-CV-W-GAF, U.S. District Court for the Western District of Missouri (Western Division).
Exhibit 13, Expert Report of Craig Lilly. Wachter, Robert M. "An Introduction to the Hospitalist Model." Annals of Internal Medicine, vol. 130, No. 4 (Part 2), pp. 338-342 (Feb. 16, 1999). Submitted in *Cerner Corporation* v. *VISICU, Inc.*, Case No. Apr. 1033-CV-W-GAF, U.S. District Court for the Western District of Missouri (Western Division).
[Abstract Previously Submitted] Exhibit 14, Expert Report of Craig Lilly. Hanson, C. William, III, et al. "Effects of an Organized Critical Care Service on Outcomes and Resource Utilization: A Cohort Study." Critical Care Medicine, vol. 27(2), Feb. 1999, pp. 270-274. Submitted in *Cerner Corporation* v. *VISICU, Inc.*, Case No. Apr. 1033-CV-W-GAF, U.S. District Court for the Western District of Missouri (Western Division).
Exhibit 15, Expert Report of Craig Lilly. Crippen, David. "Regionalization, Prioritization, and Sailing Ships in the Year 2010." New Horizons, vol. 7, No. 2, pp. 218-228 (Summer 1999). Submitted in *Cerner Corporation* v. *VISICU, Inc.*, Case No. Apr. 1033-CV-W-GAF, U.S. District Court for the Western District of Missouri (Western Division).
Exhibit 16, Expert Report of Craig Lilly. Thompson, Dan R., et al. "Regionalization of Critical Care Medicine: Task Force Report of the American College of Critical Care Medicine." Critical Care Medicine, vol. 22, No. 8, pp. 1306-1313 (Aug. 1994). Submitted in *Cerner Corporation* v. *VISICU, Inc.*, Case No. Apr. 1033-CV-W-GAF, U.S. District Court for the Western District of Missouri (Western Division).
[Previously Submitted] Exhibit 17, Expert Report of Craig Lilly, Grundy, Betty L., et al. "Telemedicine in Critical Care: An Experiment in Health Care Delivery." Journal of the American College of Emergency Physicians, vol. 6, Issue 10, Oct. 1977, pp. 439-444. Submitted in *Cerner Corporation* v. *VISICU, Inc.*, Case No. Apr. 1033-CV-W-GAF, U.S. District Court for the Western District of Missouri (Western Division).
[Previously Submitted] Exhibit 18, Expert Report of Craig Lilly. Grundy, Betty L., M.D., et al. "Telemedicine in Critical Care: Problems in Design, Implementation and Assessment." Crit. Care Med. 1982, vol. 10, No. 7, pp. 471-475. Submitted in *Cerner Corporation* v. *VISICU, Inc.*, Case No. Apr. 1033-CV-W-GAF, 'U.S. District Court for the Western District of Missouri (Western Division).
[Previously Submitted] Exhibit 19, Expert Report of Craig Lilly. Rosenfeld, Brian A., M.D., et al. "Intensive Care Unit Telemedicine: Alternate Paradigm for Providing Continuous Intensivist Care." Crit. Care Med. 2000, vol. 28, No. 12, pp. 3925-3931. Submitted in *Cerner Corporation* v. *VISICU, Inc.*, Case No. Apr. 1033-CV-W-GAF, U.S. District Court for the Western District of Missouri (Western Division).
[Previously Submitted] Exhibit 20, Expert Report of Craig Lilly. Grigsby, Jim, Ph.D., and Sanders, Jim H., Ph.D. "Telemedicine: Where It Is and Where It's Going." Annals of Internal Medicine, vol. 129, No. 2, 15 Jul. 1998, pp. 123-127. Submitted in *Cerner Corporation* v. *VISICU, Inc.*, Case No. Apr. 1033-CV-W-GAF, U.S. District Court for the Western District of Missouri (Western Division).
[Previously Submitted] Exhibit 21, Expert Report of Craig Lilly. U.S. Patent 5,544,649, to David, et al. "Ambulatory Patient Health Monitoring Techniques Utilizing Interactive Visual Communication." Aug. 13, 1996. Submitted in *Cerner Corporation* v. *VISICU, Inc.*, Case No. Apr. 1033-CV-W-GAF, U.S. District Court for the Western District of Missouri (Western Division).
Suggestions in Support of Cerner Corporation's Motion for Summary Judgment of Invalidity. *Cerner Corporation* v. *VISICU, Inc.*, Case No. Apr. 1033-CV-W-GAF, U.S. District Court for the Western District of Missouri (Western Division). Jul. 23, 2009. 33 pages.
Visicu, Inc.'s Suggestions in Support of Motion for Summary Judgment of no. Inequitable Conduct. *Cerner Corporation* v. *VISICU, Inc.*, Case No. Apr. 1033-CV-W-GAF, U.S. District Court for the Western District of Missouri (Western Division). Jul. 23, 2009. 51 pages.

Cover letter from J. Glidewell to D. Jones dated Aug. 17, 2009, enclosing copy of Charles Safran, M.D.'s Rebuttal Report. *Cerner Corporation* v. *VISICU, Inc.*, Case No. Apr. 1033-CV-W-GAF, U.S. District Court for the Western District of Missouri (Western Division).
Charles Safran, M.D.'s Rebuttal Report to Expert Report of John Wade on Cumulativeness and Prior Art That Was Before the Patent Office. *Cerner Corporation* v. *VISICU, Inc.*, Case No. Apr. 1033-CV-W-GAF, U.S. District Court for the Western District of Missouri (Western Division). Aug. 17, 2009. 14 pages.
[Previously Submitted] Exhibit a to Charles Safran, M.D.'s Rebuttal Report to Expert Report of John Wade on Cumulativeness and Prior Art That Was Before the Patent Office: Curriculum Vitae of Charles Safran. *Cerner Corporation* v. *VISICU, Inc.*, Case No. Apr. 1033-CV-W-GAF, U.S. District Court for the Western District of Missouri (Western Division).
[Previously Submitted] Exhibit B to Charles Safran, M.D.'s Rebuttal Report to Expert Report of John Wade on Cumulativeness and Prior Art That Was Before the Patent Office: Report of Scholarship. *Cerner Corporation* v. *VISICU, Inc.*, Case No. Apr. 1033-CV-W-GAF, U.S. District Court for the Western District of Missouri (Western Division).
Exhibit C to Charles Safran, M.D.'s Rebuttal Report to Expert Report of John Wade on Cumulativeness and Prior Art That Was Before the Patent Office: Table of Contents. *Cerner Corporation* v. *VISICU, Inc.*, Case No. Apr. 1033-CV-W-GAF, U.S. District Court for the Western District of Missouri (Western Division).
Cerner Corporation's Suggestions in Opposition to Viscu, Inc.'s Motion for Summary Judgment of No. Inequitable Conduct. *Cemer Corporation* v. *VISICU, Inc.*, Case No. Apr. 1033-CV-W-GAF, U.S. District Court for the Western District of Missouri (Western Division). Aug. 24, 2009. 52 pages.
VISICU, Inc.'s Suggestions in Opposition to Cerner Corporation's Motion for Summary Judgment of Invalidity. *Cerner Corporation* v. *VISICU, Inc.*, Case No. Apr. 1033-CV-W-GAF, U.S. District Court for the Western District of Missouri (Western Division). Aug. 24, 2009. 30 pages.
VISICU, Inc.'s Suggestions in Reply to Cerner Corporation's Opposition to Visicu, Inc.'s Motion for Summary Judgment of No Inequitable Conduct. *Cerner Corporation* v. *VISICU, Inc.*, Case No. Apr. 1033-CV-W-GAF, U.S. District Court for the Western District of Missouri (Western Division). Sep. 4, 2009. 38 pages.
Transcripts of Jury Trial, Nov. 16-20, 2009. *Cemer Corporation* v. *VISICU, Inc.*, Case No. Apr. 1033-CV-W-GAF, U.S. District Court for the Western District of Missouri (Western Division). 703 pages.
Transcripts of Jury Trial, Nov. 23-25, 2009. *Cerner Corporation* v. *VISICU, Inc.*, Case No. Apr. 1033-CV-W-GAF, U.S. District Court for the Western District of Missouri (Western Division). 569 pages.
Transcripts of Jury Trial, Nov. 30-Dec. 4, 2009. *Cerner Corporation* v. *VISICU, Inc.*, Case No. Apr. 1033-CV-W-GAF, U.S. District Court for the Western District of Missouri (Western Division). 969 pages.
Transcript of Jury Trial, Dec. 4, 2009, and Exhibit Index. *Cerner Corporation* v. *VISICU, Inc.*, Case No. Apr. 1033-CV-W-GAF, U.S. District Court for the Western District of Missouri (Western Division). 30 pages.
(625) Aug. 20, 2010 Cerner's Post Trial Brief.
(626 0) Sep. 9, 2010 Visicu's Response to Cerner's Post Trial Brief on Inequitable Conduct.
(626 3) Sep. 3, 2010 Appendix A to Visicu's Response to Cerner's Post Trial Brief on Inequitable Conduct.
(627)Sep. 10, 2010 Cerner's Proposed Findings of Fact.
(628) Sep. 14, 2010 Cerner's Proposed Findings of Fact and Conclusions of Law Regarding Inequitable Conduct.
(637) Oct. 28, 2010 Visicu's Motion for a New Trial.
(640 1) Oct, 28, 2010 Appendix to Visicu's Suggestions in Support of its Motion for Judgment as a Matter of Law on Infringement.
(640 2) Oct. 28, 2010 Appendix to Visicu's Suggestions in Support of its Motion for Judgment as a Matter of Law on Infringement.
(640 3)Oct. 28, 2010 Appendix to Visicu's Suggestions in Support of its Motion for Judgment as a Matter of Law on Infringement.
(641) Oct. 28, 2010 Cerner's Responses to Visicu's Proposed Findings of Fact and Conclusions of Law Regarding Inequitable Conduct.
(644 0) Nov. 10, 2010 Notice of Supplemental Authority.
(644 1) Nov. 10, 2010 Exhibit A to Notice of Supplemental Authority.

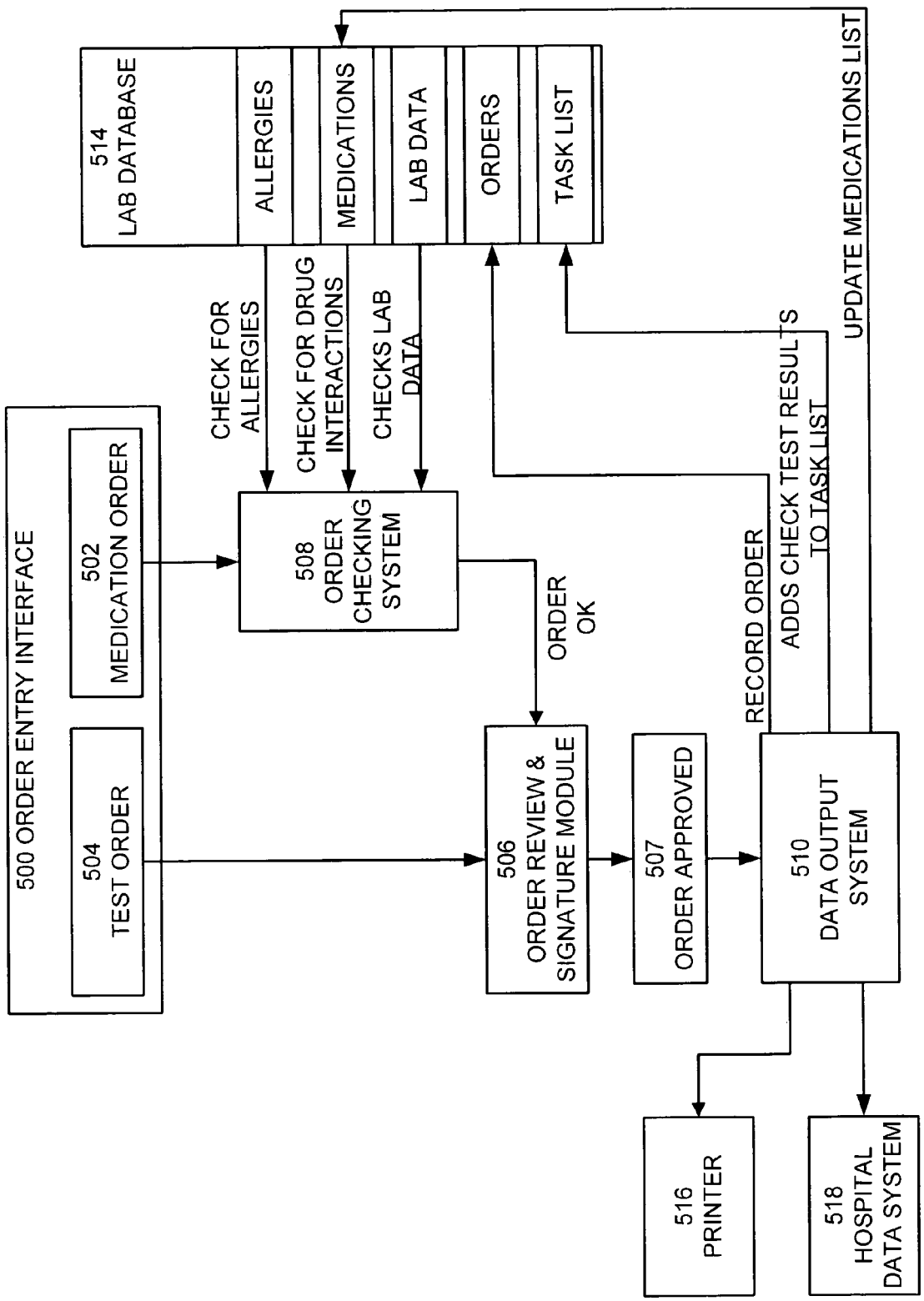

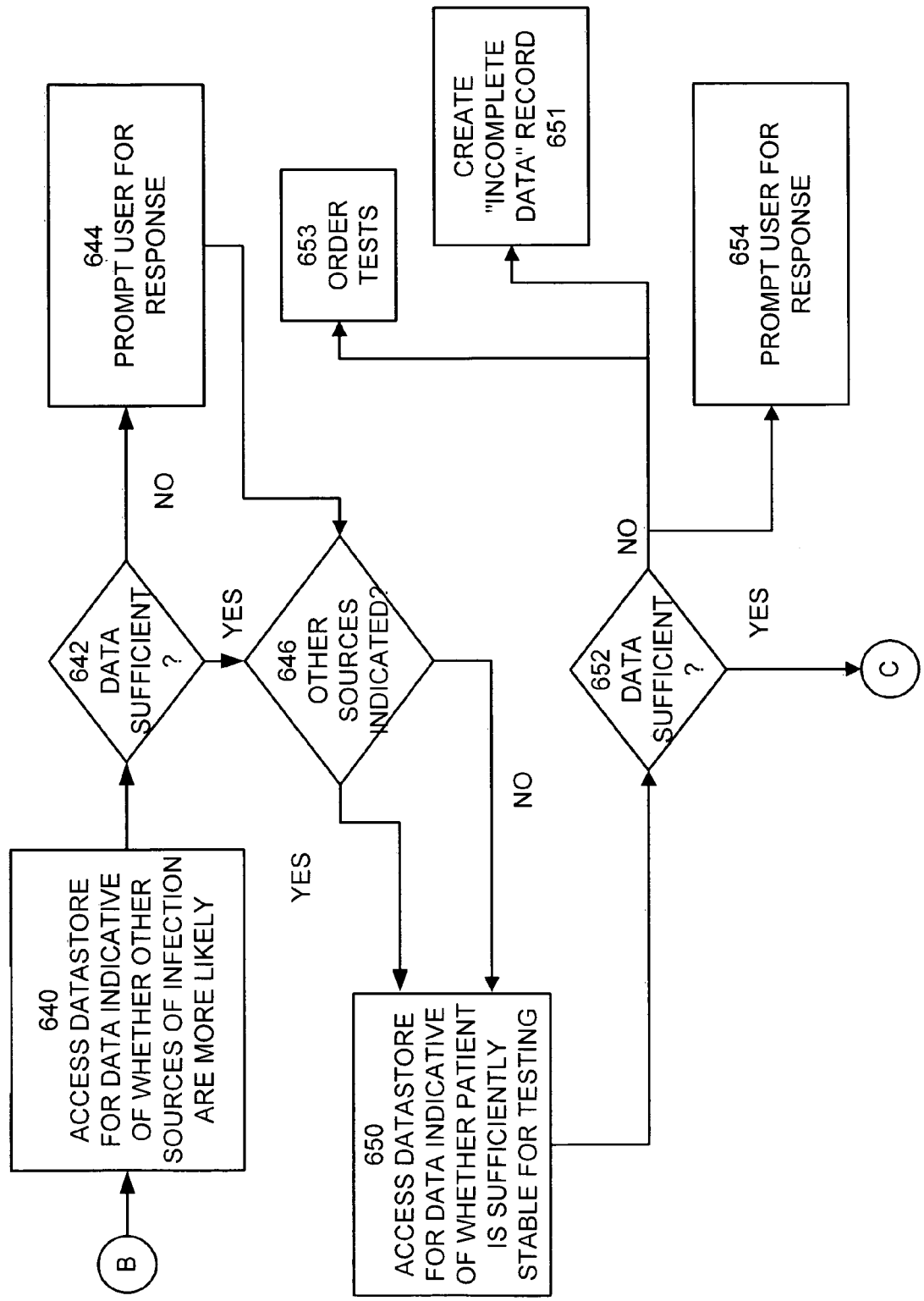

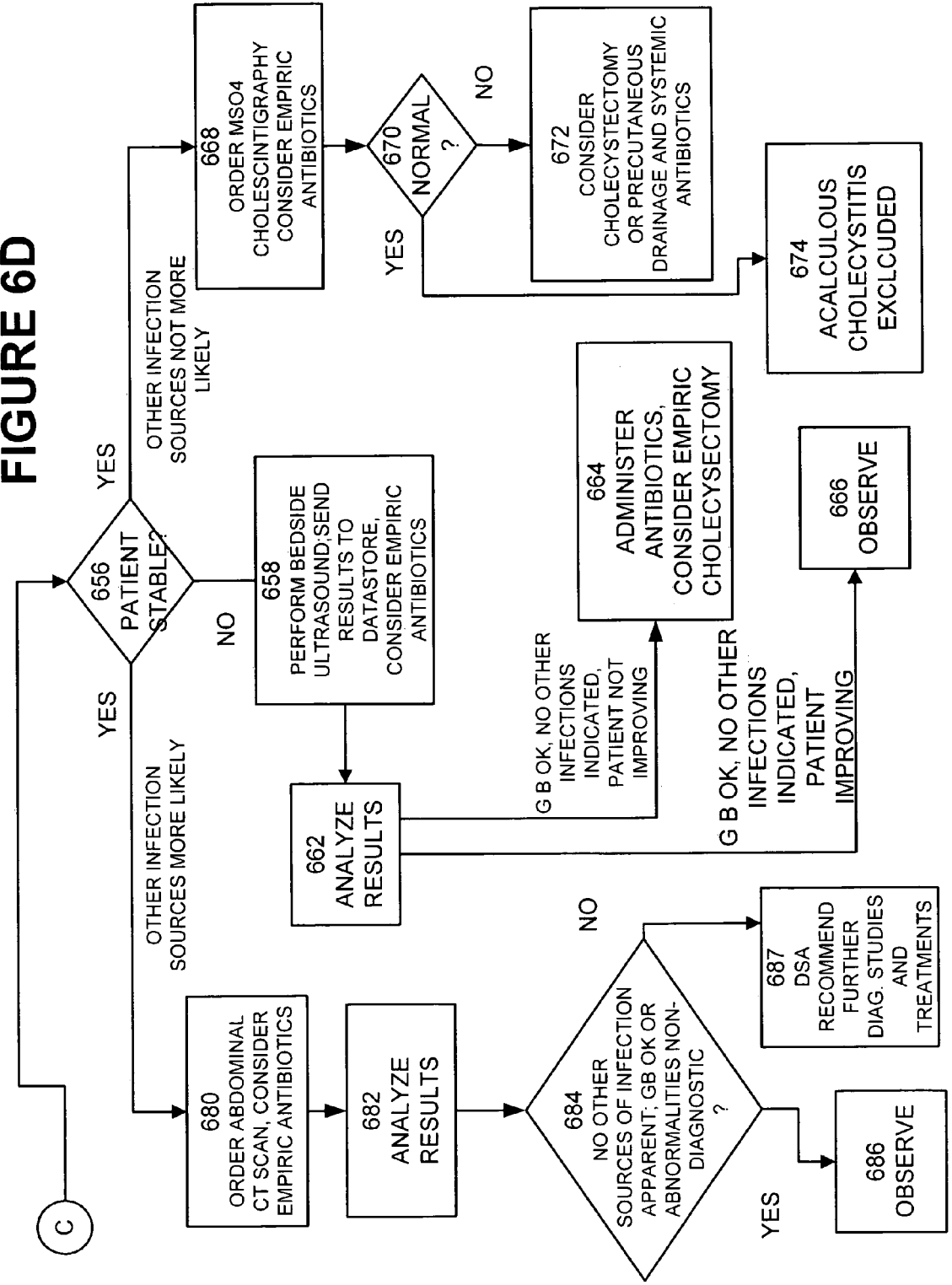

SYSTEM FOR PROVIDING EXPERT CARE TO A BASIC CARE MEDICAL FACILITY FROM A REMOTE LOCATION

RELATIONSHIP TO OTHER APPLICATIONS

This application is a continuation in part of application Ser. No. 10/654,668 filed Sep. 4, 2003 now U.S. Pat. No. 7,475,019 and a continuation in part of application Ser. No. 10/946,548 filed Sep. 21, 2004, now U.S. Pat. No. 7,256,708 both of which are continuations in part of application Ser. No. 09/443,072 filed Nov. 18, 1999, now U.S. Pat. No. 6,804,656 issued Oct. 12, 2004, which claims the benefit of U.S. Provisional Application No. 60/141,520, filed Jun. 23, 1999. The Ser. Nos. 10/654,668, 10/946,548, 09/443,072, and the 60/141,520 applications are hereby incorporated by reference in their entirety for all purposes.

BACKGROUND

Embodiments of the present invention relate generally to a communication system for medical applications and monitoring of equipment used in the care of monitored patients. More particularly, embodiments of the present invention use a telecommunications network to facilitate the transfer of data from patient monitoring equipment into a computer system that evaluates the monitored data for medical assessment, tracking of progress of treatment, and other applications for patients treated in basic care medical facilities in geographically dispersed locations. As will be described in detail below, as used herein, a basic care medical facility is a medical facility, whether temporary or permanent, that is not generally equipped to provide expert medical care on a twenty-four hour basis. By way of illustration and not as a limitation, a basic care medical facility (BCMF) may be a remote clinic, a doctor's office, a field hospital, a disaster aid station, a medical transit vehicle, and similar care facilities.

Advances in communications, video displays, monitoring devices and computers have made it possible to remotely monitor hundreds of monitored patients from a central command center. Monitoring of patients in a hospitalized environment has become a reality. U.S. Pat. No. 6,804,656, which is incorporated by reference, describes systems and methods for providing continuous, expert network critical care services from a remote location(s). Other systems and methods of remote patient care are described in the prior art monitored patient monitored patient. For example, U.S. Pat. No. 5,868,669 to Iliff was issued for "Computerized Medical Diagnostic and Treatment Advice System." The disclosed invention is for a system and method for providing computerized knowledge based medical diagnostic and treatment advice to the general public over a telephone network.

U.S. Pat. No. 5,823,948 to Ross, Jr. et al was issued for "Medical Records Documentation, Tracking and Order Entry System". The disclosed invention is for a system and method that computerizes medical records, documentation, tracking and order entries. A teleconferencing system is employed to allow patient and medical personnel to communicate with each other. A video system can be employed to videotape a patient's consent.

U.S. Pat. No. 4,878,175 to Norden-Paul et al. was issued for A Method for Generating Patient-Specific Flowsheets By Adding/Deleting Parameters." The disclosed invention is for an automated clinical records system for automated entry of bedside equipment results, such as an EKG monitor, respirator, etc. The system allows for information to be entered at the bedside using a terminal having input means and a video display.

U.S. Pat. No. 5,544,649 to David et al. was issued for Ambulatory Patient Health Monitoring Techniques Utilizing Interactive Visual Communications." The disclosed invention is for an interactive visual system, which allows monitoring of patients at remote sites, such as the patient's home. Electronic equipment and sensors are used at the remote site to obtain data from the patient, which is sent to the monitoring site. The monitoring site can display and save the video, audio and patients data.

U.S. Pat. No. 5,867,821 to Ballantyne et al. was issued for "Method and Apparatus for Electronically Accessing and Distributing Personal Health Care Information and Services in Hospitals and Homes." The disclosed invention is for an automated system and method for distribution and administration of medical services, entertainment services, and electronic health records for health care facilities.

U.S. Pat. No. 5,832,450 to Myers et al. issued for "Electronic Medical Record Using Text Database." The disclosed invention is for an electronic medical record system, which stores data about patient encounters arising from a content generator in freeform text.

U.S. Pat. No. 5,812,983 to Kumagai was issued for "Computer Medical File and Chart System." The disclosed invention is for a system and method which integrates and displays medical data in which a computer program links a flow sheet of a medical record to medical charts.

U.S. Pat. No. 4,489,387 to Lamb et al. was issued for "Method and Apparatus for Coordinating Medical Procedures." The disclosed invention is for a method and apparatus that coordinates two or more medical teams to evaluate and treat a patient at the same time without repeating the same steps.

U.S. Pat. No. 4,731,725 to Suto et al. issued for "Data Processing System which Suggests a Pattern of Medical Tests to Reduce the Number of Tests Necessary to Confirm or Deny a Diagnosis." The disclosed invention is for a data processing system that uses decision trees for diagnosing a patient's symptoms to confirm or deny the patient's ailment.

U.S. Pat. No. 5,255,187 to Sorensen issued for "Computer Aided Medical Diagnostic Method and Apparatus." The disclosed invention is for an interactive computerized diagnostic system which relies on color codes which signify the presence or absence of the possibility of a disease based on the symptoms a physician provides the system.

U.S. Pat. No. 5,839,438 to Chen et al. issued for "Intelligent Remote Visual Monitoring System for Home Health Care Service." The disclosed invention is for a computer-based remote visual monitoring system, which provides in-home patient health care from a remote location via ordinary telephone lines.

U.S. Pat. No. 5,842,978 to Levy was issued for "Supplemental Audio Visual Emergency Reviewing Apparatus and Method." The disclosed invention is for a system which videotapes a patient and superimposes the patient's vital statistics onto the videotape.

U.S. Pat. No. 6,364,834 issued to Reuss, et al. was issued for a "Method and System for Remotely Monitoring Multiple Medical Parameters in an Integrated Medical Monitoring System." The disclosed invention is for an integrated medical monitoring system having a patient monitor, a central monitor, and a remote access device. Each of these devices is tied together through an integrated communications link. The communications between various components of the system are bi-directional, an attribute described as affording the opportunity to change data sampling rates and select which parameters to monitor from the remote location. The thrust of the Reuss Patent is the collection of data from monitors so that the data are available to a caregiver. The caregiver may view the data on a display or request the data for viewing.

U.S. Pat. No. 4,838,275 issued to Lee for a "Home Medical Surveillance System," describes an apparatus for use in a patient's home that includes special furniture on which the patient lies and sits. Embedded in this special furniture are devices that automatically sense multiple parameters related to the patient's health. The disclosed invention is directed to monitoring individual ambulatory patients in a home environment. However, this monitoring is not stated to be continuous.

U.S. Pat. No. 3,646,606 issued to Buxton et al. for a "Physiological Monitoring System," describes an apparatus for measuring physiological parameters indicative of the condition of a patient and sending those parameters to a central monitoring station. The central monitoring station would display the parameters in analog and digital form issue an alert signal in the event certain parameter values are detected. Viewing patient data is accomplished by selecting a patient using a switch (FIG. 3, callout 122). Thus, not all patients are monitored at all times. The described invention is directed to a data gathering system combined with a single event driven process to manage "emergencies." Data is presented to a single operator and, except for certain alert conditions, the evaluation of that data is charged to the single operator.

U.S. Pat. No. 6,322,502 issued to Schoenberg for a "Medical Information System," describes a medical information system that receives patient data and information from various sources and allows that information to be accessed and displayed by members of a medical team. At its core, it is a distributed display system.

U.S. Pat. No. 5,942,986 issued to Shabot, et. al for a "System And Method For Automatic Critical Event Notification," describes a critical event notification system that permits review of a patient's diagnostic information, lab results, chart, or other data, automatically, by computer or similar equipment, and it provides for automatic paging of a responsible physician or physicians should a "critical event" be detected. The decision to page an individual is made automatically by the system, and does not require a direct human decision.

While these inventions provide useful records management and diagnostic tools, none of them provides a comprehensive communications system that incorporates monitoring and real time continuous assessment and intervention of patients treated at basic care medical facilities.

What would be useful would be a communication network for automated monitoring of multiple monitored patients in transit and patients treated in basic care medical facilities, capable of using diverse data sources to provide a continuous assessment of a patient's condition. Such a network would support computerized diagnostic tools to aid caregivers in treating such patients remotely. Such a network would further comprise the ability to flexibly and individually establish and/or revise alerts for patients from a central location based on individualized patient parameters and to utilize computer based algorithms to a communications network optimized for intervening appropriately.

SUMMARY

An embodiment of the present invention uses a telecommunications network to facilitate real-time, continuous assessment of patients receiving care in a basic care medical facility (BCMF). As used herein, a basic care medical facility is a medical facility, whether temporary or permanent, that is not generally equipped to provide expert medical care on a twenty-four basis. By way of illustration and not as a limitation, a basic care medical facility (BCMF) may be a remote clinic, a doctor's office, a field hospital, a disaster aid station, a patient transport vehicle and similar care facilities. A patient may be selected for monitoring based on criteria established by the treatment facility. By way of illustration and not as a limitation, a "BCMF monitored patient" comprises a critically ill patient, an acutely ill patient, a patient with a specific illness, a patient with serious injuries, and a patient with an uncertain diagnosis.

Patient monitoring equipment acquires monitored data elements from a patient monitoring station and transmits the monitored data (sometimes also referred to herein as, "monitoring data") over a network to a remote command center. Monitored data comprises physiological data elements, video data elements, and audio data elements. The remote command center receives the monitored data from all patient monitoring stations. The remote command center also accesses other data relating to the condition of a patient. By way of illustration and not as limitation, the remote command center has access to data relating to personal information about the patient (name, address, marital status, age, gender, ethnicity, next of kin), medical history (illnesses, injuries, surgeries, allergies, medications), admissions information (symptoms, physiological data, time of admission, observations of admitting caregiver), treatment, lab data, test reports (radiology reports and microbiology reports for example), physician's notes, a patient's diagnosis, prescriptions, history, condition, laboratory results and other health-relevant data (collectively "patient data") to the extent available from the BCMF. The data available to the remote command center over the network, that is, the monitored data and the patient data, is collectively referred to as "assessment data."

A rules engine continuously applies a patient-specific rule or rule set to the data elements selected from the assessment data from each BCMF monitored patient to determine whether the patient-specific rule for that site has been contravened. In the event the patient-specific rule has been contravened, an alert at the remote command center is triggered. Patient-specific rules for each BCMF monitored patient may be established and changed at the remote command center for each as the patients' conditions warrant. In one embodiment of the present invention, a patient-specific rule is established to determine whether a patient's condition is deteriorating. In another embodiment, a patient specific rule is established to determine whether a patient's condition is improving. In yet another embodiment of the present invention, an alert that a patient-specific rule has been contravened comprises advice on treatment of the patient.

Another embodiment of the present invention provides continued care software that uses elements of the assessment data to provide decision support and that prompts a user for input to provide decision support to caregivers. A decision support algorithm responds to elements of assessment data to produce textural material describing a medical condition, scientific treatments and possible complications. This information is available in real time to assist in all types of clinical decisions from diagnosis to treatment to triage.

In still another embodiment of the present invention, order writing software facilitates the ordering of procedures and medications using patient-specific data. The order writing software and the continued care software are interactive allowing a caregiver to access features of both applications simultaneously, so that patient orders are given that are consistent and not conflicting with a patient's status and condition (i.e., allergies to medications or medications that may conflict with the order in question).

In an embodiment of the present invention, a BCMF patient care system provides care to BCMF patients based on the capabilities of the BCMF. In this embodiment, the rules engine, the decision support algorithms, the order writing software facilities, and the continued care software are adapted to the capabilities of the BCMF based on the application of site assessment rules to the BCMF. In another embodiment of the present invention, components of a BCMF patient care system may be supplied to the BCMF to improve the level of its treatment capabilities. In still another embodiment of the present invention, components of the BCMF are packaged and assigned a site assessment code. The code is used by the remote command center to predetermine elements of the site assessment process thereby simplifying that process.

In another embodiment of the present invention, patient monitoring equipment acquires monitored data elements from a patient monitoring station and stores monitoring data locally. The stored monitoring data is sent to a remote command center along with patient data at a pre-established time or when requested by remote command center. The remote command center evaluates the "delayed" monitored data and assessment data in the same manner as if these data were received in real time. By way of illustration, the remote command center will apply the rules engine and the decision support algorithms to the delayed monitored data and patient data and provide guidance to the BCMF. This embodiment of the present invention thus provides high quality care in environments where continuous high bandwidth communications are not available or economically infeasible.

In still another embodiment of the present invention, the delivery of stored monitoring data and patient data is expedited by an urgent consultation warning system (herein, the UCWS). The UCWS constantly evaluates the monitoring data and patient data before those data are stored to determine if an urgent consultation is warranted. By way of illustration and not as a limitation, changes in hemodynamic and respiratory measures over time indicative of a degrading condition of a patient would trigger an immediate reporting of all stored monitored and patient data to the remote command center for evaluation.

It is therefore an aspect of the present invention to receive at a remote command center monitoring data from a BCMF monitored patient over a communications network.

It is another aspect of the present invention to make available other data relating to the condition of a patient to the remote command center.

It is yet another aspect of the present invention to establish and/or revise patient specific rules at the remote command center and to apply a rules engine to "assessment data" to determine whether a patient-specific rule is contravened.

It is another aspect of the present invention to determine based on assessment data whether the condition of a BCMF monitored patient warrants revising a patient-specific rule at the remote command center.

It is still another aspect of the present invention to issue an alert from the remote command center in the event a patient-specific rule is contravened.

It is an aspect of the present invention to provide treatment information in an order for an intervention issued by the remote command center to a treatment facility where a BCMF monitored patient is receiving care.

It is a further aspect of the present invention to apply decision support algorithms to data relating to the condition of a patient to provide decision support to caregivers.

It is another aspect of the present invention to provide a video visitation system that allows a remote visitation participant to participate in a video/audio conferencing session with a patient and/or a local visitation participant.

The remote command center receives the monitored data elements from the BCMF monitored patients, accesses patient data elements indicative of a medical condition associated with each of the BCMF monitored patients, establishes patient-specific rules associated with each of the BCMF monitored patients, and applies the patient-specific rules continuously and simultaneously using a rules engine. In an embodiment of the present invention, a patient specific rule comprises an algorithm.

The rules engine selects data elements from the monitored data elements and the patient data elements associated with a BCMF monitored patient, applies a patient-specific rule associated with the BCMF monitored patient to the selected data elements, determines whether the patient-specific rule for the BCMF monitored patient has been contravened; and in the event the patient-specific rule for the BCMF monitored patient has been contravened, issues an alert from the remote command center. By way of illustration and not as a limitation, the alert comprises a patient intervention protocol and order.

In an embodiment of the present invention, the selected data elements comprise a physiological data element of the BCMF monitored patient and a clinical data element of the BCMF monitored patient. In an alternate embodiment of the present invention, the selected data elements comprise a physiological data element of the BCMF monitored patient and a medication data element of the BCMF monitored patient. In yet another embodiment of the present invention, the selected data elements comprise a physiological data element of the BCMF monitored patient and a laboratory data element of the BCMF monitored patient. In still another embodiment of the present invention, the selected data elements comprise a clinical data element of the BCMF monitored patient and a laboratory data element of the BCMF monitored patient. In another embodiment of the present invention, the selected data elements comprise a physiological data element of the BCMF monitored patient and another physiological data element of the BCMF monitored patient. In yet another embodiment of the present invention, the selected data elements comprise at least two data elements of the BCMF monitored patient selected from the group consisting of a physiological data element, a clinical data element of the BCMF monitored patient, a medication data element of the BCMF monitored patient, and a laboratory data element of the BCMF monitored patient.

Additionally, the rules engine determines whether the BCMF monitored patient requires monitoring by the monitoring station. In the event the BCMF monitored patient does not require monitoring by the monitoring station, the rules engine issues a release protocol and order.

In another embodiment of the present invention, the BCMF monitored patient care system further comprises an audio/video teleconferencing server. The audio/video teleconferencing server bridges a local visitation terminal and a remote visitation terminal, sends audio and video signals generated by the local visitation terminal to the remote visitation terminal, sends audio and video signals generated by the remote visitation terminal to the local visitation terminal, and provides the audio data elements and video image data elements to both the remote visitation terminal and the local visitation terminal.

Additionally, the BCMF monitored patient care system accesses a decision support algorithm and applies the decision support algorithm to selected data elements of a BCMF monitored patient and user input to provide patient care advice to the user. Patient care advice may be a diagnosis, a method of treatment, and a laboratory procedure. As will be appreciated by those skilled the art, patient care advice may take other forms without departing from the scope of the present invention.

The decision support system may also access an order writing module that issues orders. By way of illustration and not as a limitation, the order writing module may authorize administering medication to a BCMF monitored patient, authorize subjecting the BCMF monitored patient to a laboratory protocol, and subjecting the BCMF monitored patient to a surgical procedure.

An embodiment of the present invention provides a method for continuous assessment of BCMF monitored patients. Monitored data elements from BCMF monitored patients are received at a remote command center. By way of illustration and not as a limitation, monitored data elements comprise physiological data elements, video image data elements and audio data elements.

In an embodiment of the present invention, patient data elements indicative of a medical condition associated with each of the BCMF monitored patients are accessed. Patient-specific rules associated with each of the BCMF monitored patients are established. Data elements from the monitored data elements associated with the BCMF monitored patient and the patient data elements associated with a BCMF monitored patient are selected and a patient-specific rule associated with the BCMF monitored patient is applied to the selected data elements.

A determination is made whether the patient-specific rule for the BCMF monitored patient has been contravened. In the event the patient-specific rule for the BCMF monitored patient has been contravened, an alert is issued from the remote command center. By way of illustration and not as a limitation, an alert comprises a patient intervention protocol and order. Additionally, a determination is made whether the BCMF monitored patient requires monitoring by the monitoring station. In the event the BCMF monitored patient does not require monitoring by the monitoring station, the rules engine issues a release protocol and order.

In an embodiment of the present invention, the selected data elements comprise a physiological data element of the BCMF monitored patient and a clinical data element of the BCMF monitored patient. In an alternate embodiment of the present invention, the selected data elements comprise a physiological data element of the BCMF monitored patient and a medication data element of the BCMF monitored patient. In yet another embodiment of the present invention, the selected data elements comprise a physiological data element of the BCMF monitored patient and a laboratory data element of the BCMF monitored patient. In still another embodiment of the present invention, the selected data elements comprise a clinical data element of the BCMF monitored patient and a laboratory data element of the BCMF monitored patient. In another embodiment of the present invention, the selected data elements comprise a physiological data element of the BCMF monitored patient and another physiological data element of the BCMF monitored patient. In yet another embodiment of the present invention, the selected data elements comprise at least two data elements of the BCMF monitored patient selected from the group consisting of a physiological data element, a clinical data element of the BCMF monitored patient, a medication data element of the BCMF monitored patient, and a laboratory data element of the BCMF monitored patient.

In an embodiment of the present invention, a local visitation terminal and a remote visitation terminal are bridged. Audio and video signals generated by the local visitation terminal are sent to the remote visitation terminal and audio and video signals generated by the remote visitation terminal are sent to the local visitation terminal. The audio data elements and video image data elements are provided to both the remote visitation terminal and the local visitation terminal.

Another embodiment of the present invention provides a method wherein a decision support algorithm is accessed. The decision support algorithm is applied to selected data elements of a BCMF monitored patient and to user input to provide patient care advice to the user. Patient care advice may be in the form of a diagnosis, a method of treatment, and a laboratory procedure. As will be appreciated by those skilled the art, patient care advice may take other forms without departing from the scope of the present invention.

The decision support system may also access an order writing module that issues orders. By way of illustration and not as a limitation, the order writing module may authorize administering medication to a BCMF monitored patient, authorize subjecting the BCMF monitored patient to a laboratory protocol, and subjecting the BCMF monitored patient to a surgical procedure.

DESCRIPTION OF THE FIGURES

FIG. 5 illustrates an order writing data flow according to an embodiment of the present invention.

DETAILED DESCRIPTION

Figure 1:
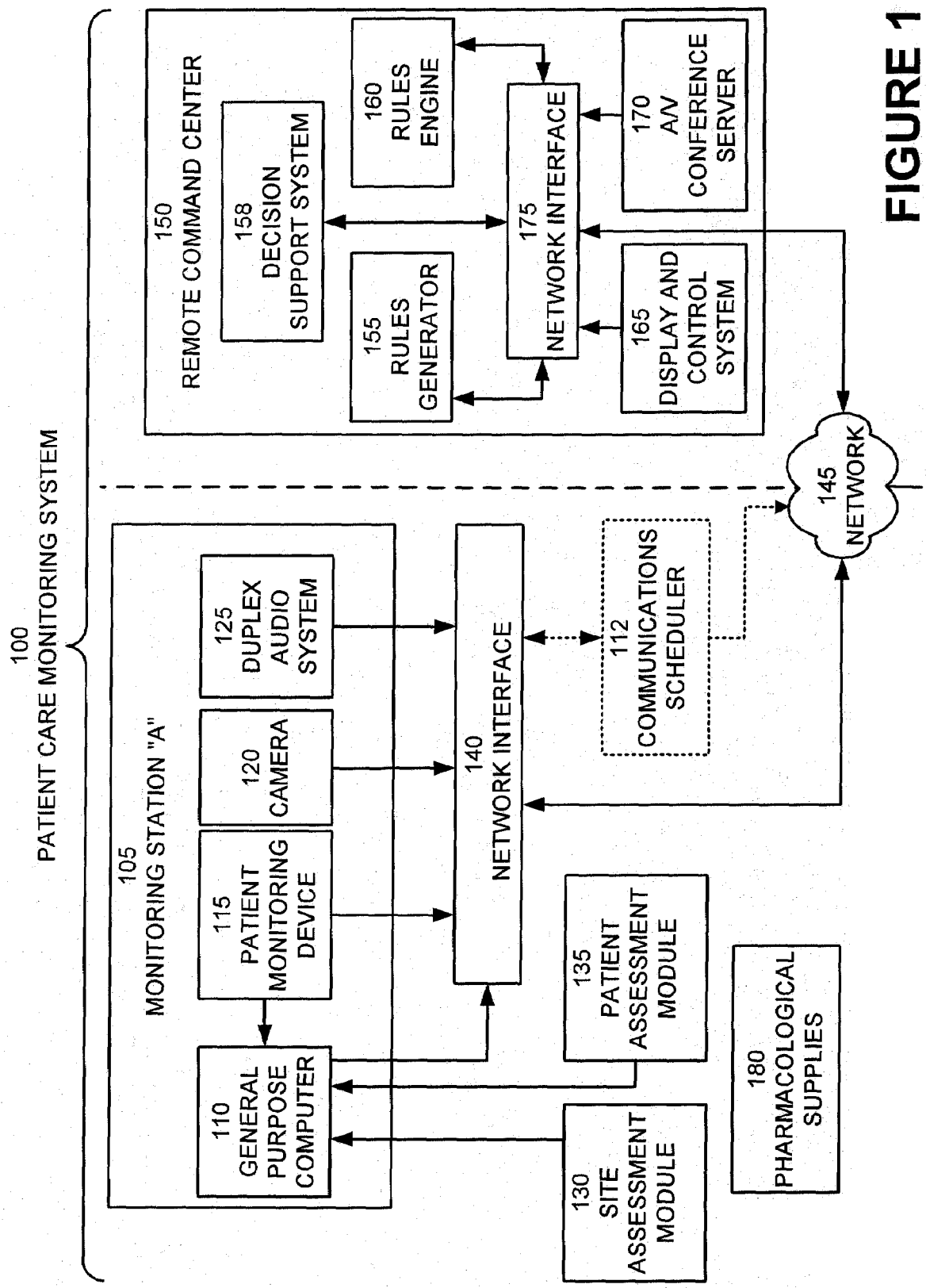
FIG. 1 illustrates a block diagram of the components of a BCMF monitored patient care system according to embodiments of the present invention.

The following terms used in the description that follows. The definitions are provided for clarity of understanding:

| | |
|---|---|
| assessment data - | assessment data is all data relevant to the health of a patient. |
| BCMF - | A "basic care medical facility;"a facility, whether temporary or permanent, that is not generally equipped to provide expert medical care on a twenty-four basis. By way of illustration and not as a limitation, a BCMF may be a remote clinic, a doctor's office, a field hospital, a disaster aid station, a patient transport vehicle and similar care facilities |
| caregiver - | an individual providing care to a patient. Examples include a nurse, a doctor, medical specialist (for example and without limitation an intensivist, cardiologist or other similar medical specialist). |
| clinical data - | data relating to the observed symptoms of a medical condition. |
| BCMF monitored patient - | a person admitted to a BCMF. |
| monitored data - | data received from monitoring devices connected to a BCMF monitored patient. |

| | |
|---|---|
| BCMF monitored patient - | a BCMF monitored patient from whom monitored data is collected and whose condition is subject to continuous real-time assessment from a remote command center. |
| patient data - | data relating to a patient's diagnosis, prescriptions, history, condition, laboratory results and other health-relevant data. |
| physiological data - | any data relating to the functions of the human body and its processes. |
| symptom - | any sign or indication of a health condition that can be identified from patient reports and/or assessment data. |

An embodiment of the present invention uses a telecommunications network to facilitate real-time, continuous assessment of patients receiving care in a basic care medical facility (BCMF). As used herein, a basic care medical facility is a medical facility, whether temporary or permanent, that is not generally equipped to provide expert medical care on a twenty-four basis. By way of illustration and not as a limitation, a basic care medical facility (BCMF) may be a remote clinic, a doctor's office, a field hospital, a disaster aid station, a patient transport vehicle and similar care facilities.

Patient monitoring equipment acquires monitoring data from a BCMF monitored patient associated with a patient monitoring station and transmits the monitoring data over a network to a remote command center. The remote command center receives the monitoring data from all of the patient monitoring stations. The remote command center also accesses other data relating to the condition of a patient such as the "patient data" as defined above. The data available to the remote command center over the network, that is, the monitoring data and the patient data, is collectively referred to as "assessment data."

In an embodiment of the present invention, a BCMF patient care system provides care to BCMF patients based on the capabilities of the BCMF. In this embodiment, the rules engine, the decision support algorithms, the order writing software facilities, and the continued care software are adapted to the capabilities of the BCMF based on the application of site assessment rules to the BCMF. In another embodiment of the present invention, components of a BCMF patient care system may be supplied to the BCMF to improve the level of its treatment capabilities. In still another embodiment of the present invention, components of the BCMF are packaged and assigned a site assessment code. The code is used by the remote command center to predetermine elements of the site assessment process thereby simplifying that process.

FIG. 1 illustrates a block diagram of the components of a BCMF monitored patient care system according to embodiments of the present invention. A BCMF monitored patient care system 100 comprises portable patient monitoring station "A" 105. While FIG. 1 illustrates a single portable patient monitoring station, the invention is not so limited. Multiple portable patient monitoring stations may be used without departing from the scope of the present invention. For the sake of clarity, the description that follows will refer to portable patient monitoring station "A" 105. However, the description applies to all portable patient monitoring stations within the BCMF monitored patient care system 100.

Portable patient monitoring station "A" 105 comprises a general purpose computer 110, a patient monitoring device 115, a camera 120, and a duplex audio system 125. While FIG. 1 illustrates a patient monitoring device, the invention is not so limited. Multiple patient monitoring devices may be used without departing from the scope of the present invention. For the sake of clarity, the description that follows will refer to patient monitoring 115.

General purpose computer 110 provides data entry, display and printing capabilities through means known to those skilled in the art.

The components of portable patient monitoring station "A" 105 are connected to network 145 via network interface 140. Network 145 may be a wired network, a wireless network, a satellite network, a public switched telephone network, an IP network, a packet switched network, a cell phone network, a cable network, and a coax network, a hybrid fiber coax network.

Pharmacological supplies 180 comprise an inventory of medicines that is provided to a BCMF depending on circumstances. By way of illustration and not as a limitation, a BCMF monitored patient care system 100 may be dropped shipped to a disaster area where the primary concern is sanitation-based illnesses. In this example, pharmacological supplies 180 would comprise those medications, diagnostic tools, and preventive agents that are useful in countering the expected diseases and not readily available to the BCMF. By contrast, if the disaster area is most likely to experience patients with physical injuries, pharmacological supplies would be weighted to supplies needed to diagnose, treat, and comfort the wounded.

A site assessment module 130 and a patient assessment module 135 connect to network interface 140 via general purpose computer 110.

It is anticipated that BCMF monitored patient care system 100 will be used in BCMFs that have limited resources. Site assessment module 130 provides information indicative of the ability of a BCMF to provide diagnostic, laboratory, surgical, and pharmacological services. In an embodiment of the present invention, site assessment module acquires site assessment data from the BCMF and produces service level measures comprising an inventory of available monitoring data elements, an inventory of available diagnostic services, an inventory of available surgical treatment services, and an inventory of available laboratory services. These data may be acquired via a survey or by reference to a database in which the survey data of the BCMF are stored.

In another embodiment of the present invention, a BCMF monitored patient care system 100 is provided to a BCMF. The BCMF monitored patient care system 100 comprises an assessment code that details the capability of the BCMF monitored patient care system 100. By way of illustration and not as a limitation, the assessment code may indicate the number of monitoring devices incorporated into the BCMF monitored patient care system 100, the patient parameters that can be acquired using the monitoring devices, and the pharmacological supplies 180 provided with the BCMF monitored patient care system 100.

Patient assessment module 135 provides patient condition data indicative of a BCMF monitored patient to remote command center 150. In an embodiment of the present invention, patient assessment module 135 acquires data relating to a patient's diagnosis, prescriptions, history, condition, laboratory results and other health-relevant data. These data may be acquired via a survey or by reference to a database in which the patient condition data are stored.

As will appreciated by those skilled in the art, site assessment module 130 and a patient assessment module 135 may be standalone components or may be software applications operating on general purpose computer 110.

Also connected to network 145 is remote command center 150. Remote command center 150 comprises a patient rules generator 155, a rules engine 160, decision support system 158, display and control system 165, and audio/video (A/V) conferencing server 170. Decision support system 158 issues instructions to the rules generator 155 when rules required for a patient. Once the rules are generated by rules generator 155, the decision support system 158 causes the rule to be referred to the rules engine 160 for subsequent application to the specific patient for whom the rule was originally generated. A network interface 175 provides connectivity between network 145 and the other elements of the remote command center. Network 145 is configured to permit access to external networks (not illustrated), such as the Internet.

Video camera 120 is movable both horizontally and vertically and zoomable through remote commands from the display and control system 165 of remote command center 150 so that specific views of the patient may be obtained both up close and generally. Duplex audio system 125 comprises a speaker and microphone (not illustrated) to permit both one-way audio monitoring of the patient and two-way communication with the patient or others in proximity to portable patient monitoring station "A" 105.

Patient monitoring device 115 acquires physiological data from a patient in real-time. In an embodiment of the present invention, general purpose computer 110 comprises a printer that receives and prints orders and instructions from an authorized remote caregiver. By way of illustration and not as a limitation, an order comprises a lab order, a medication, and a procedure. Orders are tailored to the capabilities of the BCMF patient care system 100.

A network interface 140 provides access to network 145 for transmission of the monitored data, video signal, and audio signals to the remote command center 125 and the receipt of the audio signals and, optionally, printer signals at the monitoring station.

Figure 2:
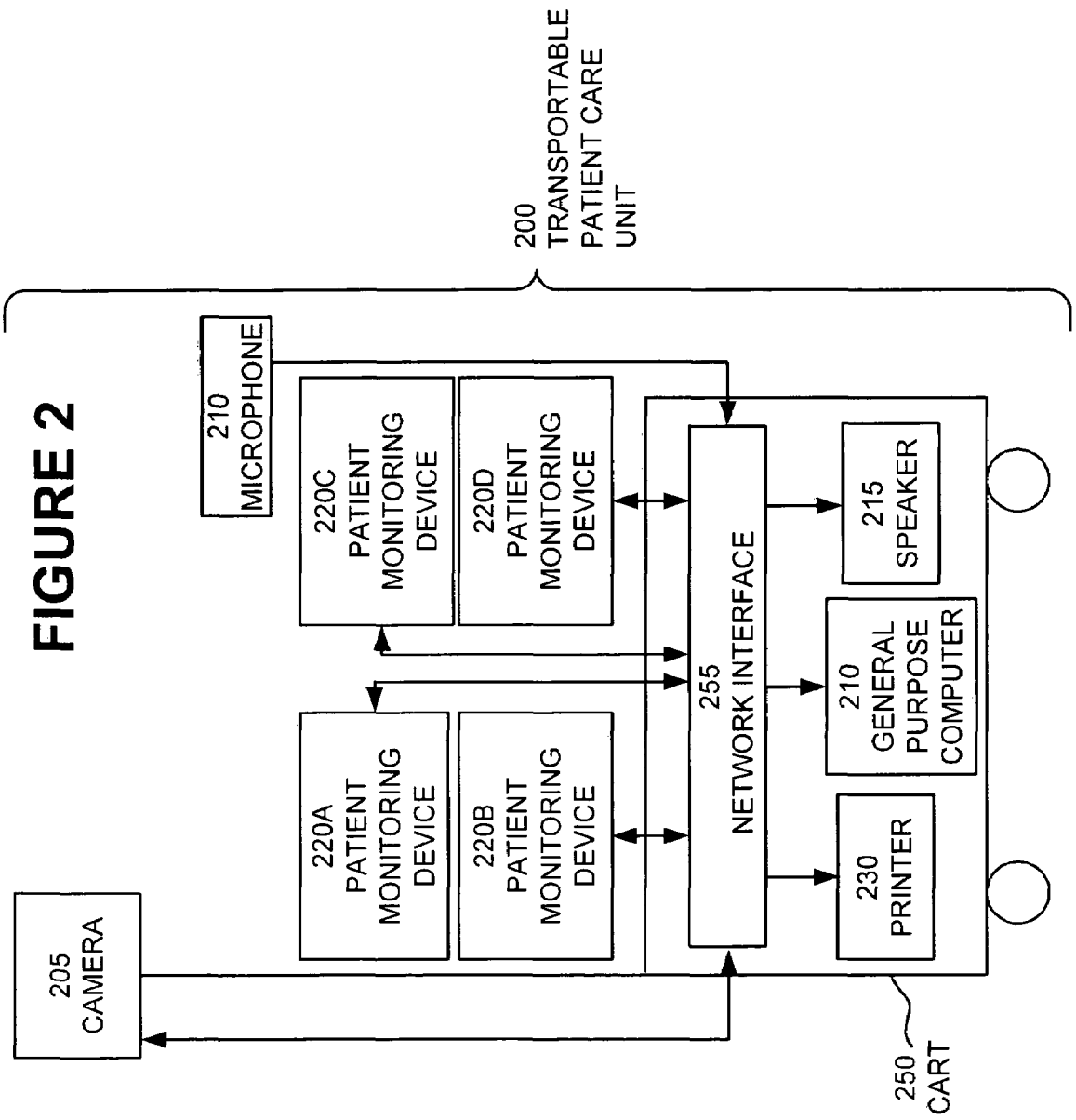
FIG. 2 illustrates the components of a transportable patient care unit according to embodiments of the present invention.

FIG. 2 illustrates the components of a transportable patient care unit according to embodiments of the present invention. A transportable patient care unit 200 comprises the components illustrated in FIG. 1 mounted on a cart 250. Video camera 205 is movable both horizontally and vertically and zoomable through remote commands from the display and control system 165 of remote command center 150 (see, FIG. 1) so that specific views of the patient may be obtained both up close and generally. A microphone 210 and a speaker 215 permit both one-way audio monitoring of the patient and two-way communication with the patient or others located in proximity to transportable patient care unit 200. Patient monitoring devices 220A-220D acquire physiological data from a patient in real-time. A printer 230 receives and print orders from an authorized caregiver. By way of illustration and not as a limitation, an order comprises a lab order, a medication, and a procedure. A network interface 255 provides access to a network (see FIG. 1, 150) for transmission of the monitored data, video signal, and audio signals to a remote command center and the receipt of the audio signals and printer signals at the monitoring station. A general purpose computer 210 allows on site care givers to provide additional data that may be germane to the care of the patient.

Referring again to FIG. 1, the remote command center 125 receives monitored data from portable patient monitoring station "A" 105 and patient condition data from patient assessment module 135 via network 145 through network interface 175. Monitored data comprises real-time data received from monitoring equipment at portable patient monitoring station "A" 105 that is configured to receive physiological data BCMF monitored patient and associated with patient monitoring station "A" 105.

The rules generator 155 and the rules engine 160 facilitate detection of impending problems and automate problem detection thereby allowing for intervention before a patient condition reaches a crisis state. Rules engine generator 155 establishes one or more rules for the BCMF monitored patient associated with patient monitoring station "A" 105. In an embodiment of the present invention, rules generator 155 generates a patient specific rule that is consistent with the patient assessment data and with the service level measures established by the site assessment module 130. The rules engine 160 continuously applies a patient-specific rule to selected data elements of patient assessment data (assessment data is all data relevant to the health of a patient) to determine whether the patient-specific rule for a BCMF monitored patient has been contravened. In the event the patient-specific rule has been contravened, the remote command center determines whether intervention is warranted. In another embodiment of the present invention, the remote command center also issues an alert.

In one embodiment of the present invention, a patient-specific rule is established to determine whether a patient's condition is deteriorating and an alert comprises an intervention order and protocol. In another embodiment of the present invention, the rules engine is further adapted to determine whether a BCMF monitored patient requires monitoring by a monitoring station. If not, a release protocol and order are issued. In still another embodiment of the present invention, a patient-specific rule dictates threshold limits for changes over time of specific vital sign data. Thresholds that are patient-specific disease-specific are established. The rules engine then evaluates the monitored data for the specific vital sign data to determine if a change threshold has been exceeded.

For example, a patient with coronary artery disease can develop myocardial ischemia with relatively minor increases in heart rate. Heart rate thresholds for patients with active ischemia (e.g. those with unstable angina in a coronary care unit) are set to detect an absolute heart rate of 75 beats per minute. In contrast, patients with a history of coronary artery disease in a surgical ICU have thresholds set to detect either an absolute heart rate of 95 beats per minute or a 20% increase in heart rate over the baseline. For this threshold, current heart rate, calculated each minute based on the median value over the preceding 5 minutes, is compared each minute to the baseline value (the median value over the preceding 4 hours).

In another embodiment of the present invention, a patient-specific rule is based on multiple variables. By way of illustration, a patient-specific rule is contravened if the rules engine determines that monitored data reflects both a simultaneous increase in heart rate of 25% and a decrease in blood pressure of 20%, occurring over a time interval of 2 hours.

For multi-variable patient-specific rules, thresholds rely on known or learned associations between changes in multiple variables, which variables may comprise diverse data types. Thus, a patient-specific rule may associate monitored physiological data with patient clinical data. The association may change depending on the diagnosis of the patient, the medication given the patient, and the results of laboratory data. For example, a patient-specific rule may associate central venous pressure and urine output, because simultaneous decreases in these two variables can indicate that a patient is developing hypovolemia. Another patient-specific rule may cause the rules engine to evaluate laboratory data (e.g. looking for need to exclude active bleeding and possibly to administer blood).

In an embodiment of the present invention, a patient-specific rule established for a BCMF monitored patient and the BCMF monitored patient is associated with a particular portable monitoring station. In this embodiment, if the patient were later associated with a different monitoring station, the remote command center would associate the patient-specific rule with the different monitoring station at the time that the association between the BCMF monitored patient and the different monitoring station is made. In this way, patient specific rules "move" with the patient without manual intervention.

In another embodiment of the present invention, patient monitoring equipment acquires monitored data elements from a patient monitoring station and stores monitoring data in general purpose computer 110. The stored monitoring data is sent from general purpose computer 110 to the remote command center 150 along with patient data under control of an optional communications scheduler 112 at a pre-established time such as hour or when an "event" occurs as noted below, or when requested by remote command center 150. The remote command center 150 evaluates the "delayed" monitored data and assessment data in the same manner as if these data were received in real time. By way of illustration, the remote command center will generate patient specific rules using rules generator 155, apply those rules using rules engine 160 to the delayed monitored data and patient data and provide guidance to the BCMF. The decision support algorithms of decision support system 158 may also be applied to the delayed monitored data and patient data. This embodiment of the present invention thus provides high quality care in environments where continuous high bandwidth communications are not available or economically infeasible.

In still another embodiment of the present invention, the delivery of stored monitoring data and patient data is expedited by an urgent consultation warning system (herein, the UCWS) operated by general purpose computer 110. The UCWS constantly evaluates the monitoring data and patient data before those data are stored to determine if an event has occurred that warrants an urgent consultation. By way of illustration and not as a limitation, changes in hemodynamic and respiratory measures over time indicative of a degrading condition of a patient would trigger an immediate reporting of all stored monitored and patient data to the remote command center 150 for evaluation.

Figure 3:
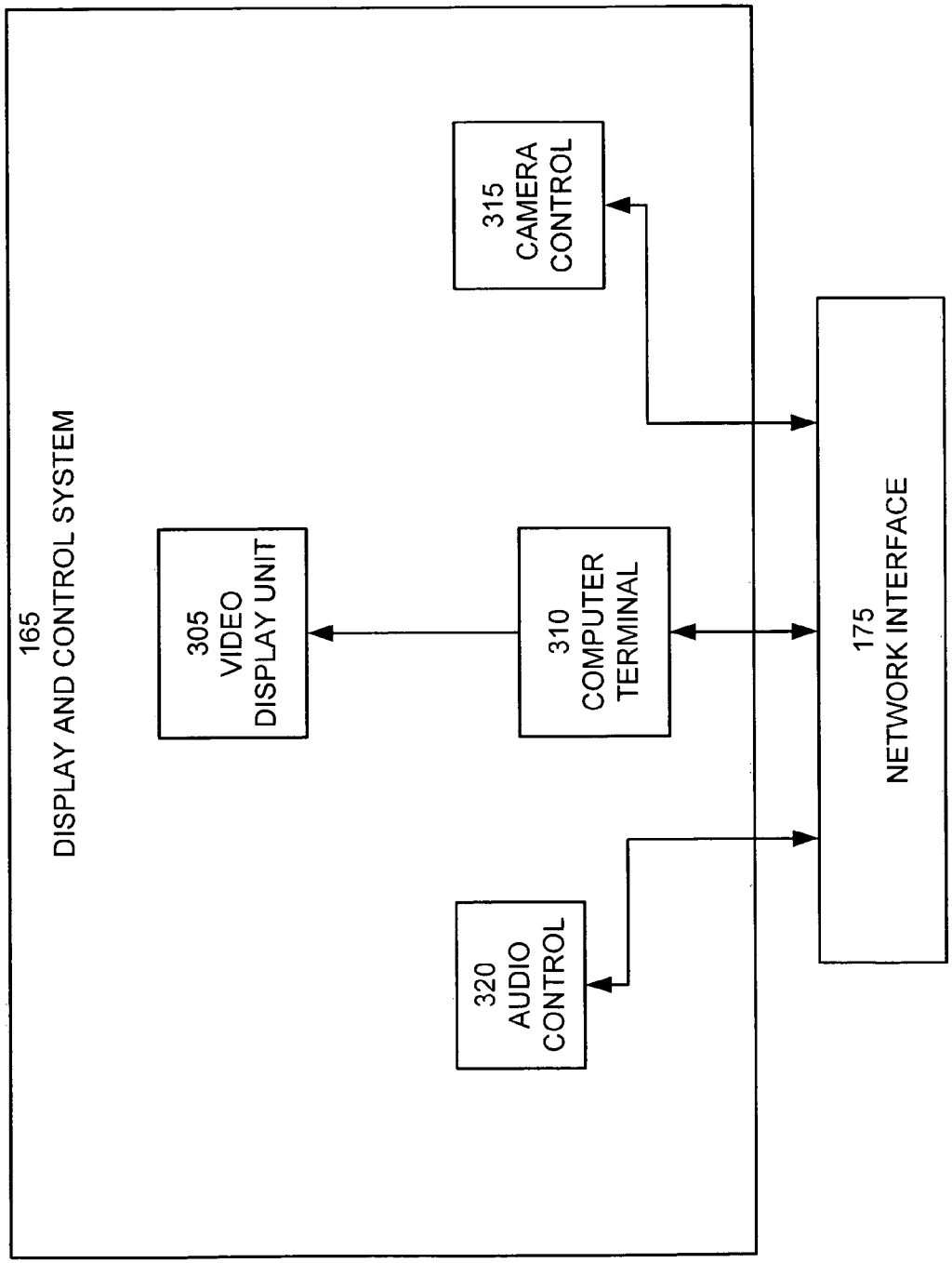
FIG. 3 illustrates a display and control system according to an embodiment of the present invention.

Referring to FIG. 1, the display and control system 165 provides the human interface for the remote command center. FIG. 3 illustrates a display and control system according to an embodiment of the present invention. A display and control system 165 comprises a video display unit 305, a computer terminal 310, a camera control 315, and an audio control 320. The video display unit 305 displays real-time monitoring data and video images from portable patient monitoring station "A" 105. The computer terminal 310 allows selecting the layout and content displayed on the video display unit 305, provides access to the record of the patient associated with portable patient monitoring station "A" 105, and permits entry of data into that record. The camera control 315 permits control from the remote command center 125 of the video camera 120 (see FIG. 1) at the portable patient monitoring station "A" 105. The audio control permits control from the remote command center 150 of a microphone and a speaker within the duplex audio system 125 of portable patient monitoring station "A" 105. Connectivity between the components of the display and control systems 165 and portable patient monitoring station "A" 105 is provided by network interface 175, network 145, and network interface 140.

Figure 4:
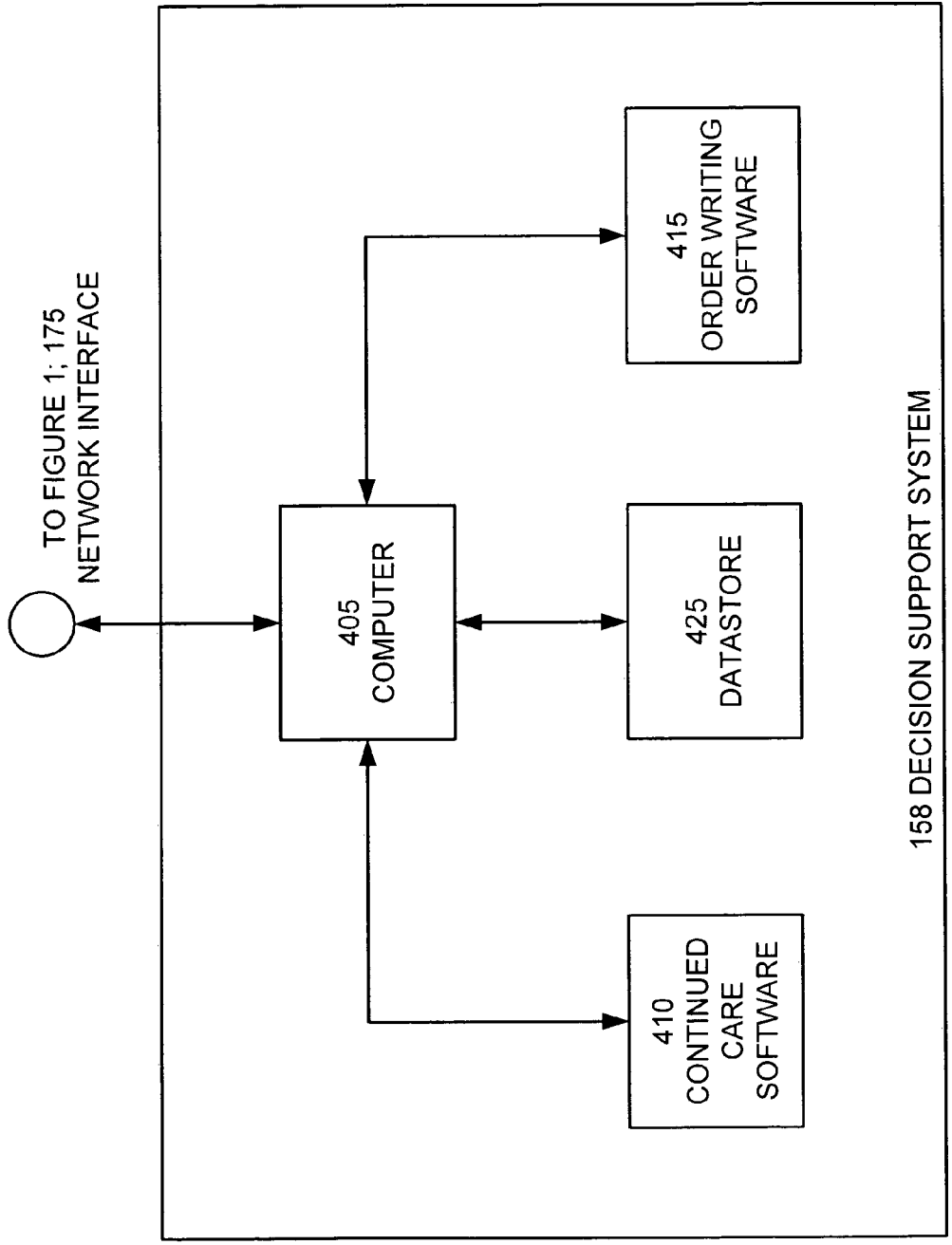
FIG. 4 illustrates a decision support system according to an embodiment of the present invention.

Referring again to FIG. 1, the remote command center 150 comprises decision support system 158. FIG. 4 illustrates a decision support system according to an embodiment of the present invention. Referring to FIG. 4, decision support system 158 is connected to network interface 175 and comprises a computer 405. Computer 405 operates continued care software 420 and order writing software 415. Continued care software 410 and order writing software 415 make calls to datastore 425 to access the assessment data related to a particular BCMF monitored patient associated with portable patient monitoring station "A" 105 (see, FIG. 1).

Continued care software 420 comprises decision support algorithms that operate on elements of assessment data and/or input from a caregiver to facilitate decisions relating to diagnosis, treatment and triage. Continued care software may be applied at the time the patient is admitted and throughout the patient's stay within a treatment facility. Thus, a diagnosis may be made based on the initial data acquired during admission, following the completion of laboratory procedures, or after other pertinent information is acquired. In an embodiment of the present invention, continued care software 420 evaluates selected data elements of assessment data continuously and provides an alert if those data are indicative of a different diagnosis. The alert may take the form of suggested diagnoses that are vetted by a series of questions posed by the continued care software 420 to a caregiver. Based on the responses to the questions, a suggested diagnosis may be eliminated. The alert may also comprise instructions for specific tests to be run on the BCMF monitored patient to help formulate a new diagnosis. Once a diagnosis is confirmed, the continued care software 420 continues to monitor changes in patient data and issues an alert if the current diagnosis should be reevaluated by a caregiver.

Decision support system 158 also issues instructions to the rules generator 155 when rules required for a patient. Once the rules are generated by rules generator 155, the decision support system 158 causes the rule to be referred to the rules engine 160 for subsequent application to the specific patient for whom the rule was originally generated.

In another embodiment of the present invention, patient monitoring equipment acquires monitored data elements from a patient monitoring station and stores monitoring data in general purpose computer 110. The stored monitoring data is sent from general purpose computer 110 to the remote command center 150 along with patient data under control of an optional communications scheduler 112 at a pre-established time such as hour or when an "event" occurs as noted below, or when requested by remote command center 150. The continued care decision support system 158 evaluates selected data elements of the assessment data in the same manner as if these data were received in real time and provides an alert if those data are indicative of a different diagnosis.

In still another embodiment of the present invention, the delivery of stored monitoring data and patient data is expedited by an urgent consultation warning system (herein, the UCWS) operated by general purpose computer 110. The UCWS constantly evaluates the monitoring data and patient data before those data are stored to determine if an event has occurred that warrants an urgent consultation. By way of illustration and not as a limitation, changes in hemodynamic and respiratory measures over time indicative of a degrading condition of a patient would trigger an immediate reporting of all stored monitored and patient data to the decision support system 158 for evaluation.

In still another embodiment of the present invention, continued care software 420 operates on a diagnosis to "triage" a patient. For example and without limitation a caregiver requests an Apache II score based on the diagnosis. Continued care software 420 calls selected data elements from datastore 425 appropriate to the diagnosis. The values of the selected data elements are weighted according to an algorithm and a patient severity score is determined. This patient severity score is used to determine whether the patient is treated in a patient monitoring station. For example, if one embodiment of the present invention, if the severity score is greater than or equal to a particular threshold, the patient is identified as requiring observation via a patient monitoring station. If the severity score is less than that threshold, the patient is triaged to a facility other than a patient monitoring station, thereby assigning patient monitoring stations to patients who are most likely to benefit from monitoring and continued assessment.

In another embodiment of the present invention, computer 405 operates order writing software 415, either independently or in conjunction with the operation of continued care software 420 to order tests to complete the data required for a potential diagnosis.

According to another embodiment of the present invention, the orders issued by order writing software 415 are consistent with the service level measures established by the site assessment module 130.

FIG. 5 illustrates an order writing data flow according to an embodiment of the present invention. Referring to FIG. 5, order entry user interface 500 allows the caregiver to order procedures and medication to assist the patients at a patient monitoring station. For example, the caregiver can order an ECG 504. Thereafter the order is reviewed and a digital signature relating to the caregiver is supplied 506. Once reviewed and signed off, the order is approved 507 and sent to the data output system 510. Thereafter the data output system prints the order to the printer at a patient monitoring station 516. For record keeping purposes the order is exported in the HL7 language to the hospital data system 518. In addition the data output system adds an item to the database that will subsequently cause a caregiver to check the ECG results. This notification to the task list is provided to the database 514. In addition, as part of the database an orders file relating to the specific patient is also kept. The fact that an ECG has been ordered is entered in the orders file for that patient.

In a similar fashion using the order entry user interface 500 the caregiver can order medications 502 for a patient. The medication order then is provided to an order checking system 508. The order checking system retrieves information from the database 514 relating to allergies of the patient and medication list that comprises medications that are already being administered to the patient. This allows for the order checking system to check for drug allergies and drug interactions. Further laboratory data is extracted from the database 514 and the order checking system checks to insure that there will be no adverse impact of the recommended dosage upon the renal function of the patient. Once the order checking system 508 is completed, the order is approved and provided to the order review and signature module 506. In this module the digital signature of a caregiver is affixed to the order electronically and the order is approved 507. Thereafter it is provided to the data output system 510 where again the orders are printed or transmitted via HL7 for the patient monitoring station 516, for the pharmacy 517 and for the treatment facility data system 518. In this case, any medications that are ordered are then provided to the medications list file in the database 514 so that the complete list of all medications that are being administered to the patient is current.

In an embodiment of the present invention, order checking system 508 determines whether the order is consistent with the service level measures established by the site assessment module 130. If the order is not consistent with the service level measures, the order is suppressed and the caregiver is notified that an alternative treatment is required.

As noted, the order writing software 415 may also interact with continued care software 410. Referring again to FIG. 4, a caregiver selects a suggested diagnosis from the continued care software 420 and enters the order writing software 415. As previously described, the orders issued by order writing software 415 are consistent with the service level measures established by the site assessment module 130. The order writing software identifies the appropriate test or tests and issues the actual order or orders for the identified tests. Each order is then sent to the appropriate testing facility. The tests are conducted, and the completion of the order is reported to the data store 425 and the completion information is received by the order writing software 415. Additionally, continued care software 420 acquires the test results from the datastore 425 and updates the list of suggested diagnoses.

Continued care software 420 provides reference material directed to the standardized treatment of the BCMF monitored patient. In order to standardize treatment provided to BCMF monitored patients at the highest possible level, decision support algorithms are used in the present invention. These include textural material describing the topic, scientific treatments and possible complications. This information is available in real time to assist in all types of clinical decisions from diagnosis to treatment to triage.

In an embodiment of the present invention, the decision response algorithms are responsive to the service level measures established by the site assessment module 130. In this embodiment, the algorithms adjust the response to fit the capabilities of the BCMF.

As noted earlier, an aspect of the present invention is to standardize care and treatment across patient monitoring stations. This is effective in the present invention by providing decision support to caregivers as well as information concerning the latest care and practice standards for any given condition. Table 1 below is an exemplary list of a wide variety of conditions within the general categories of cardiovascular, endocrinology, general, gastrointestinal, hematology, infectious diseases, neurology, pharmacology, pulmonary, renal, surgery, toxicology, for which algorithms of care have been developed. As will be appreciated by those skilled in the art, the list in Table 1 is not exhaustive and other decision support algorithms may be developed for other conditions without departing from the scope of the present invention.

TABLE 1

Figure 6A:
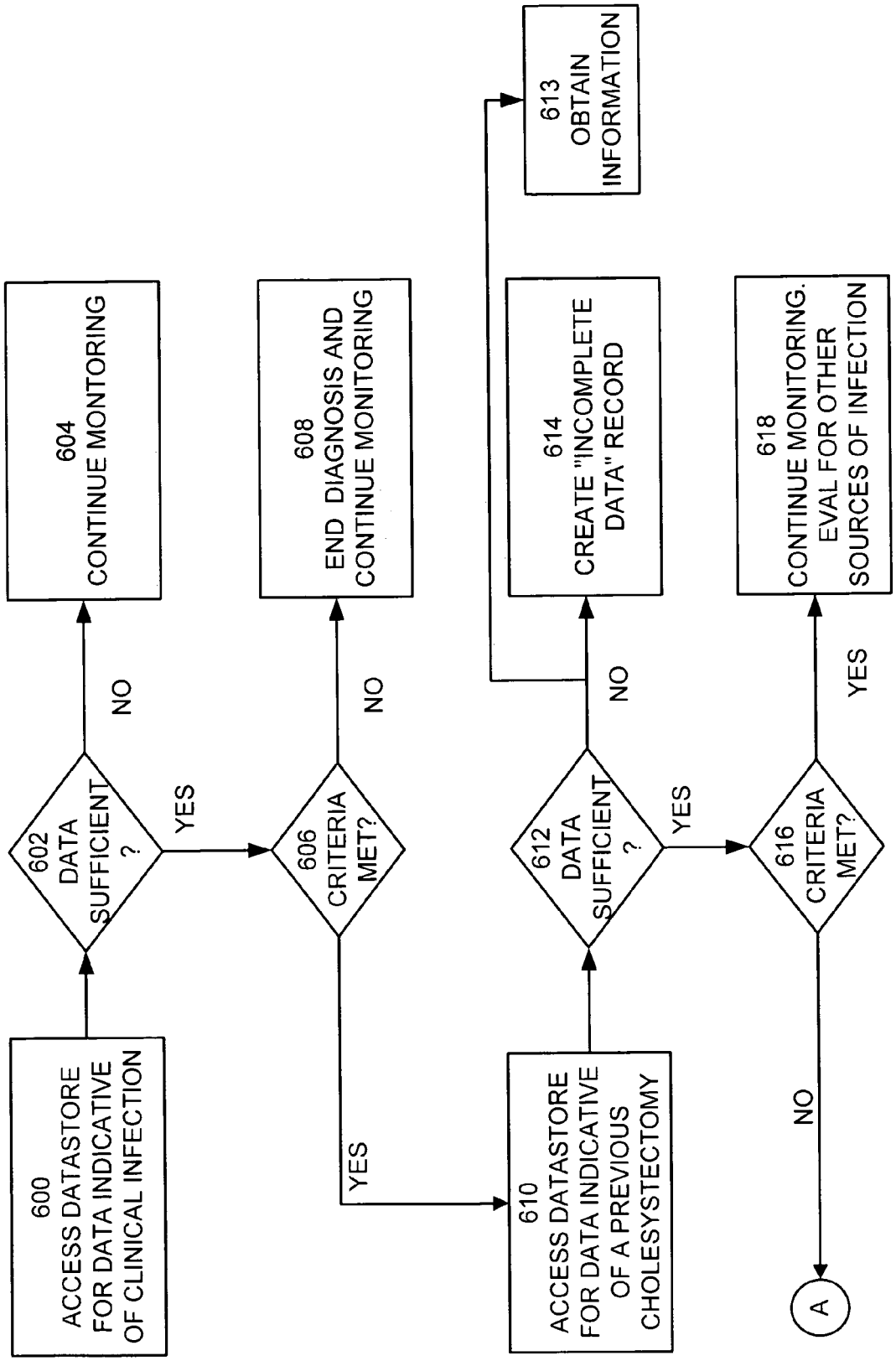
FIGS. 6A, B, C, and 6D illustrate the flow of a decision support algorithm for acalculous cholecsystitis according to an embodiment of the present invention.

Bradyarrhythmias diagnosis & treatment
Cardiogenic shock treatment
Cardio-pulmonary resuscitation treatment
Congestive heart failure diagnosis & treatment
Emergency cardiac pacing indications
Fluid resuscitation indications & treatment
Hypertensive crisis treatment
Implantable cardio-defibrillator indications
Intra-aortic balloon device indications
Magnesium treatment
Treatment of hypotension
Myocardial infarction diagnosis & treatment
MI with left bundle branch block diagnosis
Pulmonary artery catheter indications
Permanent pacemaker indications
Pulmonary embolism diagnosis
Pulmonary embolism treatment
Supra-ventricular tachyarrhythmias diagnosis & treatments
Unstable angina diagnosis & treatment
Venous thromboembolism prophylaxis treatment
Venous thrombosis: diagnosis & treatment
Ventricular arrhythmias diagnosis & treatment
Adrenal insufficiency diagnosis and treatment
Diabetic ketoacidosis diagnosis and treatment
Hypercalcemia: diagnosis & treatment
Hyperglycemia: diagnosis and treatment
Steroid replacement treatment TABLE 1-continued Thyroid disease diagnosis and treatment
End of life treatment decisions
Pressure ulcers treatment
Organ procurement indications and salvage
Antibiotic associated colitis diagnosis and treatment
Hepatic encephalopathy diagnosis and treatment
Hepatic failure diagnosis and treatment
Treatment of patients with ascites
Nutritional management
Acute pancreatitis diagnosis and treatment
Upper gastro-intestinal bleeding: stress prophylaxis treatment
Upper gastro-intestinal bleeding: non-variceal treatment
Upper gastro-intestinal bleeding: variceal treatment
Heparin treatment
Heparin-induced thrombocytopenia diagnosis and treatment
The bleeding patient diagnosis and treatment
Thrombocytopenia diagnosis and treatment
Thrombolytic treatment
Transfusion indications
Hematopoetic growth factor indications
Warfarin treatment
Acalculus cholecystitis diagnosis and treatment
Bloodstream infections diagnosis and treatment
Candiduria diagnosis and treatment
Catheter related septicemia diagnosis and treatment
Catheter replacement strategies
Endocarditis prophylaxis
Endocarditis diagnosis and treatment
Febrile neutropenia diagnosis and treatment
Fever of Unknown Origin diagnosis
HIV+ patient infections diagnosis and treatment
Meningitis diagnosis and treatment
Necrotizing soft tissue infections diagnosis and treatment
Non-infectious causes of fever diagnosis
Ophthalmic infections diagnosis and treatment
Pneumonia, community acquired diagnosis and treatment
Pneumonia, hospital acquired diagnosis and treatment
Septic shock diagnosis and treatment
Sinusitis diagnosis and treatment
Systemic Inflammatory Response Syndrome diagnosis and treatment
Transplant infection prophylaxis
Transplant-related infections diagnosis and treatment
Agitation, anxiety, depression & withdrawal diagnosis and treatment
Brain death diagnosis
Guillain-barre syndrome diagnosis and treatment
Intracerebral hemorrhage diagnosis and treatment
Myasthenia gravis diagnosis and treatment
Neuromuscular complications of critical illness diagnosis and treatment
Non-traumatic coma diagnosis
Sedation treatment
Status epilepticus diagnosis and treatment
Stroke diagnosis and treatment
Sub-arachnoid hemorrhage diagnosis and treatment
Aminoglycoside dosing and therapeutic monitoring
Amphotericin-b treatment
Analgesia treatment
Drug changes with renal dysfunction identification and management
Penicillin allergy diagnosis and treatment
Neuromuscular blocker treatment
Vancomycin treatment
Adult Respiratory Distress Syndrome: hemodynamic treatment
Adult Respiratory Distress Syndrome: steroid treatment
Adult Respiratory Distress Syndrome: ventilator treatment
Asthma diagnosis & treatment
Bronchodilator use in ventilator patients
Bronchoscopy & thoracentesis indications
Chronic Obstructive Pulmonary Disease diagnosis and treatment
Chest X-ray indications
Noninvasive modes of ventilation indications and treatment
Endotracheal tubes & tracheotomy indications
Treatment of airway obstruction
Ventilator weaning treatment
Acute renal failure: diagnosis and treatment
Dialysis indications
Diuretic treatment
Hyperkalemia: diagnosis & treatment
Hypernatremia: diagnosis & treatment
Hypokalemia: diagnosis & treatment
Hyponatremia: diagnosis & treatment
Oliguria diagnosis and treatment TABLE 1-continued Obstetrical complications and treatment
Dissecting aortic aneurysm diagnosis and treatment
Post-operative hypertension treatment
Post-operative myocardial ischemia (non-cardiac surgery) treatment
Diagnosis and treatment of arrhythmias after cardiac surgery
Diagnosis and treatment of post-operative bleeding
Post-operative management of abdominal surgery
Post-operative management of open heart surgery
Post-operative management of thoracotomy surgery
Post-operative management of carotid surgery
Wound healing treatment
Diagnosis and treatment of acetaminophen overdose
Diagnosis and treatment of anaphylaxis
Diagnosis and treatment of cocaine toxicity
Diagnosis and treatment of alcohol withdrawal
Diagnosis and treatment of hyperthermia
Diagnosis and treatment of latex allergy
Diagnosis and treatment of unknown poisoning
Diagnosis and treatment of abdominal compartment syndrome
Diagnosis and treatment of blunt abdominal injury
Diagnosis and treatment of blunt aortic injury
Diagnosis and treatment of blunt cardiac injury
Deep Venous Thrombosis prophylaxis treatments
Acid-base disturbance diagnosis and treatment
Electrolyte disturbance diagnosis and treatment
Severity adjustment calculation and outcome prediction
Ventilator treatment
Continuous renal replacement treatment
Infusion pump administration treatment
Fungal infection diagnosis and treatment
Viral infection diagnosis and treatment
Diagnosis and treatment of extremity compartment syndrome
Diagnosis and treatment of head injury
Diagnosis and treatment of hypothermia
Diagnosis and treatment of identification of cervical cord injury
Diagnosis and treatment of spinal cord injury
Diagnosis and treatment of open fractures
Diagnosis and treatment of penetrating abdominal injury
Diagnosis and treatment of penetrating chest injury
Admission criteria
Discharge criteria
Patient triage
Discharge planning FIGS. 6A, B, C and 6D illustrate an application of a decision support algorithm for the diagnosis and treatment of acalculous cholecystitis to patient data according to an embodiment of the present invention. FIGS. 6A through 6D are exemplary only and are not limiting. As will be appreciated by those skilled in the art, decision support algorithms (DSAs) for other conditions may be implemented in the continued patient care software without departing from the scope of the present invention.

Referring to FIG. 6A, a datastore comprising patient data is accessed by the DSA 600 for data indicative of clinical infection. A determination is made whether the data is sufficient to determine whether the patient is clinically infected 602. If the data necessary to make the decision are not available, the system continues its monitoring 604 until data in the datastore indicates otherwise. Alternatively, an alert may be issued on a monitor at the command center although this is not a requirement for further tests to be ordered. Test that are ordered by the DSA are then performed on the patient to obtain the data required for the decision.

If the data are sufficient, a determination is made whether the patient meets criteria for a clinical infection as measured by elevated temperature and leukocystosis 606. In an embodiment of the present invention, the criteria are temperature great than 102 F, or a white blood cell count greater than 12,000. If the criteria for clinical infection are not met, the system of the present invention goes back into its continuous monitoring mode 608. The process is then complete and the continuous monitoring of the present invention continues.

If the patient is clinically infected 606, the DSA accesses the patient data datastore and acquires data indicative of whether the patient has had a previous cholecystectomy 610. A determination is then made whether the data is sufficient to determine whether the patient has had a previous cholecsystectomy 612. If the data necessary to make the decision are not available, the DSA prompts the caregiver to find out this information 613. When the information is obtained it is put into the datastore. Notations of "incomplete data" are kept by the system so that treatment records and need for tests can be audited. This is accomplished by storing an "incomplete data" record 614.

If the data are sufficient, a determination is made whether the patient has had a previous cholecystectomy 616. If the patient has had a previous cholecystectomy, it is very unlikely that the patient has acalculous cholecystitis. Therefore the DSA has completed its analysis for acalculous cholecytitis and the continuous monitoring of the present invention continues for other possible etiologies of infection 618.

Figure 6B:
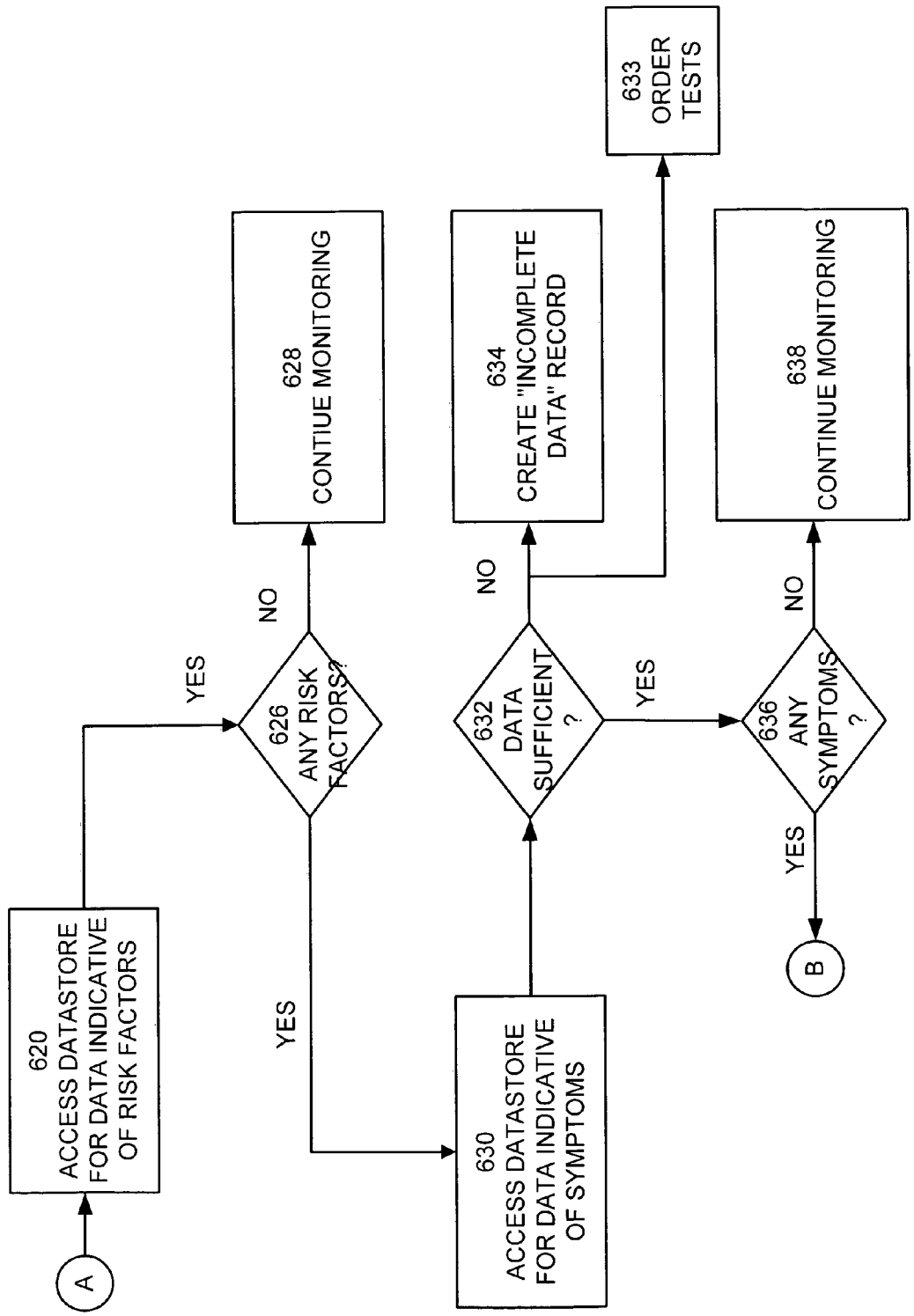

Referring to FIG. 6B, if the patient has not had a previous cholecystectomy, the DSA accesses the patient datastore and acquires data indicative of whether the patient has any of a set of risk factors 620. In another embodiment of the present invention, the risk factors comprise: 1) Prolonged intensive care unit (ICU) stay (defined as greater than six (6) days); 2) recent surgery within the last two weeks (particularly aortic cross clamp procedures); 3) hypotension (BP less than 90 mmHg); 4) positive end-expiratory pressure (PEEP) greater than ten (10) centimeters (cm); 5) transfusion greater than six (6) units of blood; 6) inability to use the gastrointestinal (GI) tract for nutrition; or 7) immunosuppresssion (AIDS, transplantation, or leukemia).

If the data are sufficient, a determination is made whether the patient has any of the risk factors 626. If the patient does not have any of the risk factors, the diagnostic process is then complete and the continuous monitoring of the present invention continues 628.

If the patient has any of the seven risk factors, the DSA accesses the patient data datastore and acquires data indicative of whether the patient has any of a set of symptoms 630 or abnormal laboratory values. A determination is made whether the data is sufficient to determine whether the patient has any of the symptoms 632 or abnormal laboratory values. If the data necessary to make the decision are not available, the DSA directs the order writing software 415 (see FIG. 4) to order the tests 633. Results are sent to the datastore. Notations of "incomplete data" are kept by the system so that treatment records and need for tests can be audited. This is accomplished by storing an "incomplete data" record 634. Alternatively, an alert may be issued on a monitor at the command center to check for right upper quadrant tenderness although this is not a requirement for further tests to be ordered. In another embodiment of the present invention, the symptoms comprise: right upper quadrant (RUQ) tenderness and the abnormal laboratory results comprising elevated alkaline phosphatase; elevated bilirubin; or elevated liver transaminases.

If the data are sufficient, a determination is made whether the patient has any of the symptoms 636 or abnormal laboratory values. If the patient does not have any of the symptoms or abnormal laboratory values, the DSA concludes that it is very unlikely that the patient has acalculous cholecystitis. The process is then complete and the continuous monitoring of the present invention continues 638.

Referring to FIG. 6C, if the patient has any of the symptoms or abnormal laboratory values, the DSA accesses the patient data datastore and acquires data indicative of whether alternative intra-abdominal infectious sources are more likely 640. A determination is made whether the data is sufficient to determine whether the other infectious sources are more likely 642. If the data necessary to make the decision are not available, the DSA prompts the user for a response as to whether other infectious causes are present and considered more likely 644. The user can then provide the requested information that can be considered by the system 646 for further analysis.

If the data are sufficient, a determination is made whether other sources of infection are more likely 646. Regardless of the outcome of this determination, the DSA accesses the patient datastore and acquires data indicative of whether the patient is sufficiently stable to be subjected to testing outside of the critical care environment 650. A determination is made whether the data are sufficient to determine whether the patient is stable to go outside of the critical care environment 652. If the data necessary to make the decision are not available, the DSA prompts the user for a response 654 and may direct the order writing software 415 (see FIG. 4) to order tests or procedures 653 that will assist in such a determination. An "incomplete data" record is also created 651. Test results are sent to the datastore. Notations of "incomplete data" are kept by the system so that treatment records and need for tests can be audited. This is accomplished by storing an "incomplete data" record 654. Alternatively, an alert may be issued on a monitor at the command center although this is not a requirement for further tests to be ordered.

Referring to FIG. 6D, if the data are sufficient, a determination is made whether the patient is sufficiently stable to be subjected to testing outside of the critical care environment 656.

If the patient is not sufficiently stable to be subjected to testing outside of the critical care environment (regardless of whether other sources of infection are indicated), the DSA issues a message comprising a recommendation that empiric antibiotic be considered and a bedside ultrasound be performed and the results communicated to the patient datastore 658. In still another embodiment of the present invention, the DSA directs the order writing software (see FIG. 4) to order the bedside ultrasound. The DSA accesses the test results and other patient data 662. If no other infectious etiologies are identified, no abnormalities of the gall-bladder are noted, and the patient is not improving, the DSA issues a message comprising a "provisional diagnosis of acalculous cholecystitis" and recommends an empiric cholecystectomy and systemic antibiotics 664. If no other infectious etiologies are identified, no abnormalities of the gall bladder are noted, and the patient is improving, the DSA issues a message comprising a recommendation to observe the patient 666.

If the patient is sufficiently stable to go outside of the critical care environment for a test and a determination was made that no other sources of infection were indicated (see FIG. 6C, 646), the DSA issues an order that empiric antibiotics be considered and a morphine sulfate Cholescintigraphy test be performed 668 and the results communicated to the datastore. In still another embodiment of the present invention, the DSA directs the order writing software 415 (see FIG. 4) to order the test.

A determination is made whether the results of the tests are normal 670. If the test indicates an abnormality, the DSA issues a message comprising a recommendation to consider a diagnosis of acalculous cholecystitis, administer systemic antibiotics and perform either a cholecystectomy or a percutaneous drainage 672. If the results are normal, acalculous cholecystitis is excluded 674. The process is then complete and the continuous monitoring of the present invention continues.

If the patient is sufficiently stable to go outside of the critical care environment for a test and a determination was made that other sources of infection were indicated (see FIG. 6C, 646), the DSA issues an order to consider empiric antibiotics and for an abdominal CT scan to be performed 680 and the results communicated to the datastore. In still another embodiment of the present invention, the DSA directs the order writing software 415 (see FIG. 4) to order the test.

The test results and other data are analyzed 682 and a determination is made whether other infection sources are indicated and whether the gall bladder is normal or if abnormalities are present that are not diagnostic 684. If other infectious etiologies are not apparent and the test: a) demonstrates abnormalities of the gall bladder but not diagnostic; or b) no gall-bladder abnormalities are noted, the DSA issues a report comprising a recommendation to maintain continued observation of the patient 686. The process is then complete and the continuous monitoring of the present invention continues. Alternatively, if other infectious etiologies are apparent, the DSA will make recommendations as to further diagnostics and treatments.

Referring again to FIGS. 1 and 2, the remote command center comprises an A/V conferencing server 190. In an embodiment of the present invention, A/V conferencing server 190 acquires audio and video signals from patient monitoring station "A" and provides a terminal (not shown) access to these signals via external network access 195. In yet another embodiment of the present invention addition, a local terminal (not shown) operated by a "local visitation participant" or "LVP" and a remote terminal (not shown) operated by a "remote visitation participant" or "RVP" are bridged by A/V conferencing server 190 to provide audio and video signals from the patient monitoring station, the local terminal and the remote terminal available simultaneously to LVP and RVP. Additionally, a terminal user may control the position of camera 205. By way of illustration and not as a limitation, RVPs may be family members or other concerned parties while LVPs may be patients, nurses, doctors, family members or other concerned parties. This embodiment thus permits family members the capability to "virtually visit" other sick family members when a physical visit to a patient's location is not possible and/or desirable. The "virtual visit" further allows the possibility to see and speak with a care provider regarding a patient's care or related subjects without having to be physically located at the health care provider's location. The present invention also provides a means for the floor staff (i.e. those caregivers in the hospital at or near the patient's bedside) to instantly alert the command center of the conditions of patients who destabilize thereby allowing for more rapid response by those manning the command center.

When each command center person logs onto the system of the present invention, a background service is started. This service subscribes to an emergency alert server that is connected to a video server. As noted earlier, the video server provides video feed from each beside to the command center as needed. Emergency message are passed from the bedside through the video server to the command center. As the emergency alert server receives a message from a video server, it sends a message to all of the subscribed services in the command center. This notification alerts the command center users by means of a "pop-up" alert window at the users' workstation that an emergency condition exists at the bed calling for the alert, and that the floor caregiver has requested immediate backup.

To facilitate the emergency call capability of the present invention, in addition to the various network connections of a more automated type, an emergency "call button" is provided at each critical care location. This could by or near each bed, at a nurse's station, at a mobile care bed or any location where the patient may be located. When pressed, the call button causes a message to be sent to the emergency alert server at the command center that a patient emergency has occurred.

The present invention comprises a video/audio server (Axis 2401) dedicated to each critical care location. A button activation mechanism and associated wiring is provided to allow the call button to be positioned in the room at a location convenient to the caregiver calling for command center backup.

Currently each video server can support up to 16 call buttons by using combinations of the four inputs to signify one alarm in a 4-bit binary pattern although this is not meant as a limitation. A typical installation would use one button or perhaps two (e.g. two beds per room) per video server.

A software interrupt event handler is configured on the video server to respond to activation of the emergency call button.

The emergency alert server comprises a web service called for sending emergency alert signals that is placed in service at system startup. When called, emergency alert web service responds with an acknowledgement message (e.g. "Alert Received"). The emergency alert web service identifies the ward and bed directly from the IP address (unique to each video server) and input number it was passed. It then sends a message to all subscribing clients identifying the emergency condition, the ward, and bed.

When a user logs into a workstation at the command center a user alert service subscribes to the emergency alert server and waits for any emergency message in the background. Upon receiving an emergency message, the service will popup a window with the message on top of the desktop and stay there until the user dismisses or acknowledges the alert. The user alert service the loads video assessment module to allow the command center to view the bed with the emergency.

In another embodiment of the present invention, a critical care hospital bed comprises monitoring instruments linked to a wireless network. This serves the needs of those patients who are transported from one location to another (either internal to a hospital or to other hospitals or diagnostic centers) for testing, procedures or other reasons. In this embodiment, monitoring continues using typical monitoring means that have been described above which include, without limitation, physiological monitoring equipment, video monitoring equipment and an emergency call button, all of which transmit their signals in a wireless fashion so that movement of the patient bed does not interrupt the transmission of information.

A telecommunications network for remote patient monitoring has now been illustrated. It will be apparent to those skilled in the art that other variations of the present invention are possible without departing from the scope of the invention as disclosed. For example, one can envision different ratios of remote command center to patient monitoring stations. Certain types of decision support algorithms would be used by intensivists, other types of remote monitoring of not only patient monitoring stations but other types of hospital functions as well as industrial functions where critical expertise is in limited supply but where that expertise must be applied to ongoing processes. In such cases a system such as that described can be employed to monitor processes and to provide standardized interventions across a number of locations and operations. Further, any reference to claim elements in the singular, for example, using the articles "a," "an," or "the" is not to be construed as limiting the element to the singular.

What is claimed is:

1. A system for providing expert care simultaneously to a plurality of basic care medical facilities (BCMFs) in seperate geographic locations comprising:
a network;
a remote command center dedicated to monitoring and managing the care of BCMF patients, which is apart from the BCMFs and is connected to the network, wherein the remote command center has access to an organized collection of electronic information (database);
monitoring stations located in the plurality of BCMFs, wherein the monitoring stations comprise instructions for obtaining data elements from patients who are located in the plurality of BCMFs (monitored patient data elements) and for communicating the monitored patient data elements to the database via the network, wherein the database comprises stored patient data elements comprising the monitored patient data elements and other patient data elements associated with medical conditions of the BCMF patients; and
wherein the remote command center has access to a patient care management system, which comprises instructions for:
accessing patient data elements from the stored patient data elements in the database;
utilizing a rules engine to apply rules repeatedly and automatically to at least two patient data elements according to the rules of the rules engine 24 hours per day 7 days per week, wherein the rules identify medical conditions that may warrant management by a health care provider;
using information generated by the rules engine to determine if an alert should be provided; and
simultaneously displaying alerts at the remote command center for all patients for whom the patient care system determines that an alert should be displayed at the remote command center.

2. The system of claim 1, wherein the rules engine applies the rules in a time-driven fashion.

3. The system of claim 1, wherein the rules engine applies the rules in an event-driven fashion.

4. The system of claim 1, wherein BCMF is selected from the group consisting of a hospital, a nursing home, a mobile health care facility, a space-based health care facility, a residence, an emergency room, an intensive care unit, a field health care facility, an operating room, and a step-down unit.

5. The system of claim 1, wherein the monitored patient data elements are physiological data elements.

6. The system of claim 1, wherein the other patient data elements associated with the medical conditions of the BCMF patients are selected from the group consisting of patient medical histories, physician notes, lab reports and medications.

7. The system of claim 1, wherein the at least two patient data elements comprise a physiological data element of the BCMF patients and a clinical data element of the BCMF patients.

8. The system of claim 1, wherein the at least two patient data elements comprise a physiological data element of the BCMF patients and a medication data element of the BCMF patients.

9. The system of claim 1, wherein the at least two patient data elements comprise a physiological data element of the BCMF patients and a laboratory data element of the BCMF patients.

10. The system of claim 1, wherein the at least two patient data elements comprise a clinical data element of the BCMF patients and a laboratory data element of the BCMF patients.

11. The system of claim 1, wherein the at least two patient data elements comprise two physiological data elements of the BCMF patients.

12. The system of claim 1, wherein the at least two data elements comprise at least two data elements of the BCMF patients selected from the group consisting of a physiological data element, a clinical data element of the BCMF patients, a medication data element of the BCMF patients, and a laboratory data element of the BCMF patients.

13. The system of claim 1 wherein the patient care system further comprises instructions for:
receiving information relating to a medical condition of a BCMF patient;
applying a decision support algorithm to the information; and
providing a response based upon application of the decision support algorithm to the information.

14. The system of claim 13 wherein the decision support algorithm comprises a guideline of practice relating to:
Acalculous Cholecystitis, Acute Pancreatitis, Acute Renal Failure Diagnosis, Acute Renal Failure-Management & Treatment, Adrenal Insufficiency, Agitation and Anxiety, Depression & Withdrawal, Aminoglycoside Dosing and Therapeutic Monitoring, an Amphotericin-B Treatment Guidelines, Analgesia, Antibiotic Classification & Costs, Antibiograms, Antibiotic associated Colitis, ARDS: Hemodynamic Management, ARDS: Steroid Use, ARDS: Ventilator Strategies, Asthma, Bleeding Patient, Bloodstream Infections, Blunt Cardiac Injury, Bradyarrhythmias, Brain Death, Bronchodilator Use in Ventilator Patients, Bronchoscopy & Thoracentesis Guidelines, Candiduria, Cardiogenic Shock, CardioPulmonary Resuscitation Guideline, Catheter Related Septicemia, a Catheter Replacement Strategies, Cervical Cord Injury, Congestive Heart Failure, COPD Exacerbation & Treatment, CXR (Indications), Dealing with Difficult patients and families, Diabetic Ketoacidosis, Dialysis, Diuretic Use, Drug Changes with Renal Dysfunction, Emergency Cardiac Pacing, Endocarditis Diagnosis and Treatment, Endocarditis Prophylaxis, End of Life Decisions, Endotracheal Tubes & Tracheotomy, Ethical Guidelines, Febrile Neutropenia, FUO, Fluid Resuscitation, Guillain-Barre Syndrome, Heparin, Heparin-Induced Thrombocytopenia, Hepatic Encephalopathy, Hepatic Failure, HIV+Patient Infections, Hypercalcemia Diagnosis and Treatment, Hypercalcemia Insulin Treatment, Hyperkalemia: Etiology & Treatment, Hypernatremia: Etiology & Treatment, Hypertensive Crisis, Hypokalemia: Etiology & Treatment, Hyponatremia: Etiology & Treatment, Hypothermia, Identification of Cervical Cord Injury, Implantable Cardio-defibrillator, Intra-Aortic Balloon Device, Intracerebral Hemorrhage, Latex Allergy, Magnesium Administration, Management of Hypotension, Inotropes, Management of Patients with Ascites, Empiric Antibiotics for Meningitis, Myasthenia Gravis, Myocardial Infarction, Myocardial Infarction with left bundle branch block, Necrotizing Soft Tissue Infections, Neuromuscular Blockers, Neuromuscular Complications of Critical Illness, Non-Infectious Causes of Fever, Non- Traumatic Coma, Noninvasive Modes of Ventilation, Nutritional Management, Obstetrical Complications, Oliguria, Open Fractures, Ophthalmic Infections, Organ Procurement Guidelines, PA Catheter Guideline and Troubleshooting, Pancreatitis, Penetrating Abdominal Injury, Penetrating Chest Injury, Penicillin Allergy, Permanent Pacemaker and Indications, Pneumonia Community Acquired, Pneumonia Hospital Acquired, Post-Op Bleeding, Post-Op Hypertension, Post-Op Management of Abdominal Surgery, Post-Op Management of Carotid Surgery, Post-Op Management of Open Heart Surgery, Post-Op Management of Thoracotomy Surgery, Post-Op Myocardial Ischemnia, Cardiac Arrhythmias after Non-Cardiac Surgery, Post-Op Power Weaning, Pressure Ulcers, Pulmonary Embolism Diagnosis, Pulmonary Embolism Treatment, Respiratory Isolation, Sedation, Seizure, Status Epilepticus, Stroke, Sub-Arachnoid Hemorrhage, Supra-Ventricular Tachyarrythmia, Supra-Ventricular Tachycardia, Wide Complex QRS Tachycardia, Therapeutic Drug Monitoring, Thrombocytopenia, Thirombolytic Therapy, Transfusion Guidelines, Traumatic Brain Injury, Assessment of Sedation, Sedation, Septic Shock, Bolus Sliding Scale Midazolam, Short Term Sedation Process, Sinusitis, SIRS, Spinal Cord Injury, Steroid Replacement Strategy, Thyroid Disease, Transplant Infection Prophylaxis, Transplant Related Infections, Treatment of Airway Obstruction, Unknown Poisoning, Unstable Angina, Upper GI Bleeding Stress Prophylaxis, Vancomycin, Upper GI Bleeding Non-Variceal, Upper GI Bleeding Variceal, Use of Hematopoiectic Growth Factors, Ventilator Weaning, Ventilator Weaning Protocol, Venous Thrombosis Diagnosis and Treatment, Venous Thromboembolism Prophylaxis, Ventricular Arrhythmia, Warfarin, Warfarin Dosing, and Wound Healing Strategies.

15. The system of claim 13, wherein the response is selected from the group consisting of a diagnosis, a method of treatment, and an order for a laboratory protocol.

16. The system of claim 1 wherein, the patient care system further comprises an order writing module, wherein the decision support system further comprises instructions for:
applying the order writing module to stored patient data for a BCMF patient; and
issuing an order based on the stored patient data.

17. The system of claim 16, wherein the order is selected from the group consisting of an authorization to administer medication to the BCMF patient, an authorization to subject the BCMF patient to a laboratory protocol, and an authorization to subject the BCMF patient to a surgical procedure.

18. The system of claim 1, wherein the BCMF further comprises a video system comprising instructions for obtaining video from the BCMF patients who are located in the plurality of BCMFs and for communicating the video via the network, wherein the video from the video system is received at the remote command center.

19. The system of claim 1, wherein the BCMF further comprises an audio system comprising instructions for obtaining audio from the BCMF patients who are located in the plurality of BCMFs and for communicating the audio via the network, wherein the audio from the audio system is received at the remote command center.

20. The system of claim 1, wherein the patient care system further comprises instructions for:
determining whether a BCMF patient requires monitoring by the monitoring station; and
issuing a release order in the event the BCMF patient does not require monitoring by the monitoring station.

21. The system of claim 1, wherein the network is selected from the group consisting of a wired network, a wireless network, a satellite network, a public switched telephone network, an IP network, a packet switched network, a cell phone network, a cable network, a coax network, and a hybrid fiber coax network.

22. The system of claim 1, wherein the BCMF further comprises a site assessment module and a network interface, and wherein the site assessment module comprises instructions for:
receiving site assessment data, wherein the site assessment data are indicative of the capability of the BCMF to provide expert care to the BCMF patients; and
determining from the site assessment data service level measures, and
wherein the communications interface comprises instructions for transmitting the service level measures to the remote command center via the network, and wherein the patient care system further comprises instructions for receiving the service level measures from the BCMF and applying rules consistent with the service level measures.

23. The system of claim 22 wherein the patient care system further comprises instructions for:
receiving information relating to a medical condition of a BCMF patient;
applying a decision support algorithm to the information consistent with the service level measures; and
providing a response based upon application of the decision support algorithm to the information consistent with the service level measures.

24. The system of claim 23 wherein the decision support algorithm comprises a guideline of practice relating to:
Acalculous Cholecystitis, Acute Pancreatitis, Acute Renal Failure Diagnosis, Acute Renal Failure-Management & Treatment, Adrenal Insufficiency, Agitation and Anxiety, Depression & Withdrawal, Aminoglycoside Dosing and Therapeutic Monitoring, an Amphotericin-B Treatment Guidelines, Analgesia, Antibiotic Classification & Costs, Antibiograms, Antibiotic associated Colitis, ARDS: Hemodynamic Management, ARDS: Steroid Use, ARDS: Ventilator Strategies, Asthma, Bleeding Patient, Bloodstream Infections, Blunt Cardiac Injury, Bradyarrhythmias, Brain Death, Bronchodilator Use in Ventilator Patients, Bronchoscopy & Thoracentesis Guidelines, Candiduria, Cardiogenic Shock, CardioPulmonary Resuscitation Guideline, Catheter Related Septicemia, a Catheter Replacement Strategies, Cervical Cord Injury, Congestive Heart Failure, COPD Exacerbation & Treatment, CXR (Indications), Dealing with Difficult patients and families, Diabetic Ketoacidosis, Dialysis, Diuretic Use, Drug Changes with Renal Dysfunction, Emergency Cardiac Pacing, Endocarditis Diagnosis and Treatment, Endocarditis Prophylaxis, End of Life Decisions, Endotracheal Tubes & Tracheotomy, Ethical Guidelines, Febrile Neutropenia, FUO, Fluid Resuscitation, Guillain-Barre Syndrome, Heparin, Heparin-Induced Thrombocytopenia, Hepatic Encephalopathy, Hepatic Failure, HIV+Patient Infections, Hypercalcemia Diagnosis and Treatment, Hypercalcemia Insulin Treatment, Hyperkalemia: Etiology & Treatment, Hypematremia: Etiology & Treatment, Hypertensive Crisis, Hypokalemia: Etiology & Treatment, Hyponatremia: Etiology & Treatment, Hypothermia, Identification of Cervical Cord Injury, Implantable Cardio-defibrillator, Intra-Aortic Balloon Device, Intracerebral Hemorrhage, Latex Allergy, Magnesium Administration, Management of Hypotension, Inotropes, Management of Patients with Ascites, Empiric Antibiotics for Meningitis, Myasthenia Gravis, Myocardial Infarction, Myocardial Infarction with left bundle branch block, Necrotizing Soft Tissue Infections, Neuromuscular Blockers, Neuromuscular Complications of Critical Illness, Non-Infectious Causes of Fever, Non-Traumatic Coma, Noninvasive Modes of Ventilation, Nutritional Management, Obstetrical Complications, Oliguria, Open Fractures, Ophthalmic Infections, Organ Procurement Guidelines, PA Catheter Guideline and Troubleshooting, Pancreatitis, Penetrating Abdominal Injury, Penetrating Chest Injury, Penicillin Allergy, Permanent Pacemaker and Indications, Pneumonia Community Acquired, Pneumonia Hospital Acquired, Post-Op Bleeding, Post-Op Hypertension, Post-Op Management of Abdominal Surgery, Post-Op Management of Carotid Surgery, Post-Op Management of Open Heart Surgery, Post-Op Management of Thoracotomy Surgery, Post-Op Myocardial Ischemnia, Cardiac Arrhythmias after Non-Cardiac Surgery, Post-Op Power Weaning, Pressure Ulcers, Pulmonary Embolism Diagnosis, Pulmonary Embolism Treatment, Respiratory Isolation, Sedation, Seizure, Status Epilepticus, Stroke, Sub-Arachnoid Hemorrhage, Supra-Ventricular Tachyarrythmia, Supra-Ventricular Tachycardia, Wide Complex QRS Tachycardia, Therapeutic Drug Monitoring, Thrombocytopenia, Thirombolytic Therapy, Transfusion Guidelines, Traumatic Brain Injury, Assessment of Sedation, Sedation, Septic Shock, Bolus Sliding Scale Midazolam, Short Term Sedation Process, Sinusitis, SIRS, Spinal Cord Injury, Steroid Replacement Strategy, Thyroid Disease, Transplant Infection Prophylaxis, Transplant Related Infections, Treatment of Airway Obstruction, Unknown Poisoning, Unstable Angina, Upper GI Bleeding Stress Prophylaxis, Vancomycin, Upper GI Bleeding Non-Variceal, Upper GI Bleeding Variceal, Use of Hematopoiectic Growth Factors, Ventilator Weaning, Ventilator Weaning Protocol, Venous Thrombosis Diagnosis and Treatment, Venous Thromboembolism Prophylaxis, Ventricular Arrhythmia, Warfarin, Warfarin Dosing, and Wound Healing Strategies.

25. The system of claim 23, wherein the response is selected from the group consisting of a diagnosis, a method of treatment, and an order for a laboratory protocol.

26. The system of claim 22, wherein the patient care system further comprises an order writing module and wherein the patient care system further comprises instructions for:
applying the order writing module to stored patient data of a BCMF patient; and
issuing an order based on the stored patient data that is consistent with the service level measures.

27. The system of claim 26, wherein the order is selected from the group consisting of an authorization to administer medication to the BCMF patient, an authorization to subject the BCMF patients to a laboratory protocol, and an authorization to subject the BCMF patients to a surgical procedure.

28. The system of claim 22, wherein the site assessment module further comprises instructions for:
prompting a user for the site assessment information; and
determing the service level measures based on the user response.

29. The system of claim 22, wherein a monitoring station comprises a site assessment code associated with service levels measures and wherein the site assessment module further comprises instructions for:
acquiring the site assessment code from the monitoring station; and
determining the service level measures at least in part based on the site assessment code associated with the monitoring station.

30. The system of claim 22, wherein the service level measures comprise:
an inventory of available monitoring data elements;
an inventory of available diagnostic services;
an inventory of available surgical treatment services; and
an inventory of available laboratory services.

31. The system of claim 1 further comprising a communications scheduler, wherein the communications schedule comprises instructions for establishing communications between the monitoring stations and the database at a predetermined interval.

32. The system of claim 31, further comprising an urgent consultation warning system, wherein the urgent consultation warning system comprises instructions for:
establishing an urgent consultation rule for a BCMF patient;
applying the urgent consultation rule to the patient data elements of the BCMF patient;
determining whether urgent consultation rule has been contravened; and
issuing an urgent communication signal if the urgent consultation rule has been contravened, and
wherein, the communications scheduler further comprises instructions for:
receiving the urgent communication signal; and
establishing communications between a monitoring station associated with the BCMF patient and the database without regard to the predetermined interval.

33. The system of claim 1, wherein the remote command center further comprises:
an external network interface, and wherein the external network interface comprises instructions for:
connecting to an external network; and
providing a health care provider access to the remote command center via the external network.

34. The system of claim 33, wherein the external network is selected from the group consisting of a wired network, a wireless network, a cable network, a fiber optic network, and the Internet.

35. The system of claim 33, wherein the health care provider is selected from the group consisting of a physician, a nurse, a clinician, a diagnostician, and a intensivist.

36. The system of claim 33, wherein the remote command center further comprises instructions for sending the health care provider the alerts.

37. The system of claim 1, wherein the separate geographic locations are locations within a structure.

38. The system of claim 1, wherein the separate geographic locations are locations within different structures.

39. A method for providing, from a remote command center, expert care simultaneously to a plurality of basic care medical facilities (BCMFs) in separate geographic locations, wherein the remote command center is a dedicated location for monitoring and managing BCMF patients, is apart from the BCMFs and has access to an organized collection of electronic information (database), the method comprising:
obtaining patient data elements from patients who are located in the plurality of BCMFs, wherein the monitoring stations obtain data elements from patients who are located in the plurality of BCMFs (monitored patient data elements);

communicating the monitored patient data elements to the database via the network, wherein the database comprises stored patient data elements comprising the monitored patient data elements and other patient data elements associated with medical conditions of the BCMF patients;

receiving at the remote command center alerts, wherein the alerts are provided by a patient care system, which system utilizes a rules engine to apply rules, repeatedly and automatically to at least two patient data elements according to the rules of the rules engine 24 hours per day 7 days per week, wherein the rules applied by the rules engine identify existing or potential conditions that may warrant management by a health care provider, and wherein the computerized patient care system:

uses information generated by the rules engine to determine if an alert should be provided, and simultaneously displays alerts at the remote command center for all patients for whom the computerized patient care management system determines that an alert should be displayed at the remote command center.

40. The method of claim 39, wherein the rules engine applies the rules in a time-driven fashion.

41. The method of claim 39, wherein the rules engine applies the rules in an event-driven fashion.

42. The method of claim 39, wherein the BCMF is selected from the group consisting of a hospital, a nursing home, a mobile health care facility, a space-based health care facility, a residence, an emergency room, an intensive care unit, a field health care facility, an operating room, and a step-down unit.

43. The method of claim 39, wherein the monitored patient data elements are physiological data elements.

44. The method of claim 39, wherein the at least two patient data elements comprise a physiological measure and a clinical data element of the BCMF patients.

45. The method of claim 39, wherein the at least two patient data elements comprise a physiological data element of the BCMF patients and a medication data element of the BCMF patients.

46. The method of claim 39, wherein the at least two patient data elements comprise a physiological data element of the BCMF patients and a laboratory data element of the BCMF patients.

47. The method of claim 39, wherein the at least two patient data elements comprise a clinical data element of the BCMF patients and a laboratory data element of the BCMF patients.

48. The method of claim 39, wherein the at least two patient data elements comprise two physiological data elements of the BCMF patients.

49. The method of claim 39 further comprising:

receiving information relating to a medical condition of a BCMF patient;

applying a decision support algorithm to the information; and providing a response based upon application of the decision support algorithm to the information.

50. The method of claim 49 wherein the decision support algorithm comprises a guideline of practice relating to:

Acalculous Cholecystitis, Acute Pancreatitis, Acute Renal Failure Diagnosis, Acute Renal Failure-Management & Treatment, Adrenal Insufficiency, Agitation and Anxiety, Depression & Withdrawal, Aminoglycoside Dosing and Therapeutic Monitoring, an Amphotericin-B Treatment Guidelines, Analgesia, Antibiotic Classification & Costs, Antibiograms, Antibiotic associated Colitis, ARDS: Hemodynamic Management, ARDS: Steroid Use, ARDS: Ventilator Strategies, Asthma, Bleeding Patient, Bloodstream Infections, Blunt Cardiac Injury, Bradyarrhythmias, Brain Death, Bronchodilator Use in Ventilator Patients, Bronchoscopy & Thoracentesis Guidelines, Candiduria, Cardiogenic Shock, CardioPulmonary Resuscitation Guideline, Catheter Related Septicemia, a Catheter Replacement Strategies, Cervical Cord Injury, Congestive Heart Failure, COPD Exacerbation & Treatment, CXR (Indications), Dealing with Difficult patients and families, Diabetic Ketoacidosis, Dialysis, Diuretic Use, Drug Changes with Renal Dysfunction, Emergency Cardiac Pacing, Endocarditis Diagnosis and Treatment, Endocarditis Prophylaxis, End of Life Decisions, Endotracheal Tubes & Tracheotomy, Ethical Guidelines, Febrile Neutropenia, FUO, Fluid Resuscitation, Guillain-Barre Syndrome, Heparin, Heparin-Induced Thrombocytopenia, Hepatic Encephalopathy, Hepatic Failure, HIV+Patient Infections, Hypercalcemia Diagnosis and Treatment, Hypercalcemia Insulin Treatment, Hyperkalemia: Etiology & Treatment, Hypernatremia: Etiology & Treatment, Hypertensive Crisis, Hypokalemia: Etiology & Treatment, Hyponatremia: Etiology & Treatment, Hypothermia, Identification of Cervical Cord Injury, Implantable Cardio-defibrillator, Intra-Aortic Balloon Device, Intracerebral Hemorrhage, Latex Allergy, Magnesium Administration, Management of Hypotension, Inotropes, Management of Patients with Ascites, Empiric Antibiotics for Meningitis, Myasthenia Gravis, Myocardial Infarction, Myocardial Infarction with left bundle branch block, Necrotizing Soft Tissue Infections, Neuromuscular Blockers, Neuromuscular Complications of Critical Illness, Non-Infectious Causes of Fever, Non-Traumatic Coma, Noninvasive Modes of Ventilation, Nutritional Management, Obstetrical Complications, Oliguria, Open Fractures, Ophthalmic Infections, Organ Procurement Guidelines, PA Catheter Guideline and Troubleshooting, Pancreatitis, Penetrating Abdominal Injury, Penetrating Chest Injury, Penicillin Allergy, Permanent Pacemaker and Indications, Pneumonia Community Acquired, Pneumonia Hospital Acquired, Post-Op Bleeding, Post-Op Hypertension, Post-Op Management of Abdominal Surgery, Post-Op Management of Carotid Surgery, Post-Op Management of Open Heart Surgery, Post-Op Management of Thoracotomy Surgery, Post-Op Myocardial Ischemnia, Cardiac Arrhythmias after Non-Cardiac Surgery, Post-Op Power Weaning, Pressure Ulcers, Pulmonary Embolism Diagnosis, Pulmonary Embolism Treatment, Respiratory Isolation, Sedation, Seizure, Status Epilepticus, Stroke, Sub-Arachnoid Hemorrhage, Supra-Ventricular Tachyarrythmia, Supra-Ventricular Tachycardia, Wide Complex QRS Tachycardia, Therapeutic Drug Monitoring, Thrombocytopenia, Thirombolytic Therapy, Transfusion Guidelines, Traumatic Brain Injury, Assessment of Sedation, Sedation, Septic Shock, Bolus Sliding Scale Midazolam, Short Term Sedation Process, Sinusitis, SIRS, Spinal Cord Injury, Steroid Replacement Strategy, Thyroid Disease, Transplant Infection Prophylaxis, Transplant Related Infections, Treatment of Airway Obstruction, Unknown Poisoning, Unstable Angina, Upper GI Bleeding Stress Prophylaxis, Vancomycin, Upper GI Bleeding Non-Variceal, Upper GI Bleeding Variceal, Use of Hematopoiectic Growth Factors, Ventilator Weaning, Ventilator Weaning Protocol, Venous Thrombosis Diagnosis and Treatment, Venous Thromboembolism Prophylaxis, Ventricular Arrhythmia, Warfarin, Warfarin Dosing, and Wound Healing Strategies.

51. The method of claim 49, wherein the response is selected from the group consisting of a diagnosis, a method of treatment, and an order for a laboratory protocol.

52. The method of claim 39 further comprising:
accessing an order writing module; and
issuing an order based on the stored patient data.

53. The method of claim 52, wherein the order is selected from the group consisting of an authorization to administer medication to a BCMF patient, an authorization to subject a BCMF patient to a laboratory protocol, and an authorization to subject the BCMF patients to a surgical procedure.

54. The method of claim 39 further comprising:
obtaining video of the patients who are located in the plurality of BCMFs; and
accessing at the remote command center the video from the patients in the plurality of BCMFs.

55. The method of claim 39 further comprising:
obtaining audio of the patients who are located in the plurality of BCMFs; and
accessing at the remote command center the audio from the patients in the plurality of BCMFs.

56. The method of claim 39 further comprising:
determining whether a BCMF patient requires monitoring; and
issuing a release order in the event the BCMF patient does not require monitoring.

57. The method of claim 39, wherein the network is selected from the group consisting of a wired network, a wireless network, a satellite network, a public switched telephone network, an IP network, a packet switched network, a cell phone network, a cable network, a coax network, and a hybrid fiber coax network.

58. The method of claim 39 further comprising:
receiving site assessment data, wherein the site assessment data are indicative of the capability of the BCMF to provide expert care to the BCMF patients;
determining service level measures; and
communicating over the network the service level measures to a remote command center, and wherein applying rules further comprises applying rules consistent with the service level measures.

59. The method of claim 58, wherein the method further comprises:
receiving information relating to a medical condition of a BCMF patient;
applying a decision support algorithm to the information consistent with the service level measures; and
providing a response based upon application of the decision support algorithm to the information consistent with the service level measures.

60. The method of claim 59 wherein the decision support algorithm comprises a guideline of practice relating to:
Acalculous Cholecystitis, Acute Pancreatitis, Acute Renal Failure Diagnosis, Acute Renal Failure-Management & Treatment, Adrenal Insufficiency, Agitation and Anxiety, Depression & Withdrawal, Aminoglycoside Dosing and Therapeutic Monitoring, an Amphotericin-B Treatment Guidelines, Analgesia, Antibiotic Classification & Costs, Antibiograms, Antibiotic associated Colitis, ARDS: Hemodynamic Management, ARDS: Steroid Use, ARDS: Ventilator Strategies, Asthma, Bleeding Patient, Bloodstream Infections, Blunt Cardiac Injury, Bradyarrhythmias, Brain Death, Bronchodilator Use in Ventilator Patients, Bronchoscopy & Thoracentesis Guidelines, Candiduria, Cardiogenic Shock, CardioPulmonary Resuscitation Guideline, Catheter Related Septicemia, a Catheter Replacement Strategies, Cervical Cord Injury, Congestive Heart Failure, COPD Exacerbation & Treatment, CXR (Indications), Dealing with Difficult patients and families, Diabetic Ketoacidosis, Dialysis, Diuretic Use, Drug Changes with Renal Dysfunction, Emergency Cardiac Pacing, Endocarditis Diagnosis and Treatment, Endocarditis Prophylaxis, End of Life Decisions, Endotracheal Tubes & Tracheotomy, Ethical Guidelines, Febrile Neutropenia, FUO, Fluid Resuscitation, Guillain-Barre Syndrome, Heparin, Heparin-Induced Thrombocytopenia, Hepatic Encephalopathy, Hepatic Failure, HIV+Patient Infections, Hypercalcemia Diagnosis and Treatment, Hypercalcemia Insulin Treatment, Hyperkalemia: Etiology & Treatment, Hypernatremia: Etiology & Treatment, Hypertensive Crisis, Hypokalemia: Etiology & Treatment, Hyponatremia: Etiology & Treatment, Hypothermia, Identification of Cervical Cord Injury, Implantable Cardio-defibrillator, Intra-Aortic Balloon Device, Intracerebral Hemorrhage, Latex Allergy, Magnesium Administration, Management of Hypotension, Inotropes, Management of Patients with Ascites, Empiric Antibiotics for Meningitis, Myasthenia Gravis, Myocardial Infarction, Myocardial Infarction with left bundle branch block, Necrotizing Soft Tissue Infections, Neuromuscular Blockers, Neuromuscular Complications of Critical Illness, Non-Infectious Causes of Fever, Non-Traumatic Coma, Noninvasive Modes of Ventilation, Nutritional Management, Obstetrical Complications, Oliguria, Open Fractures, Ophthalmic Infections, Organ Procurement Guidelines, PA Catheter Guideline and Troubleshooting, Pancreatitis, Penetrating Abdominal Injury, Penetrating Chest Injury, Penicillin Allergy, Permanent Pacemaker and Indications, Pneumonia Community Acquired, Pneumonia Hospital Acquired, Post-Op Bleeding, Post-Op Hypertension, Post-Op Management of Abdominal Surgery, Post-Op Management of Carotid Surgery, Post-Op Management of Open Heart Surgery, Post-Op Management of Thoracotomy Surgery, Post-Op Myocardial Ischemnia, Cardiac Arrhythmias after Non-Cardiac Surgery, Post-Op Power Weaning, Pressure Ulcers, Pulmonary Embolism Diagnosis, Pulmonary Embolism Treatment, Respiratory Isolation, Sedation, Seizure, Status Epilepticus, Stroke, Sub-Arachnoid Hemorrhage, Supra-Ventricular Tachyarrythmia, Supra-Ventricular Tachycardia, Wide Complex QRS Tachycardia, Therapeutic Drug Monitoring, Thrombocytopenia, Thirombolytic Therapy, Transfusion Guidelines, Traumatic Brain Injury, Assessment of Sedation, Sedation, Septic Shock, Bolus Sliding Scale Midazolam, Short Term Sedation Process, Sinusitis, SIRS, Spinal Cord Injury, Steroid Replacement Strategy, Thyroid Disease, Transplant Infection Prophylaxis, Transplant Related Infections, Treatment of Airway Obstruction, Unknown Poisoning, Unstable Angina, Upper GI Bleeding Stress Prophylaxis, Vancomycin, Upper GI Bleeding Non-Variceal, Upper GI Bleeding Variceal, Use of Hematopoiectic Growth Factors, Ventilator Weaning, Ventilator Weaning Protocol, Venous Thrombosis Diagnosis and Treatment, Venous Thromboembolism Prophylaxis, Ventricular Arrhythmia, Warfarin, Warfarin Dosing, and Wound Healing Strategies.

61. The method of claim 59, wherein the response is selected from the group consisting of a diagnosis, a method of treatment, and an order for a laboratory protocol.

62. The method of claim 58, wherein the method further comprises:
prompting a user for the site assessment information; and
determining the service level measures based on the user response.

63. The method of claim 58, wherein a monitoring station is associated with a site assessment code and the method further comprises:
acquiring the site assessment code associated with the monitoring station; and
determining the service level measures at least in part based on the site assessment code associated with the monitoring station.

64. The method of claim 58, wherein the service level measures comprise:
an inventory of available monitoring data elements;
an inventory of available diagnostic services;
an inventory of available surgical treatment services; and
an inventory of available laboratory services.

65. The method of claim 39 further comprising:
accessing an order writing module;
applying the order writing module to the stored patient data of a BCMF patient; and
issuing an order based on the stored patient data that is consistent with the service level measures.

66. The method of claim 65, wherein the order is selected from the group consisting of an authorization to administer medication to the BCMF patient, an authorization to subject the BCMF patient to a laboratory protocol, and an authorization to subject the BCMF patient to a surgical procedure.

67. The method of claim 39 further, wherein communicating the monitored patient data elements to the database via the network comprises communicating the monitored patient data elements to the database at a pre-determined interval.

68. The method of claim 67 further comprising:
establishing an urgent consultation rule for a BCMF patient;
applying the urgent consultation rule to the patient data elements of the BCMF patient;
determining whether urgent consultation rule has been contravened; and
establishing communications between a monitoring station associated with the BCMF patient and the database without regard to the predetermined interval if the urgent consultation rule has been contravened.

69. The method of claim 39 further comprising:
interfacing with an external network; and
providing a health care provider access to the remote command center via the external network.

70. The method of claim 69, wherein the external network is selected from the group consisting of a wired network, a wireless network, a cable network, a fiber optic network, and the Internet.

71. The method of claim 70, wherein the health care provider is selected from the group consisting of a physician, a nurse, a clinician, a diagnostician, and an intensivist.

72. The method of claim 71 further comprising sending the health care provider the alerts.

73. The method of claim 39, wherein the separate geographic locations are locations within a structure.

74. The method of claim 39, wherein the separate geographic locations are locations within different structures.

* * * * *